US012570980B2

(12) United States Patent
Pettine et al.

(10) Patent No.: US 12,570,980 B2
(45) Date of Patent: *Mar. 10, 2026

(54) METHODS AND COMPOSITIONS FOR TREATING INFLAMMATORY CONDITIONS ASSOCIATED WITH INFECTIOUS DISEASE

(71) Applicant: Direct Biologics, LLC, Austin, TX (US)

(72) Inventors: Kenneth Allen Pettine, Fort Collins, CO (US); Kevin Hicok, San Diego, CA (US); Timothy Alexander Moseley, Fallbrook, CA (US)

(73) Assignee: Direct Biologics, LLC, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/098,197

(22) Filed: Apr. 2, 2025

(65) Prior Publication Data

US 2025/0277217 A1 Sep. 4, 2025

Related U.S. Application Data

(63) Continuation of application No. 17/920,997, filed as application No. PCT/US2021/028686 on Apr. 22, 2021.

(60) Provisional application No. 63/198,706, filed on Nov. 6, 2020, provisional application No. 63/013,865, filed on Apr. 22, 2020.

(51) Int. Cl.
| | |
|---|---|
| *C12N 15/113* | (2010.01) |
| *A61K 9/127* | (2006.01) |
| *A61K 38/17* | (2006.01) |
| *A61K 45/06* | (2006.01) |
| *A61P 31/14* | (2006.01) |

(52) U.S. Cl.
CPC .......... *C12N 15/1137* (2013.01); *A61K 9/127* (2013.01); *A61K 38/1709* (2013.01); *A61K 38/177* (2013.01); *A61K 45/06* (2013.01); *A61P 31/14* (2018.01); *C12N 15/1136* (2013.01); *C12N 2310/141* (2013.01)

(58) Field of Classification Search
CPC .. A61K 9/127; A61K 38/1709; A61K 38/177; A61K 45/06
See application file for complete search history.

(56) References Cited

U.S. PATENT DOCUMENTS

| | | | |
|---|---|---|---|
| 3,610,795 | A | 10/1971 | Antoine et al. |
| 4,897,355 | A | 1/1990 | Eppstein et al. |
| 5,135,917 | A | 8/1992 | Burch et al. |
| 5,712,163 | A | 1/1998 | Parenteau et al. |
| 6,410,588 | B1 | 6/2002 | Feldmann et al. |
| 7,029,666 | B2 | 4/2006 | Bruder et al. |

| | | | |
|---|---|---|---|
| 8,021,882 | B2 | 9/2011 | Johnstone et al. |
| 8,057,789 | B2 | 11/2011 | Hariri |
| 8,372,797 | B2 | 2/2013 | Ichim |
| 8,703,710 | B2 | 4/2014 | Dzau et al. |
| 8,778,416 | B2 | 7/2014 | Cohen |
| 9,408,874 | B2 | 8/2016 | Pettine |
| 9,744,130 | B2 | 8/2017 | Lipp et al. |
| 9,856,455 | B2 | 1/2018 | March et al. |
| 9,980,984 | B2 | 5/2018 | Pettine |
| 10,456,425 | B2 | 10/2019 | Herrera Sanchez et al. |
| 10,744,160 | B2 | 8/2020 | Sokolov et al. |
| 10,881,693 | B2 | 1/2021 | Alford |
| 11,376,283 | B2 | 7/2022 | Sokolov et al. |
| 11,529,306 | B2 | 12/2022 | Yi et al. |
| 12,213,995 | B2 * | 2/2025 | Pettine ................... A61K 35/28 |
| 12,233,092 | B2 | 2/2025 | Aricha et al. |
| 2004/0248970 | A1 | 12/2004 | Webster et al. |
| 2007/0254827 | A1 | 11/2007 | Sutton et al. |
| 2008/0241112 | A1 | 10/2008 | Westenfelder |
| 2009/0177487 | A1 | 7/2009 | Eerkes |
| 2010/0178274 | A1 | 7/2010 | Sekiya et al. |
| 2011/0003008 | A1 | 1/2011 | Lim |
| 2011/0014251 | A1 | 1/2011 | Ray |
| 2012/0064049 | A1 | 3/2012 | Hunziker |
| 2013/0115198 | A1 | 5/2013 | Hoffmann et al. |
| 2013/0129688 | A1 | 5/2013 | Brenner et al. |
| 2013/0195899 | A1 | 8/2013 | Ichim et al. |
| 2013/0210725 | A1 | 8/2013 | Naughton et al. |
| 2013/0236427 | A1 | 9/2013 | Pernock |
| 2014/0004601 | A1 | 1/2014 | Lim |
| 2014/0065240 | A1 | 3/2014 | Mitsialis et al. |
| 2014/0220053 | A1 | 8/2014 | Muraca et al. |
| 2015/0086513 | A1 | 3/2015 | Savkovic et al. |

(Continued)

FOREIGN PATENT DOCUMENTS

| | | |
|---|---|---|
| AU | 2004203482 A1 | 8/2004 |
| CA | 2880404 A1 | 2/2014 |

(Continued)

OTHER PUBLICATIONS

360 Health Alert Newsletter: 2023 Research: Advanced use of Extracellular Vesicles for Today's Top Chronic Disorders (2023).
Aatonen, Maria. et al. Isolation and Characterization of Platelet-derived Extracellular Vesicles. Journal of Extracellular Vesicles 3:1-15 (2014).
Abraham et al.: Mesenchymal stem cell-derived extracellular vesicles for the treatment of acute respiratory distress syndrome. Stem Cells Transl Med. 9(1):28-38 (2019).
Alam et al., An osteopontin-derived peptide inhibits human hair growth at least in part by decreasing fibroblast growth factor-7 production in outer root sheath keratinocytes. Br J Dermatol 182(6):1404-1414 (2020).

(Continued)

*Primary Examiner* — J. E. Angell
(74) *Attorney, Agent, or Firm* — Wilson Sonsini Goodrich & Rosati

(57) ABSTRACT

Disclosed herein are compositions comprising a mesenchymal stem cell (MSC) preparation and one or more biomolecules and the use of said compositions for the treatment or a microbial infection or the symptoms or secondary pathological conditions associated with said infection.

17 Claims, 9 Drawing Sheets

(56) References Cited

U.S. PATENT DOCUMENTS

| | | |
|---|---|---|
| 2015/0125950 A1 | 5/2015 | Lim et al. |
| 2016/0113967 A1 | 4/2016 | Hedrick et al. |
| 2016/0263160 A1 | 9/2016 | Nolta et al. |
| 2016/0281045 A1 | 9/2016 | McCALL et al. |
| 2017/0051359 A1 | 2/2017 | Pegtel et al. |
| 2017/0055561 A1 | 3/2017 | Naughton et al. |
| 2017/0107488 A1 | 4/2017 | Petcavich |
| 2017/0166864 A1 | 6/2017 | Kihm et al. |
| 2017/0189449 A1 | 7/2017 | Lim |
| 2017/0304368 A1 | 10/2017 | Marban et al. |
| 2018/0100149 A1 | 4/2018 | Marbán et al. |
| 2018/0214489 A1 | 8/2018 | Riordan |
| 2018/0242590 A1 | 8/2018 | Friedman |
| 2018/0264043 A1 | 9/2018 | Pettine et al. |
| 2018/0282762 A1 | 10/2018 | Gori |
| 2018/0318356 A1 | 11/2018 | Pettine et al. |
| 2018/0338866 A1 | 11/2018 | Kharazmi |
| 2019/0000886 A1 | 1/2019 | Ross |
| 2019/0015331 A1 | 1/2019 | Elliman et al. |
| 2019/0046576 A1 | 2/2019 | Gangaraju et al. |
| 2019/0133922 A1 | 5/2019 | Kang et al. |
| 2019/0195863 A1 | 6/2019 | Brivanlou et al. |
| 2019/0209665 A1 | 7/2019 | Pluchino et al. |
| 2019/0269739 A1 | 9/2019 | Brodie et al. |
| 2019/0328792 A1 | 10/2019 | Traweger et al. |
| 2019/0330594 A1 | 10/2019 | You et al. |
| 2020/0030253 A1 | 1/2020 | Kharazmi |
| 2020/0316226 A1 | 10/2020 | Marban et al. |
| 2020/0325452 A1 | 10/2020 | Alford |
| 2020/0360443 A1 | 11/2020 | Sokolov et al. |
| 2021/0000882 A1 | 1/2021 | Coronado |
| 2021/0030807 A1 | 2/2021 | Aricha et al. |
| 2021/0035368 A1 | 2/2021 | Schouela et al. |
| 2021/0038652 A1 | 2/2021 | Naughton et al. |
| 2021/0128627 A1 | 5/2021 | Aricha et al. |
| 2021/0128630 A1* | 5/2021 | Mitsialis ............ C12N 5/0662 |
| 2021/0169939 A1 | 6/2021 | Ilagan et al. |
| 2021/0196759 A1 | 7/2021 | Moseley et al. |
| 2021/0228643 A1 | 7/2021 | Bobis-Wozowicz et al. |
| 2021/0254056 A1 | 8/2021 | Liu et al. |
| 2021/0267892 A1 | 9/2021 | Machluf et al. |
| 2021/0299036 A1 | 9/2021 | Naughton |
| 2021/0348114 A1 | 11/2021 | Hudson et al. |
| 2021/0363525 A1 | 11/2021 | Saetrom et al. |
| 2021/0369617 A1 | 12/2021 | Alford |
| 2022/0000932 A1 | 1/2022 | Zhang et al. |
| 2022/0023347 A9 | 1/2022 | Mitsialis et al. |
| 2022/0079987 A1 | 3/2022 | Pettine |
| 2022/0079990 A1 | 3/2022 | Moseley et al. |
| 2022/0096560 A1 | 3/2022 | Mitsialis et al. |
| 2022/0110970 A1 | 4/2022 | Jhan et al. |
| 2022/0125848 A1 | 4/2022 | Pettine et al. |
| 2022/0136011 A1 | 5/2022 | Kalluri |
| 2022/0136053 A1 | 5/2022 | Pettine et al. |
| 2022/0151934 A1 | 5/2022 | Ridall et al. |
| 2022/0152151 A1 | 5/2022 | Pettine |
| 2022/0175843 A1 | 6/2022 | Westenfelder et al. |
| 2022/0195384 A1 | 6/2022 | Kim et al. |
| 2022/0195390 A1 | 6/2022 | Uzan et al. |
| 2022/0202871 A1 | 6/2022 | Pettine |
| 2022/0218755 A1 | 7/2022 | Ilagan et al. |
| 2022/0249699 A1 | 8/2022 | Guild et al. |
| 2022/0264872 A1 | 8/2022 | March et al. |
| 2022/0273725 A1 | 9/2022 | Ochiya |
| 2022/0387518 A1 | 12/2022 | Mishra et al. |
| 2023/0000954 A1 | 1/2023 | Alford et al. |
| 2023/0002476 A1 | 1/2023 | Alford et al. |
| 2023/0013636 A1 | 1/2023 | Kalluri |
| 2023/0105667 A1 | 4/2023 | Brodie |
| 2023/0142496 A1 | 5/2023 | Cheng |
| 2023/0143893 A1 | 5/2023 | Bird et al. |
| 2023/0159932 A1 | 5/2023 | Pettine et al. |
| 2023/0172990 A1 | 6/2023 | Ohneda et al. |
| 2023/0181649 A1 | 6/2023 | Hariri et al. |
| 2023/0190818 A1 | 6/2023 | Jurga |
| 2023/0226267 A1 | 7/2023 | Madelska |
| 2023/0248773 A1 | 8/2023 | Jurga |
| 2023/0257712 A1 | 8/2023 | Jurga |
| 2023/0310507 A1 | 10/2023 | Lebovits et al. |
| 2023/0313144 A1 | 10/2023 | Yoshimura et al. |
| 2023/0313191 A1 | 10/2023 | Hicok et al. |
| 2024/0197832 A1 | 6/2024 | Hu et al. |
| 2025/0186501 A1 | 6/2025 | Pettine et al. |

FOREIGN PATENT DOCUMENTS

| | | |
|---|---|---|
| CN | 104622904 A | 5/2015 |
| CN | 108042572 A | 5/2018 |
| CN | 108498452 A | 9/2018 |
| CN | 111150743 A | 5/2020 |
| CN | 109718392 B | 11/2021 |
| EP | 2533859 A1 | 12/2012 |
| EP | 2582791 A2 | 4/2013 |
| EP | 2687219 A1 | 1/2014 |
| EP | 2296672 B1 | 9/2015 |
| EP | 2683389 B1 | 5/2017 |
| EP | 2877187 B1 | 6/2019 |
| EP | 3492585 A1 | 6/2019 |
| EP | 3515474 A1 | 7/2019 |
| EP | 3568143 A1 | 11/2019 |
| EP | 3668319 A1 | 6/2020 |
| EP | 3672606 A1 | 7/2020 |
| EP | 3723773 A1 | 10/2020 |
| EP | 3402489 B1 | 6/2021 |
| EP | 3920889 A1 | 12/2021 |
| EP | 3952892 A1 | 2/2022 |
| EP | 4003305 A1 | 6/2022 |
| EP | 4069205 A1 | 10/2022 |
| EP | 4069826 A1 | 10/2022 |
| EP | 4132546 A2 | 2/2023 |
| EP | 4146247 A1 | 3/2023 |
| EP | 4178591 A1 | 5/2023 |
| EP | 4180050 A1 | 5/2023 |
| EP | 4181935 A1 | 5/2023 |
| JP | 2008544957 A | 12/2008 |
| JP | 2011513217 A | 4/2011 |
| JP | 2014500249 A | 1/2014 |
| JP | 2016065106 A | 4/2016 |
| JP | 2017180553 A | 10/2017 |
| JP | 2018522071 A | 8/2018 |
| JP | 2018522593 A | 8/2018 |
| JP | 2018538132 A | 12/2018 |
| JP | WO2019235362 A1 | 7/2021 |
| JP | 2022516607 A | 3/2022 |
| JP | 2024524472 A | 7/2024 |
| KR | 20180023865 A | 3/2018 |
| KR | 20180127280 A | 11/2018 |
| WO | WO-03051331 A1 | 6/2003 |
| WO | WO-2006036213 A2 | 4/2006 |
| WO | WO-2006071011 A1 | 7/2006 |
| WO | WO-2009105044 A1 | 8/2009 |
| WO | WO-2009150199 A1 | 12/2009 |
| WO | WO-2011160055 A2 | 12/2011 |
| WO | WO-2012061537 A2 | 5/2012 |
| WO | WO-2012125471 A1 | 9/2012 |
| WO | WO-2012142569 A2 | 10/2012 |
| WO | WO-2012174282 A2 | 12/2012 |
| WO | WO-2013006327 A1 | 1/2013 |
| WO | WO-2013090523 A2 | 6/2013 |
| WO | WO-2013150303 A1 | 10/2013 |
| WO | WO-2013159091 A2 | 10/2013 |
| WO | WO-2014005183 A1 | 1/2014 |
| WO | WO-2015031110 A2 | 3/2015 |
| WO | WO-2015048842 A1 | 4/2015 |
| WO | WO-2016082882 A1 | 6/2016 |
| WO | WO-2016149358 A1 | 9/2016 |
| WO | WO-2016156865 A1 | 10/2016 |
| WO | WO-2017001649 A1 | 1/2017 |
| WO | WO-2017023689 A1 | 2/2017 |
| WO | WO-2017076924 A1 | 5/2017 |
| WO | WO-2017117585 A1 | 7/2017 |
| WO | WO-2017122095 A1 | 7/2017 |
| WO | WO-2017123022 A1 | 7/2017 |
| WO | WO-2017139795 A1 | 8/2017 |

(56) References Cited

FOREIGN PATENT DOCUMENTS

| | | | |
|---|---|---|---|
| WO | WO-2017196798 A1 | 11/2017 |
| WO | WO-2017218846 A1 | 12/2017 |
| WO | WO-2018038575 A1 | 3/2018 |
| WO | WO-2018078524 A1 | 5/2018 |
| WO | WO-2018083700 A1 | 5/2018 |
| WO | WO-2018102696 A1 | 6/2018 |
| WO | WO-2018130554 A1 | 7/2018 |
| WO | WO-2018131003 A1 | 7/2018 |
| WO | WO-2018131900 A2 | 7/2018 |
| WO | WO-2018144637 A1 | 8/2018 |
| WO | WO-2018150440 A1 | 8/2018 |
| WO | WO-2018162696 A1 | 9/2018 |
| WO | WO-2018208670 A1 | 11/2018 |
| WO | WO-2018211510 A1 | 11/2018 |
| WO | WO-2018226758 A2 | 12/2018 |
| WO | WO-2019035880 A1 | 2/2019 |
| WO | WO-2019040896 A1 | 2/2019 |
| WO | WO-2019099955 A1 | 5/2019 |
| WO | WO-2019118817 A1 | 6/2019 |
| WO | WO-2019143847 A1 | 7/2019 |
| WO | WO-2019152522 A1 | 8/2019 |
| WO | WO-2019161590 A1 | 8/2019 |
| WO | WO-2019217091 A1 | 11/2019 |
| WO | WO-2019222170 A1 | 11/2019 |
| WO | WO-2019231562 A1 | 12/2019 |
| WO | WO-2019235362 A1 | 12/2019 |
| WO | WO-2020021312 A1 | 1/2020 |
| WO | WO-2020061408 A1 | 3/2020 |
| WO | WO-2020081859 A1 | 4/2020 |
| WO | WO-2020139975 A1 | 7/2020 |
| WO | WO-2020142769 A1 | 7/2020 |
| WO | WO-2020160342 A1 | 8/2020 |
| WO | WO-2020163705 A1 | 8/2020 |
| WO | WO-2020163803 A1 | 8/2020 |
| WO | WO-2020172270 A1 | 8/2020 |
| WO | WO-2020182938 A1 | 9/2020 |
| WO | WO-2020210248 A1 | 10/2020 |
| WO | WO-2020223349 A1 | 11/2020 |
| WO | WO-2020230954 A1 | 11/2020 |
| WO | WO-2020251181 A1 | 12/2020 |
| WO | WO-2020257720 A1 | 12/2020 |
| WO | WO-2021009660 A1 | 1/2021 |
| WO | WO-2021011935 A1 | 1/2021 |
| WO | WO-2021016368 A1 | 1/2021 |
| WO | WO-2021016727 A1 | 2/2021 |
| WO | WO-2021113299 A1 | 6/2021 |
| WO | WO-2021113761 A1 | 6/2021 |
| WO | WO-2021147923 A1 | 7/2021 |
| WO | WO-2021177473 A1 | 9/2021 |
| WO | WO-2021181399 A1 | 9/2021 |
| WO | WO-2021195154 A1 | 9/2021 |
| WO | WO-2021207282 A2 | 10/2021 |
| WO | WO-2021216903 A1 | 10/2021 |
| WO | WO-2021221471 A1 | 11/2021 |
| WO | WO-2021226108 A1 | 11/2021 |
| WO | WO-2021262879 A1 | 12/2021 |
| WO | WO-2022008654 A1 | 1/2022 |
| WO | WO-2022008657 A1 | 1/2022 |
| WO | WO-2022018729 A1 | 1/2022 |
| WO | WO-2022050373 A1 | 3/2022 |
| WO | WO-2022076419 A1 | 4/2022 |
| WO | WO-2022096708 A1 | 5/2022 |
| WO | WO-2022150696 A1 | 7/2022 |
| WO | WO-2022174079 A1 | 8/2022 |
| WO | WO-2022190091 A1 | 9/2022 |
| WO | WO-2022251167 A2 | 12/2022 |
| WO | WO-2022261636 A1 | 12/2022 |
| WO | WO-2022265864 A2 | 12/2022 |
| WO | WO-2022266399 A1 | 12/2022 |
| WO | WO-2023004087 A2 | 1/2023 |
| WO | WO-2023275164 A1 | 1/2023 |
| WO | WO-2023278883 A1 | 1/2023 |
| WO | WO-2023281524 A1 | 1/2023 |
| WO | WO-2023282424 A1 | 1/2023 |
| WO | WO-2023021525 A1 | 2/2023 |
| WO | WO-2023024637 A1 | 3/2023 |
| WO | WO-2023033500 A1 | 3/2023 |
| WO | WO-2023064555 A1 | 4/2023 |
| WO | WO-2023075557 A1 | 5/2023 |
| WO | WO-2023082012 A1 | 5/2023 |
| WO | WO-2023091904 A1 | 5/2023 |
| WO | WO-2023123216 A1 | 7/2023 |
| WO | WO-2023127645 A1 | 7/2023 |
| WO | WO-2023192916 A2 | 10/2023 |
| WO | WO-2024192119 A1 | 9/2024 |
| WO | WO-2024254459 A2 | 12/2024 |
| WO | WO-2024254540 A2 | 12/2024 |
| WO | WO-2025101653 A1 | 5/2025 |
| WO | WO-2025101658 A1 | 5/2025 |
| WO | WO-2025101659 A1 | 5/2025 |
| WO | WO-2025101663 A1 | 5/2025 |
| WO | WO-2025189128 A1 | 9/2025 |
| WO | WO-2025199333 A1 | 9/2025 |
| WO | WO-2025226276 A1 | 10/2025 |
| WO | WO-2025226863 A1 | 10/2025 |
| WO | WO-2025226866 A1 | 10/2025 |

OTHER PUBLICATIONS

Attur, Mukundan. et al. Interleukin 1 receptor antagonist (IL1RN) gene variants predict radiographic severity of knee osteoarthritis and risk of incident disease. Annals of the rheumatic diseases 79(3):400-407 (2020). Published online Dec. 18, 2019.

AU2019416339 Examination Report dated Sep. 16, 2024.

Australian Examination Report No. 2 for standard patent application No. 2021261384 dated Mar. 27, 2025.

Aversa et al., Platelet-derived growth factor (PDGF) and PDGF receptors in rat corpus cavernosum: changes in expression after transient in vivo hypoxia. J Endocrinol. 170(2):395-402 (2001).

Baberg, Falk. et al. Secretome analysis of human bone marrow derived mesenchymal stromal cells. Biochimica et Biophysica Acta (BBA)-Proteins and Proteomics 1867(4):434-441 (2019).

Backlund, Lena. et al. Cognitive manic symptoms associated with the P2RX7 gene in bipolar disorder. Bipolar disorders 13(5-6):500-508 (2011).

Bagshawe, K. D., et al. A cytotoxic agent can be generated selectively at cancer sites. British Journal of Cancer 58(6):700-703 (1988).

Bagshawe, K. D. Towards generating cytotoxic agents at cancer sites. The First Bagshawe Lecture. Br. J. Cancer 60:275-281 (1989).

Ball et al., Arthroscopic treatment of post-traumatic elbow contracture. Journal of Shoulder and Elbow Surgery 11(6):624-629 (2002).

Bari et al.: Mesenchymal Stromal Cell Secretome for Severe COVID-19 Infections: Premises for the Therapeutic Use. Cells. 9(924):1-5 (2020).

Barnett, J H, and J W Smoller. The genetics of bipolar disorder. Neuroscience 164(1):331-343 (2009).

Bassir, Seyed Hossein. et al. Potential for Stem Cell-based Periodontal Therapy. Journal of Cellular Physiology 231(1):50-61 (2016).

Batch et al., Identification and localization of insulin-like growth factor-binding protein (IGFBP) messenger RNAs in human hair follicle dermal papilla. J Invest Dermatol. 106(3):471-475 (1996).

Battelli et al., T lymphocyte killing by a xanthine-oxidase-containing immunotoxin. Cancer Immunology, Immunotherapy 35(6):421-425 (1992).

Beitzel et al., The future role of mesenchymal stem cells in the management of shoulder disorders. Arthroscopy 29(10):1702-1711 (2013).

Bender et al.: Intra-Articular Injection of an Extracellular Vesicle Isolate to Treat Shoulder Osteoarthritis in an Athlete. J Regen Biol Med. 2(1):1-6 (2020).

Bender et al.: Treatment of Elbow Arthritis with a Bone Marrow derived Mesenchymal Stem Cell Extracellular Vesicle Isolate Product. J Orthop Study Sports Med. 1(1):1-6 (2021).

Bertolini et al., Abnormal interactions between perifollicular mast cells and CD8+ T-cells may contribute to the pathogenesis of alopecia areata. PLoS ONE. 9:e94260 (2014).

(56) References Cited

OTHER PUBLICATIONS

Bisaga et al., The use of mesenchymal stem cells in optic nerve atrophy in patients with multiple sclerosis: a pilot study. Annals of Clinical and Experimental Neurology 11(2):201 [2201] (2017).

Biswas et al., Primary and secondary arthritis of the elbow. Arthritis. 2013, May 27, 2013.

Black et al., Effect of adipose-derived mesenchymal stem and regenerative cells on lameness in dogs with chronic osteoarthritis of the coxofemoral joints: a randomized, double-blinded, multicenter, controlled trial. Vet Ther 8:272-284 (2007).

Black et al., Effect of intraarticular injection of autologous adipose-derived mesenchymal stem and regenerative cells on clinical signs of chronic osteoarthritis of the elbow joint in dogs. Vet Ther. 9:192-200 (2008).

Bligh, Richard, and Robert Besancenez. Safety and Efficacy of Bone Marrow Mesenchymal Stem Cell Extracellular Vesicles in Long COVID Patients: A Case Series. Journal of Stem Cells Research Development & Therapy 10(1):1000112, 1-8 (2024).

Bligh: Treatment of Idiopathic Pulmonary Fibrosis With an Extracellular Vesicle Isolate Product. International Journal of Science and Research Archive. 02(02):231-236 (2021).

Blood and Marrow Stem Cell Transplantation. Leukemia & Lymphoma Society Retrieved from Internet URL: http://www.lls.org/resource-center/download-or-order-free-publications. Accessed on Jul. 8, 2016.

Boraschi CA, IL-18 in autoimmunity: review. Eur Cytokine Netw. 17:224-252 (2006).

Botchkarev et al., Edar signaling in the control of hair follicle development. J Investig Dermatol Symp Proc. 10(3):247-251 (2005).

BR2021012661 Office Action dated Sep. 3, 2024, and a partial English translation.

Bracho-Sanchez, Evelyn. et al. Suppression of local inflammation via galectin-anchored indoleamine 2, 3-dioxygenase. Nature biomedical engineering 7(9):1156-1169 (2023).

Brigham et al. Expression of a prokaryotic gene in cultured lung endothelial cells after lipofection with a plasmid vector. Am. J. Resp. Cell. Mol. Biol. 1:95-100 (1989).

Brown et al., Molecular and cellular mechanisms of receptor-mediated endocytosis. DNA and Cell Biology 10(6):399-409 (1991).

Bruno, Stefania. et al. Mesenchymal stem cell-derived microvesicles protect against acute tubular injury. Journal of the American Society of Nephrology 20(5):1053-1067 (2009).

Budhiparama, Nicolaas C. et al. The role of genetic polymorphisms of interleukin-1 (IL-1R1 and IL-1RN) in primary knee osteoarthritis in Indonesia. Scientific reports 13(1):7967, 1-10 (2023).

Burian, Egon. et al. Effect of hypoxia on the proliferation of porcine bone marrow-derived mesenchymal stem cells and adipose-derived mesenchymal stem cells in 2- and 3-dimensional culture. Journal of cranio-maxillo-facial surgery45(3):414-419 (2017). Published online Dec. 20, 2016.

Burnett et al., GGF2 is neuroprotective in a rat model of cavernous nerve injury-induced erectile dysfunction. J Sex Med. 12(4):897-905 (2015).

Bustos, Martha L. et al. Activation of human mesenchymal stem cells impacts their therapeutic abilities in lung injury by increasing interleukin (IL)-10 and IL-1RN levels. Stem cells translational medicine 2(11):884-895 (2013).

Cabana: An Update on Exosomes. Aesthetic Authority. Technology Pipeline: Aestic Authority 2(1):22 (2020) https://www.dermatologytimes.com/view/an-update-on-exosomes.

Cai et al., Suppression of hepatocyte growth factor production impairs the ability of adipose-derived stem cells to promote ischemic tissue revascularization. Stem Cells 25(12):3234-3243 (2007).

Cai, L. et al. A slow release formulation of insulin as a treatment for osteoarthritis. Osteoarthritis and Cartilage 10(9):692-706 (2002).

Cai, Yu. et al. Anti-inflammatory and chondroprotective effects of platelet-derived growth factor-BB on osteoarthritis rat models. The Journals of Gerontology: Series A 78(1):51-59 (2023).

Caplan et al., Mesenchymal stem cells as trophic mediators. J Cell Biochem 98:1076-1084 (2006).

Caplan et al., The MSC: an injury drugstore. Cell Stem Cell 9(1):11-5 (2011).

Carneiro et al., Emerging role for TNF-a in erectile dysfunction. J Sex Med. 7(12):3823-3834 (2010).

Celik et al., Genetic analysis of interleukin 18 gene polymorphisms in alopecia areata. J Clin Lab Anal. 32(5):e22386 (2018).

Centeno: Exosomes, Mary Kaye, and Pink Caddys (2019) https://regenexx.com/blog/direct-biologics-exosomes/.

Centers for Disease Control and Prevention (CDC) Prevalence and most common causes of disability among adults—United States, 2005. Morbidity and Mortality Weekly Report 58(16):421-426 (2009).

Chang et al., Exosomes and stem cells in degenerative disease diagnosis and therapy. Cell Transplantation 27(3):349-363 (2018).

Chang et al., Tissue engineering based cartilage repair with mesenchymal stem cells in a porcine model. J Orthop Res 29:1874-1880 (2011).

Chen et al., Regenerative hair waves in aging mice and extra-follicular modulators follistatin, dkkl, and sfrp4. J Invest Dermatol. 134(8):2086-2096 (2014).

Chen, Lei. et al. Pre-vascularization Enhances Therapeutic Effects of Human Mesenchymal Stem Cell Sheets in Full Thickness Skin Wound Repair. Theranostics 7(1):117-131 (2017).

Chen, Liwen. et al. Paracrine factors of mesenchymal stem cells recruit macrophages and endothelial lineage cells and enhance wound healing. PloS one 3(4):e1886, 1-12 (2008).

Cheng, Daye. et al. The relationship between interleukin-18 polymorphisms and allergic disease: a meta-analysis. BioMed Research International 2014(1):290687, 1-11 (2014).

Cheng et al., Focus on mesenchymal stem cell-derived exosomes: opportunities and challenges in cell-free therapy. Stem Cells Int. 2017:6305295 (2017).

Chew et al., Mesenchymal stem cell exosomes enhance periodontal ligament cell functions and promote periodontal regeneration. Acta Biomater 15:89:252-264 (2019).

Chew et al., Mesenchymal stem cells in human meniscal regeneration: a systemic review. Ann Med Surg. 24:3-7 (2017).

Chia, Shi-Lu. et al. Fibroblast growth factor 2 is an intrinsic chondroprotective agent that suppresses ADAMTS-5 and delays cartilage degradation in murine osteoarthritis. Arthritis & rheumatism: official Journal of the American College of rheumatology 60(7):2019-2027 (2009).

Chinese Clinical Trial Registry ChiCTR2000030261. A Study for the key technology of mesenchymal stem cells exosomes atomization in the treatment of novel coronavirus phnumonia (COVID019). Record Version as of Feb. 26, 2020.

Choi et al., Exosomes secreted by human adipose-derived stem cells regulate the expression of collagen synthesis-related genes in human dermal fibroblasts. Abstract Book: ISEV2017, Journal of Extracellular Vesicles 6:supl:1310414; PF11.07; 141-141 (2017).

Ciavarella, Sabino. et al. A peculiar molecular profile of umbilical cord-mesenchymal stromal cells drives their inhibitory effects on multiple myeloma cell growth and tumor progression. Stem cells and development 24(12):1457-1470 (2015).

Clinical Trial No. NCT04493242. Extracellular Vesicle Infusion Treatment for COVID-19 Associated ARDS. https://clinicaltrials.gov/study/NCT04493242 (Jul. 29, 2020).

Clinical Trial No. NCT04657458. Expanded Access for Use of bmMSC-Derived Extracellular Vesicles in Patients With COVID-19 Associated ARDS. https://clinicaltrials.gov/study/NCT04657458 (Dec. 7, 2020).

Clinical Trial No. NCT05116761. ExoFlo™ Infusion for Post-Acute COVID-19 and Chronic Post-COVID-19 Syndrome. https://clinicaltrials.gov/study/NCT05116761 (Nov. 9, 2021).

Clinical Trial No. NCT05125562. Extracellular Vesicles Infusion Treatment for Mild-to-Moderate COVID-19. https://clinicaltrials.gov/study/NCT05125562 (Nov. 16, 2021).

Clinical Trial No. NCT05127122. Bone Marrow Mesenchymal Stem Cell Derived Extracellular Vesicles Infusion Treatment for ARDS. https://clinicaltrials.gov/study/NCT05127122 (Nov. 9, 2021).

Clinical Trial No. NCT05130983. Study of ExoFlo for the Treatment of Medically Refractory Crohn's Disease. https://clinicaltrials.gov/study/NCT05130983 (Nov. 16, 2021).

(56)                References Cited

OTHER PUBLICATIONS

Clinical Trial No. NCT05176366. Study of ExoFlo for the Treatment of Medically Refractory Ulcerative Colitis. https://clinicaltrials.gov/study/NCT05176366 (Dec. 14, 2021).

Clinical Trial No. NCT05215288. Expanded Access for Use of ExoFlo in Abdominal Solid Organ Transplant Patients https://clinicaltrials.gov/study/NCT05215288 (Jan. 18, 2022).

Clinical Trial No. NCT05354141. Extracellular Vesicle Treatment for Acute Respiratory Distress Syndrome (ARDS) (Extinguish ARDS). https://clinicaltrials.gov/study/NCT05354141 (Apr. 22, 2022).

Clinical Trial No. NCT05836883. Study of ExoFlo for the Treatment of Perianal Fistulas. https://clinicaltrials.gov/study/NCT05836883 (Apr. 19, 2023).

Conese et al.: Paracrine Effects and Heterogeneity of Marrow-Derived Stem/Progenitor Cells: Relevance for the Treatment of Respiratory Diseases. Cells Tissues Organs. 197:445-473 (2013).

Cook, Andrew D. et al. Granulocyte-macrophage colony-stimulating factor is a key mediator in experimental osteoarthritis pain and disease development. Arthritis research & therapy 14(5):R199, 1-9 (2012).

Co-pending Appl. Serial No. PCT/US2019/026595 Application as filed Apr. 9, 2019.

Co-pending Appl. Serial No. PCT/US2019/068615 Application as filed Dec. 26, 2019.

Co-pending Appl. Serial No. PCT/US2020/012359 Application as filed Jan. 6, 2020.

Co-pending Appl. Serial No. PCT/US2020/015982 Application as filed Jan. 30, 2020.

Co-pending Appl. Serial No. PCT/US2020/017341 Application as filed Feb. 7, 2020.

Co-pending Appl. Serial No. PCT/US2020/018821 Application as filed Feb. 19, 2020.

Co-pending Appl. Serial No. PCT/US2020/030476 Application as filed Apr. 29, 2020.

Co-pending Appl. Serial No. PCT/US2020/042762 Application as filed Jul. 20, 2020.

Co-pending Appl. Serial No. PCT/US2021/028686 Application as filed Apr. 22, 2021.

Co-pending Appl. Serial No. PCT/US2023/065115 Application as filed Mar. 29, 2023.

Co-pending Appl. Serial No. PCT/US2024/019725 Application as filed Mar. 13, 2024.

Co-pending Appl. Serial No. PCT/US2024/026444 Application as filed Apr. 26, 2024.

Co-pending Appl. Serial No. PCT/US2024/033022 Application as filed Jun. 7, 2024.

Co-pending Appl. Serial No. PCT/US2024/033123 Application as filed Jun. 7, 2024.

Co-pending U.S. Appl. No. 17/059,874 Claims as of May 7, 2024.

Co-pending U.S. Appl. No. 17/418,342 Claims as of May 21, 2024.

Co-pending U.S. Appl. No. 17/420,500 Claims as of Jun. 13, 2024.

Co-pending U.S. Appl. No. 17/427,192 Claims as of Jun. 13, 2024.

Co-pending U.S. Appl. No. 17/429,553 Claims as of Aug. 9, 2021.

Co-pending U.S. Appl. No. 17/432,138 Claims as of Aug. 19, 2021.

Co-pending U.S. Appl. No. 17/606,514 Claims as of Oct. 26, 2021.

Co-pending U.S. Appl. No. 17/628,011 Claims as of Jan. 18, 2022.

Co-pending U.S. Appl. No. 17/920,997 Claims as of Oct. 24, 2022.

Co-pending U.S. Appl. No. 18/192,593 Claims as of Jun. 7, 2023.

Cosenza, et al. Mesenchymal stem cells derived exosomes and microparticles protect cartilage and bone from degradation in osteoarthritis. Sci Rep 7(1):16214, 1-12 (2017).

Crose et al.: Bone marrow mesenchymal stem cell-derived extracellular vesicle infusion for amyotrophic lateral sclerosis. Neurodegenerative Disease Management, 1-7 (2024).

Crose, Joshua J: Treating amyotrophic lateral sclerosis with a bone marrow derived mesenchymal stem cell extracellular vesicles. A case report. International Journal of Science and Research Archive. 02(02):167-171 (2021).

Cui et al.: Plant extracellular vesicles. Protoplasma. 1-10 (2019).

Cunningham et al., The therapeutic potential of the mesenchymal stem cell secretome in ischaemic stroke. J Cereb Blood Flow Metab. 38(8):1276-1292 (2018).

Dankbar, Berno. et al. Hepatocyte growth factor induction of macrophage chemoattractant protein-1 and osteophyte-inducing factors in osteoarthritis. Journal of orthopaedic research 25(5):569-577 (2007).

Database WPI Week 201851 Thomson Scientific, London, GB; AN 2018-41069T XP002807292, & CN 108 042 572 A (Beijing Doing Time Translational Medicin) May 18, 2018.

Database WPI Week 201877 Thomson Scientific, London, GB; AN 2018-724966 XP002807291, & CN 108 498 452 A (Univ Shanghai Second Med Renji Hospital) Sep. 7, 2018.

De Boeck, Astrid. et al. Bone marrow-derived mesenchymal stem cells promote colorectal cancer progression through paracrine neuregulin 1/HER3 signalling. Gut 62(4):550-560 (2013). Online Published Apr. 25, 2012.

DeJong et al.: Extracellular vesicles: potential roles in regenerative medicine. Frontiers in Immunology. 5:608 (2014).

Direct Biologics, LLC Announces the Launch of ExoFlo Exosomes. Press Release (2019).

Direct Biologics Received FDA Approval to Initiate 'Exit-COVID-19,' a Phase II Investigational New Drug Trial. (2020).

Dong, Liang. et al. Treatment of MSCs with Wnt1a-conditioned medium activates DP cells and promotes hair follicle regrowth. Scientific Reports 4(1):5432, 1-9 (2014).

Dordevic et al., Intra-articular injection of an extracellular vesicle isolate product to treat hip labral tears. Journal of Regenerative Biology and Medicine 11:1-6 (2019).

Drela, Katarzyna. et al. Low oxygen atmosphere facilitates proliferation and maintains undifferentiated state of umbilical cord mesenchymal stem cells in an hypoxia inducible factor-dependent manner. Cytotherapy 16(7):881-892 (2014).

Dreschnack, Paul A, and Ina Belshaku. Treatment of Idiopathic Facial Paralysis (Bell's Palsy) and Secondary Facial Paralysis With Extracellular Vesicles: a Pilot Safety Study. BMC Neurology 23(1):342, 1-9 (2023).

Dwyer et al., The acetabular labrum regulates fluid circulation of the hip joint during functional activities. Am J Sports Med. 42(4):812-819 (2014).

East et al.: Can IV Infusions of Bone Marrow Derived Mesenchymal Stem Cell Extracellular Vesicles be The Fountain of Youth? Journal of Regenerative Biology and Medicine. 1(2):1-10 (2019).

East et al.: Intra-Articular Injection of an Extracellular Vesicle Isolate Product to Treat Hip Labral Tears. Journal of Regenerative Biology and Medicine. J Regen Biol Med. 2019;1(1):1-6 (2019).

East et al.: Intra-Articular Injection of an Extracellular Vesicle Isolate Product to Treat Knee Osteoarthritis in an Athlete. Journal of Biomedical Research and Clinical Investigation. 1(1):1005 (2020).

East et al.: IRB Approved Pilot Safety Study of an Extracellular Vesicle Isolate Product Evaluating the Treatment of Osteoarthritis in Combat-Related Injuries. Stem Cell Res. 1(2)-11 (2020).

East et al.: Pilot Safety Study of an Extracellular Vesicle Isolate Product for Treatment of Osteoarthritis in Combat-Related Injuries: One Year Follow Up. Genesis-JSCR-2(2)-21:1-10 (2021).

East et al.: The Safety Profile of a Bone Marrow-Derived Mesenchymal Stem Cell Extracellular Vesicle Isolate Product. J of Stem Cell Research. 6:026 (2020).

EP19812212.9 Extended European Search Report dated Mar. 16, 2022.

EP19906384.3 Extended European Search Report dated Aug. 29, 2022.

EP20758516.7 Exam Report dated Mar. 15, 2024.

EP21793396.9 Extended European Search Report dated Mar. 28, 2024.

Epifanova et al., [Investigation of mechanisms of action of growth factors of autologous platelet-rich plasma used to treat erectile dysfunction]. Urologiia. Sep. 2017;(4):46-48 (2017) Russian. English Abstract Provided.

Erhardt et al., Association of polymorphisms in P2RX7 and CaMKKb with anxiety disorders. Journal of Affective Disorders 101(1-3):159-168 (2007).

(56)            References Cited

OTHER PUBLICATIONS

Fan et al., Synovium-derived mesenchymal stem cells: a new source for musculoskeletal regeneration. Tissue Engineering Part B Review 15(1):75-86 (2009).

Federal Register. vol. 76, No. 27 (2011): p. 7166.

Felgner, Philip L, et al., Lipofection: A Highly Efficient, Lipid-Mediated DNA-Transfection Procedure. Proceedings of the National Academy of Sciences of the United States of America 84(21):7413-7417 (1987).

Feng et al. Transplantation of mesenchymal stem cells and nucleus pulposus cells in a degenerative disc model in rabbits: a comparison of 2 cell types as potential candidates for disc regeneration. J Neurosurgery Spine 14:322-329 (2011).

Ferrone et al.: Handbook of Monoclonal Antibodies. Noges Publications 22:303-357 (1985).

Fouad et al., Interleukin-18 gene polymorphisms in systemic lupus erythematosus: relation to disease status. Egypt J Immunol. 21:1-12 (2014).

François, Moïra. et al. Human MSC suppression correlates with cytokine induction of indoleamine 2, 3-dioxygenase and bystander M2 macrophage differentiation. Molecular therapy 20(1):187-195 (2012).

Freitag et al., Mesenchymal stem cell therapy in the treatment of Osteoarthritis: reparative pathways, safety, and efficacy: a review. BMC Musculoskeletal Disorders 17:230 (2016).

Frisbie et al., Clinical update on the use of mesenchymal stem cells in equine orthopaedics. Equine Veterinary Journal, 42:86-89 (2010).

Fu, H et al., Identification of human fetal liver miRNAs by a novel method. FEBS letters 579(17):3849-3854 (2005).

Gao, Lei. et al. Association of endothelial nitric oxide synthase polymorphisms with an increased risk of erectile dysfunction. Asian journal of andrology 19(3):330-337 (2017).

Gennaro, Alfonso R. Remington: The Science And Practice of Pharmacy, 19th Edition. Mack Publishing Company :1-6 (1995).

Gennaro, A.R., Remington: The science and practice of pharmacy. 19th edition. 1995. 12 Pages.

Gilhar A. Collapse of immune privilege in alopecia areata: coincidental or substantial? J Invest Dermatol. 130(11):2535-2537 (2010).

Giugliano et al., Erectile dysfunction associates with endothelial dysfunction and raised proinflammatory cytokine levels in obese men. J Endocrinol Invest. 27(7):665-669 (2004).

Guerico et al., Production of canine mesenchymal stem cells from adipose tissue and their application in dogs with chronic osteoarthritis of the humeroradial joints. Cell Biol Int 36:189-194 (2012).

Guo et al., Exosomes derived from platelet-rich plasma promote the re-epithelization of chronic cutaneous wounds via activation of YAP in a diabetic rat model. Theranostics 7(1):81-96 (2017).

Haber et al.: Biologic Effects of Specific Antibodies in Reversing the Pharmacologic and Toxic Effects of Digoxin. Raven Press 365-389(1977).

Hamilton, John L. et al. Targeting VEGF and Its Receptors for the Treatment of Osteoarthritis and Associated Pain. Journal of bone and mineral research : the official journal of the American Society for Bone and Mineral Research 31(5):911-924 (2016).

Handayani, Erika Yusticia, and Heri Krisnata Ginting. Osteoarthritis and Hypothyroidism: What's the Association? A Literature Review. Asian Journal of Healthy and Science 3(6):113-119 (2024).

Hara, Tomonori. et al. Genetics of bipolar disorder: insights into its complex architecture and biology from common and rare variants. Journal of human genetics 68(3):183-191 (2023). Published online May 26, 2022.

Harris JD. Hip labral repair: options and outcomes. Curr Rev Musculoskelet Med. 9(4):361-367 (2016).

Haynesworth, Stephen E. et al. Cytokine expression by human marrow-derived mesenchymal progenitor cells in vitro: Effects of dexamethasone and IL-1α. Journal of cellular physiology 166(3):585-592 (1996).

Hazehara-Kunitomo, Yuri. et al. Acidic Pre-conditioning Enhances the Stem Cell Phenotype of Human Bone Marrow Stem/progenitor Cells. International Journal of Molecular Sciences 20(5):1097, 1-10 (2019).

Heijnen, Harry F. et al. Activated Platelets Release Two Types of Membrane Vesicles Microvesicles by Surface Shedding and Exosomes Derived From Exocytosis of Multivesicular Bodies and Alpha-granules. Blood 94(11)3791-3799 (1999).

Hessvik et al.: Current knowledge on exosome biogenesis and release description. Cell. Mol. Life Sci. 75:193-208 (2018).

Hicok et al.: Exosome Origins: Why the Cell Source Matters. Stem Cells Regen Med. 4(1):1-4 (2020).

Hiyama et al., Transplantation of mesenchymal stem cells in a canine disc degeneration model. J Orthop Res 26:589-600 (2008).

Ho, Chih-Yi. et al. Clinical and genetic aspects of alopecia areata: a cutting edge review. Genes 14(7):1362, 1-20 (2023).

Hotaling et al., DCCT/EDIC Research Group. Pilot genome-wide association search identifies potential loci for risk of erectile dysfunction in type 1 diabetes using the DCCT/EDIC study cohort. J Urol. 188(2):514-520 (2012).

Hou, Chun et al., Expression of matrix metalloproteinases and tissue inhibitor of matrix metalloproteinases in the hair cycle. Exp Ther Med. 12(1):231-237 (2016).

Howe et al.: The miracle of stem cells. Stemedica Cell Technologies, Inc. 202-210 (2011).

Howe et al., The miracle of stem cells. Stemedica Cell Technologies pp. 202-210 (2011).

Howell, T. Howard. et al. A Phase I/II Clinical Trial to Evaluate a Combination of Recombinant Human Platelet-derived Growth Factor-BB and Recombinant Human Insulin-like Growth Factor-I in Patients with Periodontal Disease. Journal of Periodontology 68(12):1186-1193 (1997).

Hughes et al., Monoclonal antibody targeting of liposomes to mouse lung in vivo. Cancer Research 49(22):6214-6220 (1989).

IL284377 Office Action dated Nov. 2, 2023.

Istanbul Med Assist further considers whether exosomes work for hair loss (IMA) https://www.istanbulmedassist.com/blog/do-exosomes-really-work-for-hair-loss/#:~:text=Do%20Exosomes%20Actually%20Work?,%2C%20and%20overall%20health (2024).

Jacob et al., Association of the oxytocin receptor gene (OXTR) in caucasian children and adolescents with autism. Neuroscience Letters 417(1):6-9 (2007).

Jaeger et al., "Improved predictions of secondary structures for RNA", Proceedings of the National Academy of Sciences, vol. 86, No. 20, Oct. 1, 1989, pp. 7706-7710.

Jaeger, John A, et al., [17] Predicting optimal and suboptimal secondary structure for RNA. Methods in Enzymology 183:281-306 (1989).

Japanese Application No. 2021-537063 Office Action dated Dec. 15, 2023.

Japanese Application No. 2021-564403 Office Action dated May 30, 2024.

Johnston et al., A point mutation in PDGFRB causes autosomal-dominant Penttinen syndrome. Am J Hum Genet. 97(3):465-474 (2015).

Jorgenson, Eric. et al. Genetic variation in the SIM1 locus is associated with erectile dysfunction. Proceedings of the National Academy of Sciences 115(43):11018-11023 (2018).

JP2021-517548 Office Action dated Apr. 4, 2023.

JP2021544344 Office Action dated Dec. 12, 2023, and an English translation.

JP2021546214 Office Action dated Dec. 19, 2023, and a partial English translation.

JP2021-564403 Office Action dated Apr. 2, 2025, and an English translation.

Julianto et al., Topical delivery of mesenchymal stem cells "secretomes" in wound repair. Acta Med Indones 48(3):217-220 (2016).

Kambur et al., Genetic variation in P2RX7 and pain tolerance. Pain 159(6):1064-1073 (2018).

Kandola et al., How does rheumatoid arthritis affect the wrists? Medical News Today https://www.medicalnewstoday.com/articles/323056 (2018).

(56)          References Cited

OTHER PUBLICATIONS

Kavoussi et al., Recombinant PAI-1 therapy restores myoendothelial junctions and erectile function in PAI-1-deficient mice. Andrologia 47(10):1147-1152 (2015).

Kawabe et al., Localization of TIMP in cycling mouse hair. Development 111(4):877-879 (1991).

Kellgren et al., Radiological assessment of osteo-arthrosis. Ann Rheum Dis Dec. 16(4):494-502 (1957).

Kelly et al., Arthroscopic debridement without radial head excision of the osteoarthritic elbow. Arthroscopy 23(2):151-156 (2007).

Kiener, Hans P. et al. Tumor necrosis factor a promotes the expression of stem cell factor in synovial fibroblasts and their capacity to induce mast cell chemotaxis. Arthritis & Rheumatism: Official Journal of the American College of Rheumatology 43(1):164-174 (2000).

Kim et al., Association between interleukin 18 polymorphisms and alopecia areata in Koreans. J Interferon Cytokine Res. 34:349-353 (2014).

Kim et al., Mesenchymal stem cells vs. mesenchymal stem cell secretome for rheumatoid arthritis treatment. JSM Arthritis, vol. 1(1):1001 (2016).

Kim et al.: Wound healing effect of adipose-derived stem cells: A critical role of secretory factors on human dermal fibroblasts. Journal of Dermatological Science. 48:15-24 (2007).

Kim, Soochong. et al. Insulin-like growth factor-1 regulates platelet activation through PI3-K alpha isoform. Blood, The Journal of the American Society of Hematology 110(13):4206-4213 (2007).

Kinane, Denis F. et al. Periodontal diseases. Nature reviews Disease primers 3:17038, 1-14 (2017).

Knights, Alexander J. et al. Synovial macrophage diversity and activation of M-CSF signaling in post-traumatic osteoarthritis. bioRxiv :1-29 (2023).

Koga et al., Synovial stem cells are regionally specified according to local microenvironments after implantation for cartilage regeneration. Stem Cells 25:689-696 (2007).

Koizumi et al., Distribution of IL-18 and IL-18 receptor in human skin: various forms of IL-18 are produced in keratinocytes. Arch Dermatol Res. 293(7):325-333 (2001).

Kondo, Ayano, and Tsuyoshi Osawa. Establishment of an Extracellular Acidic pH Culture System. Journal of Visualized Experiments 129:e56660, 1-7 (2017).

Kordelas, L. et al. MSC-derived Exosomes: A Novel Tool to Treat Therapy-refractory Graft-versus-host Disease. Leukemia 28(4):970-973 (935-979) (2014).

KR10-2022-7004073 Office Action dated Jan. 30, 2025.

Krych et al., Modest mid-term outcomes after isolated arthroscopic debridement of acetabular tears. Knee Surg Sports Traumatol Arthrosc. 22(4):763-767 (2014).

Lai et al., Androgenic alopecia is associated with less dietary soy, higher blood vanadium and rs1160312 1 polymorphism in Taiwanese communities. PLos One 8(12):e79789, 1-11 (2013).

Lankford, Karen L, et al., Intravenously Delivered Mesenchymal Stem Cell-derived Exosomes Target M2-type Macrophages In The Injured Spinal Cord. PLoS One 13(1):e0190358, 20 Pages (2018).

Lecuyer et al., Dual role of ALCAM in neuroinflammation and blood-brain barrier homeostasis. Proc Natl Acad Sci U S A. 114(4):E524-E533 (2017).

Lee et al., Injectable mesenchymal stem cell therapy for large cartilage defects—a porcine model. Stem Cells 25:2964-2971 (2007).

Letsinger, Robert. L. et al. Cholesteryl-conjugated oligonucleotides: Synthesis, properties, and activity as inhibitors of replication of human immunodeficiency virus in cell culture. Proceedings of the National Academy of Sciences of the United States of America 86(17):6553-6556 (1989).

Levitte et al.: Mesenchymal stem cell-derived extracellular vesicles for the treatment of acute rejection in pediatric and adult bowl transplant. American Journal of Transplantation. 1-4 (2023).

Li, Chengxin. et al. Association of thyroid hormone with osteoarthritis: from mendelian randomization and RNA sequencing analysis. Journal of Orthopaedic Surgery and Research 19(1):429, 1-11 (2024).

Li, et al. Emerging Role of Exosomes in the Joint Diseases. Cell Physiol Biochem 47(5):2008-2017 (2018).

Li et al.: Mesenchymal stem cells and acellular products attenuate murine induced colitis. Stem Cell Research & Therapy. 11:515 (2020).

Li et al., Six novel susceptibility loci for early-onset androgenetic alopecia and their unexpected association with common diseases. PLoS Genetics 8(5):e1002746, 1-9 (2012).

Li, Yun-Xuan. et al. FGF1 reduces cartilage injury in osteoarthritis via regulating AMPK/Nrf2 pathway. Journal of Molecular Histology 54(5):427-438 (2023).

Libro et al., Cannabidiol modulates the immunophenotype and inhibits the activation of the inflammasome in human gingival mesenchymal stem cells. Frontiers in Physiology 7:559 (2016).

Lichtenstein, A et al., Liposome-encapsulated silver sulfadiazine (SSD) for the topical treatment of infected burns: thermodynamics of drug encapsulation and kinetics of drug release. Journal of inorganic biochemistry 60(3):187-198 (1995).

Lightner, Amy L. et al. Bone Marrow Mesenchymal Stem Cell-Derived Extracellular Vesicle Infusion for the Treatment of Respiratory Failure From COVID-19: A Randomized, Placebo-Controlled Dosing Clinical Trial. Chest 164(6):1444-1453 (2023).

Lightner, Amy L. et al. Mesenchymal Stem Cell Extracellular Vesicles as a New Treatment Paradigm in Solid Abdominal Organ Transplantation: A Case Series. Stem Cells and Development. 33(5-6):107-115 (2024).

Lim et al.: Letter to the Editor re: "Exosomes Derived from Bone Marrow Mesenchymal Stem Cells as Treatment for Severe COVID-19" by Sengupta et al. Stem Cells and Development. 00(00) (2020).

Lin, Shih-Chao. et al. Microencapsulated recombinant human epidermal growth factor ameliorates osteoarthritis in a murine model. Evidence-Based Complementary and Alternative Medicine 2021(1):9163279, 1-10 (2021).

Lin, WeiYu. et al. Function of CSF1 and IL34 in Macrophage Homeostasis, Inflammation, and Cancer. Frontiers in immunology 10:2019, 1-18 (2019).

Little et al., Total elbow arthroplasty: a systematic review of the literature in the English language until the end of 2003. Journal of Bone and Joint Surgery 87(4):437-444 (2005).

Litzinger et al., Biodistribution and immunotargetability of ganglioside-stabilized dioleoylphosphatidylethanolamine liposomes. Biochimica et Biophysica Acta (BBA)-Biomembranes 1104(1):179-187 (1992).

Liu et al., Prediction of male-pattern baldness from genotypes. European Journal of Human Genetics 24:895-902 (2015).

Liu et al.: Therapeutic potential of mesenchymal stem/stromal cell-derived secretome and vesicles for lung injury and disease. Expert Op Biol Ther. 29(2):125-140 (2019).

Logozzi, Mariantonia. et al. Microenvironmental pH and Exosome Levels Interplay in Human Cancer Cell Lines of Different Histotypes. Cancers 10(10):370, 1-15 (2018).

Lou, Danning. et al. Single nucleotide polymorphisms in the non-coding region of STIM1 gene are associated with Parkinson disease risk in Chinese Han population. Medicine 99(9):e19234, 1-10 (2020).

Luo, Shi-Xing. et al. Genetic polymorphisms of interleukin-16 and risk of knee osteoarthritis. PloS one 10(5):e0123442, 1-12 (2015).

Luo, Ziwei. et al. IL16 Regulates Osteoarthritis Progression as a Target Gene of Novel-miR-81. Cartilage 15(2):175-183 (2024). Published online Apr. 21, 2023.

Mancuso et al., Mesenchymal stem cell therapy for osteoarthritis: the critical role of the cell secretome. Front Bioeng Biotechnol 7:9 [1-9] (2019).

Marcinska et al., Evaluation of DNA variants associated with androgenetic alopecia and their potential to predict male pattern baldness. PLoS One 10(5):1-18, e0127852 (2015).

Massa et al.: Clinical Applications of Mesenchymal Stem/Stromal Cell Derived Extracellular Vesicles: Therapeutic Potential of an Accellular Product. Diagnostics. 10:999 (2020).

Massicotte, F. et al. Can altered production of interleukin-1β, interleukin-6, transforming growth factor-β and prostaglandin E2 by isolated human subchondral osteoblasts identify two subgroups of osteoarthritic patients. Osteoarthritis and cartilage 10(6):491-500 (2002).

(56) References Cited

OTHER PUBLICATIONS

Massicotte, Frederic. et al. Modulation of insulin-like growth factor 1 levels in human osteoarthritic subchondral bone osteoblasts. Bone 38(3):333-341 (2006). Published online Oct. 27, 2005.

Mathieu et al.: Specificities of exosome versus small ectosome secretion revealed by live intracellular tracking of CD63 and CD9. Nat Commun. 12(4389):1-18 (2021).

Mazaheri et al., Ameliorating effect of osteopontin on H(2)O(2)-induced apoptosis of human oligodendrocyte progenitor cells. Cell Mol Neurobiol. 38(4):891-899 (2018).

McDowall et al., The role of activins and follistatins in skin and hair follicle development and function. Cytokine Growth Factor Rev. 19(5-6):415-426 (2008).

McQuillin et al., Case-control studies show that a non-conservative amino-acid change from a glutamine to arginine in the P2RX7 purinergic receptor protein is associated with both bipolar-and unipolar-affective disorders. Molecular Psychiatry 14:614-620 (2008).

Messa, Genevieve E. et al. Treatment of a Recurrent Ischial Ulcer With Injected Exosomes. Journal of Surgical Case Reports 2022(6):rjac271, 1-3 (2022).

Mokbel et al., Homing and efficacy of intra-articular injection of autologous mesenchymal stem cells in experimental chondral defects in dogs. Clin Exp Rheumatol 29:275-284 (2011).

Monsel et al.: Mesenchymal Stem Cell Derived Secretome and Extracellular Vesicles for Acute Lung Injury and Other Inflammatory Lung Diseases. Expert Opin Biol Ther. 16(7):859-871 (2016).

Muratovic, Dzenita. et al. Elevated levels of active Transforming Growth Factor β1 in the subchondral bone relate spatially to cartilage loss and impaired bone quality in human knee osteoarthritis. Osteoarthritis and cartilage 30(6):896-907 (2022).

Murphy et al., Stem cell therapy in a caprine model of osteoarthritis. Arthritis Rheum 48:3464-3474 (2003).

Nagao, Masashi. et al. Vascular endothelial growth factor in cartilage development and osteoarthritis. Scientific reports 7(1):13027, 1-16 (2017).

Nakamura, Yoshihiro. et al. Mesenchymal-stem-cell-derived exosomes accelerate skeletal muscle regeneration. FEBS letters 589(11):1257-1265 (2015).

Needleman, Saul B, and Christian D. Wunsch. A General Method Applicable to the Search for Similarities in the Amino Acid Sequence of Two Proteins. Journal of Molecular Biology 48(3):443-453 (1970).

Nguyen et al., Functional outcomes of arthroscopic capsular release of the elbow. Arthroscopy 22(8):842-849 (2006).

Ning et al., SNP@lincTFBS: an integrated database of polymorphisms in human LincRNA transcription factor binding sites. PLoS One 9(7):e103851, 1-8 (2014).

Novikov A.V. Experimental and clinical use of multipotent mesenchymal stem cells to stimulate articular cartilage regeneration. Journal of Medicine 3:125-135 (2017).

OHSU: Emergency Medicine Newsletter https://www.ohsu.edu/sites/default/files/2024-03/March%202024%20Newsletter%20%28Long%29.pdf (Mar. 2024).

Osborn et al.: A novel extracellular vesicle paradigm for the treatment of COVID-19 induced acute respiratory distress syndrome (ARDS). Respirator Medicine Case Reports. 51:102087 (2024).

Oyanguren-Desez et al., Gain-of-function of P2X7 receptor gene variants in multiple sclerosis. Cell Calcium 50(5):468-472 (2011).

Paicius, Rick. et al. Safety and Efficacy of Intravenous ExoFlo in the Treatment of Complex Regional Pain Syndrome. Pain Physician 26(7):E851-E857 (2023).

Papadopoulos, Konstantinos I. et al. Novel use of intraarticular granulocyte colony stimulating factor (hG-CSF) combined with activated autologous peripheral blood stem cells mobilized with systemic hG-CSF: safe and efficient in early osteoarthritis. Cartilage 13(1_suppl):1671S-1674S (2021).

Papathanasiou, Ioanna. et al. Bone morphogenetic protein-2-induced Wnt/β-catenin signaling pathway activation through enhanced low-density-lipoprotein receptor-related protein 5 catabolic activity contributes to hypertrophy in osteoarthritic chondrocytes. Arthritis research & therapy 14(2):R82, 1-14 (2012).

Park et al., Hair growth stimulated by conditioned medium of adipose-derived stem cells is enhanced by hypoxia: evidence of increased growth factor secretion. Biomed Res. 31(1):27-34 (2010).

Park, Hang-soo. et al. Human BM-MSC secretome enhances human granulosa cell proliferation and steroidogenesis and restores ovarian function in primary ovarian insufficiency mouse model. Scientific reports 11(1):4525, 1-12 (2021).

Partain, Brittany D. et al. Intra-articular delivery of an indoleamine 2, 3-dioxygenase galectin-3 fusion protein for osteoarthritis treatment in male Lewis rats. Arthritis Research & Therapy 25(1):173, 1-15 (2023).

Patton, Mary C. et al. Hypoxia Alters the Release and Size Distribution of Extracellular Vesicles in Pancreatic Cancer Cells to Support Their Adaptive Survival. Journal of cellular biochemistry 121(1):828-839 (2021).

PCT/US2016/022629 International Preliminary Report on Patentability dated Sep. 28, 2017.

PCT/US2016/022629 International Search Report and Written Opinion dated Aug. 25, 2016.

PCT/US2019/026595 International Preliminary Report on Patentability dated Dec. 1, 2020.

PCT/US2019/026595 International Search Report and Written Opinion dated Jul. 2, 2019.

PCT/US2019/068615 International Search Report and Written Opinion dated Mar. 26, 2020.

PCT/US2020/012359 International Search Report and Written Opinion dated Mar. 24, 2020.

PCT/US2020/015982 International Preliminary Report on Patentability dated Aug. 12, 2021.

PCT/US2020/015982 International Search Report and Written Opinion dated Apr. 24, 2020.

PCT/US2020/017341 International Search Repot and Written Opinion dated Apr. 28, 2020.

PCT/US2020/018821 International Search Report and Written Opinion dated May 21, 2020.

PCT/US2020/030476 International Search Report and Written Opinion dated Aug. 12, 2020.

PCT/US2020/042762 International Preliminary Report on Patentability dated Jan. 27, 2022.

PCT/US2020/042762 International Search Report and Written Opinion dated Dec. 10, 2020.

PCT/US2021/028686 International Search Report and Written Opinion dated Aug. 16, 2021.

PCT/US2023/065115 International Search Report and Written Opinion dated Sep. 27, 2023.

PCT/US2024/019725 International Search Report and Written Opinion dated Jun. 28, 2024.

PCT/US2024/019725 Invitation to Pay Additional Fees dated May 7, 2024.

PCT/US2024/026444 International Search Report and Written Opinion dated Jul. 15, 2024.

PCT/US2024/033022 International Search Report and Written Opinion dated Sep. 3, 2024.

PCT/US2024/033123 International Search Report and Written Opinion dated Sep. 17, 2024.

Pearson, William R, and David J. Lipman. Improved Tools for Biological Sequence Comparison. Proceedings of the National Academy of Sciences 85(8):2444-2448 (1988).

Pettine et al., Autogenous bone marrow concentrate for the treatment of osteoarthritis of the knee, hip and shoulder in former NFL players. J Stem Cell Res Ther. 4(1):9-13 (2018).

Pettine et al., Percutaneous injection of Autologous bone marrow concentrate significantly reduces lumbar discogenic pain through twelve months. Stem Cells 33:146-156 (2015).

Pettine et al., The biologic treatment of osteoarthritis with mesenchymal stem cell exosomes: the future is now. J Stem Cell Res Dev Ther. S1001:1-5 (2019).

Pettine et al., Tibial metaphyseal injection with bone marrow concentrate to treat knee arthritis. American J Stem Cell Res Ther. 2(1):5-10 (2018).

(56) References Cited

OTHER PUBLICATIONS

Pettine et al.: Treating Discogenic Pain with Mesenchymal Stem Cell Exosomes: What Is the Biologic Mechanism of Action. Jacobs Journal of Bone Marrow and Stem Cell Research. 5(1):017 (2019).

Philippon et al., The hip fluid seal-part I: the effect of an acetabularlabral tear, repair, resection, and reconstruction on hip fluid pressurization. Knee Surg Sports Traumatol Arthrosc. 22(4):722-729 (2014).

Phillips et al: One month safety study of ExoFlo injection for the treatment of lumbar or cervical radiculopathy in the epidural space. International Journal of Science and Research Archive. 119-124 eISSN:2582-8185 (2021).

Phinney et al.: MSC-Derived Exosomes for Cell-Free Therapy. Stem Cells. 35:851-858 (2017).

Pietersz et al., Antibody conjugates for the treatment of cancer. Immunological Reviews 129(1):57-80 (1992).

Pourakbari, Ramin. et al. The potential of exosomes in the therapy of the cartilage and bone complications; emphasis on osteoarthritis. Life Sciences 236:116861, 1-8 (2019).

Qi et al.: Exosomes Secreted by Human-Induced Pluripotent Stem Cell-Derived Mesenchymal Stem Cells Repair Critical-Sized Bone Defects through Enhanced Angiogenesis and Osteogenesis in Osteoporotic Rats. International Journal of Biological Sciences 12(7):836-849 (2016).

Qian et al., Vacuum therapy prevents corporeal veno-occlusive dysfunction and penile shrinkage in a cavernosal nerve injured rat model. Asian J Androl. 22(3):274-279 (2020).

Ragni, Enrico. et al. Secreted factors and extracellular vesicles account for the immunomodulatory and tissue regenerative properties of bone-marrow-derived mesenchymal stromal cells for osteoarthritis. Cells 11(21):3501, 1-21 (2022).

Rajan et al., Cannabidiol activates neuronal precursor genes in human gingival mesenchymal stromal cells. Journal of Cellular Biochemistry 118(6):1531-1546 (2016).

Rhee, Sung-Mi. et al. Injectable Tissue-engineered Soft Tissue for Tissue Augmentation. Journal of Korean Medical Science 29(Suppl3): S170-S175 (2014).

Rodriguez-Fontenla, Cristina. et al. Association of a BMP5 microsatellite with knee osteoarthritis: case-control study. Arthritis Research & Therapy 14(6):R257, 1-8 (2012).

Roffler et al., Anti-neoplastic glucuronide prodrug treatment of human tumor cells targeted with a monoclonal antibody-enzyme conjugate. Biochemical Pharmacology 42(10):2062-2065 (1991).

Rolandsson Enes, Sara. et al. Quantitative proteomic characterization of lung-MSC and bone marrow-MSC using DIA-mass spectrometry. Scientific Reports 7(1):9316, 1-12 (2017).

Roman-Blas, Jorge A. et al. Osteoarthritis associated with estrogen deficiency. Arthritis research & therapy 11(5):241, 1-14 (2009).

Romanov, Yu A. et al. Comparative Analysis of Secretome of Human Umbilical Cord- and Bone Marrow-Derived Multipotent Mesenchymal Stromal Cells. Bulletin of Experimental Biology and Medicine 166(4):535-540 (2019).

RU2021122946 Examination Report dated Sep. 16, 2024.

Russian Patent Application No. 2021-1122956 Office Action dated Jul. 6, 2023.

Russian Patent Application No. 2021122956/10 Search Report issued on Jul. 6, 2023.

Saldanha-Araujo et al.: Mesenchymal Stem Cells: A New Piece in the Puzzle of COVID-19 Treatment. Frontiers in Immunology. 11:1563. (2020).

Salisbury et al.: SNP and haplotype variation in the human genome. Mutat Res 526(1-2):53-61 (2003).

Santos et al., Three-dimensional spheroid cell culture of umbilical cord tissue-derived mesenchymal stromal cells leads to enhanced paracrine induction of wound healing. Stem Cell Res Ther. 6(1):90 (2015).

Sasaki, Gordon H. Clinical Use of Extracellular Vesicles in the Management of Male and Female Pattern Hair Loss: A Preliminary Retrospective Institutional Review Board Safety and Efficacy Study. Aesthetic Surgery Journal. Open Forum 4:ojac045, 1-15 (2022).

Savoie et al., Arthroscopic management of the arthritic elbow: indications, technique, and results. Journal of Shoulder and Elbow Surgery 8(3):214-219 (1999).

Seldes et al., Anatomy, histologic features, and vascularity of the adult acetabular labrum. Clin Orthop Relat Res 2001(382):232-240 (2001).

Sengupta et al.: Exosomes Derived from Bone Marrow Mesenchymal Stem Cells as Treatment for Severe COVID-19. Stem Cells and Development. 29(12):747-754 (2020).

Sengupta et al.: Response to Lim et al. re "Exosomes Derived from Bone Marrow Mesenchymal Stem Cells as Treatment for Severe COVID-19". Stem Cells and Development. 29(14):879-881 (2020).

Senter et al., Generation of 5-fluorouracil from 5-fluorocytosine by monoclonal antibody-cytosine deaminase conjugates. Bioconjugate Chemistry 2(6):447-451 (1991).

Senter et al., Generation of cytotoxic agents by targeted enzymes. Bioconjugate Chemistry 4(1):3-9 (1993).

Shao, Yan. et al. BMP5 silencing inhibits chondrocyte senescence and apoptosis as well as osteoarthritis progression in mice. Aging (albany NY) 13(7):9646-9664 (2021).

Sheinkop et al.: Intra-Articular Injection of an Extracellular Vesicle Isolate Product to Treat Hip Osteoarthritis. International Journal of Recent Scientific Research. 10(12A):36230-36232 (2019).

Shen et al., Four genetic variants interact to confer susceptibility to atopic dermatitis in Chinese Han population. Molecular Genetics and Genomics 290(4):1493-1498 (2015).

Shen, Jie. TGF-beta signaling and the development of osteoarthritis. Bone research 2(1):1-7 (2014).

Singaporean Application No. 11202106836U Written Opinion dated Dec. 19, 2022.

Sivalingam et al., Single-nucleotide polymorphisms of the interleukin-18 gene promoter region in rheumatoid arthritis patients: protective effect of AA genotype. Tissue Antigens 62:498-504 (2003).

Skovronova, Renata. et al. Surface marker expresion in small and medium/large mesenchymal stromal cell-derived extracellular vesicles in naive or apoptotic condition using orthogonal techniques. bioRxiv. 1-32 (2021).

Smith et al., Isolation and implantation of autologous equine mesenchymal stem cells from bone marrow into the superficial digital flexor tendon as a potential novel treatment. Equine Vet J 35(1):99-102 (2003).

Smith et al., Mesenchymal stem cell therapy in equine tendinopathy. Disabil Rehabil 30:20-22, 1752-1758 (2008).

Smith, Temple F, and Michael S. Waterman. Comparison of Biosequences. Advances in Applied Mathematics 2(4):482-489 (1981).

Spencer, Paige S, and Jose M Barral. Genetic Code Redundancy and Its Influence on the Encoded Polypeptides. Computational and Structural Biotechnology Journal 1:e201204006, 1-8 (2012).

Stevanato et al.: Investigation of Content, Stoichiometry and Transfer of miRNA from Human Neural Stem Cell Line Derived Exomes. PLoS ONE. 11(1):e0146353 (2016).

Suarez-Faritias et al., Alopecia areata profiling shows TH1, TH2, and IL-23 cytokine activation without parallel TH17/TH22 skewing. J Allergy Clin Immunol. 136(5):1277-1287 (2015).

Sugimoto, K.: Basic knowledge of ultrasonography in sports injury and trauma. Medical Technology. 43(5):440-444 (2015).

Sun, JiaYang et al. The healing effects of conditioned medium derived from mesenchymal stem cells on radiation-induced skin wounds in rats. Cell transplantation 28(1):105-115 (2019).

Talegaonkar, The Role of Human MSC Derived Exosomes in the Treatment of Periodontal Diseases, Master's Thesis (2017).

Tamama, Kenichi, and Svetoslava S Kerpedjieva. Acceleration of Wound Healing by Multiple Growth Factors and Cytokines Secreted from Multipotential Stromal Cells/Mesenchymal Stem Cells. Advances in Wound Care 1(4):177-182 (2012).

Tamimi et al., Breast cancer susceptibility loci and mammographic density. Breast Cancer Research 10:R66 [1-9] (2008).

Thelen et al., Depending on its nano spacing, ALCAM promotes cell attachment and axon growth. PLoS One 7(12):e40493 (2012).

Toh et al., Advances in mesenchymal stem cell-based strategies for cartilage repair and regeneration. Stem Cell Reviews and Reports 10(5):686-696 (2014).

(56)             References Cited

OTHER PUBLICATIONS

Toh, et al. MSC exosome as a cell-free MSC therapy for cartilage regeneration: Implications for osteoarthritis treatment. Seminars in Cell & Developmental Biology 67:56-64 (2017).

Ueshima et al.: Imaging Diagnosis of Hip Diseases-Diagnostic Imaging of Glenohumeral Labrum Injuries. MB Orthop. 26(5):191-197 (2013).

U.S. Appl. No. 17/059,874 Office Action dated Dec. 30, 2024.

U.S. Appl. No. 17/059,874 Office Action dated Jul. 11, 2024.

U.S. Appl. No. 17/059,874 Restriction Requirement dated Nov. 8, 2023.

U.S. Appl. No. 17/418,342 Office Action dated Dec. 30, 2024.

U.S. Appl. No. 17/418,342 Office Action dated Mar. 12, 2024.

U.S. Appl. No. 17/418,342 Office Action dated Sep. 5, 2024.

U.S. Appl. No. 17/420,500 Office Action dated Jan. 30, 2025.

U.S. Appl. No. 17/420,500 Office Action dated Jul. 18, 2024.

U.S. Appl. No. 17/427,192 Office Action dated Apr. 17, 2024.

U.S. Appl. No. 17/427,192 Office Action dated Apr. 7, 2025.

U.S. Appl. No. 17/427,192 Office Action dated Oct. 28, 2024.

U.S. Appl. No. 17/429,553 Office Action dated Feb. 27, 2025.

U.S. Appl. No. 17/432,138 Office Action dated Feb. 15, 2024.

U.S. Appl. No. 17/606,514 Office Action dated Mar. 4, 2025.

U.S. Appl. No. 17/606,514 Office Action dated Sep. 16, 2024.

U.S. Appl. No. 17/628,011 Notice of Allowance dated Oct. 15, 2024.

U.S. Appl. No. 17/628,011 Office Action dated Jun. 24, 2024.

Usmani, Shirine E. et al. Transforming growth factor-alpha induces endothelin receptor A expression in osteoarthritis. Journal of Orthopaedic Research 30(9): 1391-1397 (2012).

Usmani, Shirine E. The Role of Transforming Growth Factor Alpha in Osteoarthritis and Skeletal Development. Electronic Thesis and Dissertation Repository (2012).

Van Helvoort, E M. et al. The Role of Interleukin-4 and Interleukin-10 in Osteoarthritic Joint Disease: A Systematic Narrative Review. Cartilage 13(2):19476035221098167, 1-14 (2022).

Vanamee et al., Structural principles of tumor necrosis factor superfamily signaling. Sci Signal. 11(511):eaao4910 (2018).

Vangsness et al., Adult human mesenchymal stem cells delivered via intra-articular injection to the knee following partial medial meniscectomy: a randomized, double-blind controlled study. J Bone Joint Surg Am. 96(2):90-98 (2014).

Vizoso et al.: Mesenchymal Stem CellSecretome: Toward Cell-Free Therapeutic Strategies in Regenerative Medicine.Int. J. Mol. Sci. 18:1852 (2017).

Vogel et al.: Clinical Practice Guideline for the Management of Anorectal Abscess, Fistula-in-Ano, and Rectovaginal Fistula. Dis Colon Recturm. 59(12):1117-1133 (2016).

Von Kaeppler, Ericka P. et al. Interleukin 4 promotes anti-inflammatory macrophages that clear cartilage debris and inhibits osteoclast development to protect against osteoarthritis. Clinical immunology 229:108784, 1-10 (2021).

Vuckovic et al., Cannabinoids and pain: new insights from old molecules. Front Pharmacol. 9:1259 (2018).

Wang, et al. Exosomes from embryonic mesenchymal stem cells alleviate osteoarthritis through balancing synthesis and degradation of cartilage extracellular matrix. Stem Cell Res Ther 8(1):189, 1-13 (2017).

Wang et al., Macrophages induce AKT/beta-catenin-dependent Lgr5(+) stem cell activation and hair follicle regeneration through TNF. Nat Commun. 8:14091 (2017).

Wang et al., Upregulation of neuregulin-1 reverses signs of neuropathic pain in rats. Int J Clin Exp Pathol. 7(9):5916-5921 (2014).

Wang, Hai-jun. et al. Suppression of experimental osteoarthritis by adenovirus-mediated double gene transfer. Chinese medical journal 119(16):1365-1373 (2006).

Wang, Jiaqi. et al. Exosomes: A Novel Strategy for Treatment and Prevention of Diseases. Frontiers in Pharmacology 8:300, 1-13 (2017).

Watkins, Linda R. et al. Targeted interleukin-10 plasmid DNA therapy in the treatment of osteoarthritis: Toxicology and pain efficacy assessments. Brain, behavior, and immunity 90:155-166 (2020).

Website: ACS Webinars. https://www.acs.org/content/dam/acsorg/acs-webinars/2023/Slides/2023-03-09-exosomes-cas1.pdf (2023).

Website: https://www.youtube.com/watch?v=0RtcsA5MQPs (2019).

Website: https://www.youtube.com/watch?v=8nvgzHzBRP0 (2021).

Website: https://www.youtube.com/watch?v=dNkcd3x1HBY (2020.

Website: https://www.youtube.com/watch?v=RaV2s6x-clg (2020).

Website: https://www.youtube.com/watch?v=V606jT6aHH0 (2021).

Weiss et al.: Letter to the Editor. Response to Sengupta et al. Stem Cells and Development. 29(24):1533-1534 (2020).

Wen, Caining. et al. Insulin-like growth factor-1 in articular cartilage repair for osteoarthritis treatment. Arthritis research & therapy 23(1):277, 1-9 (2021).

Wesselius et al., Association of P2X7 receptor polymorphisms with bone mineral density and osteoporosis risk in a cohort of Dutch fracture patients. Osteoporosis International 24(4):1235-1246 (2012).

Wilkins, James M. et al. Association of a functional microsatellite within intron 1 of the BMP5 gene with susceptibility to osteoarthritis. BMC medical genetics 10:141, 1-10 (2009).

Wilson, James E. et al. Safety of Bone Marrow Derived Mesenchymal Stem Cell Extracellular Vesicle Injection for Lumbar Facet Joint Pain. Regenerative Medicine 19(1):19-26 (2024).

Xia Xianfeng et al., Secretome from hypoxia-conditioned adipose-derived mesenchymal stem cells promotes the healing of gastric mucosal injury in a rodent model. Biochim Biophys Acta Mol Basis Dis 1864(1):178-188 (2018).

Yan et al., The platelet-derived growth factor receptor/STAT3 signaling pathway regulates the phenotypic transition of corpus cavernosum smooth muscle in rats. PLoS One 12(2):e0172191 (2017).

Yang et al., Cannabidiol regulates gene expression in encephalitogenic T cells using histone methylation and noncoding RNA during experimental autoimmune encephalomyelitis. Sci Rep. 9(1):15780 (2019).

Yang et al., Effect of mesenchymal stem cells in autoimmune arthritis. Eur. J. Med. 34:130-137 (2018).

Yap, Chloe X. et al. Dissection of Genetic Variation and Evidence for Pleiotropy in Male Pattern Baldness. Nature communications 9(1):5407, 1-12 (2018).

Ye, Hantao. et al. MST1 knockdown inhibits osteoarthritis progression through Parkin-mediated mitophagy and Nrf2/NF-kB signalling pathway. Journal of cellular and molecular medicine 28(11):e18476, 1-15 (2024).

Yepes, M. Urokinase-type plasminogen activator is a modulator of synaptic plasticity in the central nervous system: implications for neurorepair in the ischemic brain. Neural Regen Res. 15(4):620-624 (2020).

Yu et al.: Exosomes Derived from Bone Marrow Mesenchymal Stem Cells as Treatment for Severe COVID-19. Stem Cells & Dev. 29(12):747-754. doi:10.1089/scd.2020.0080 (2020).

Yu et al.: Exosomes Derived from Mesenchymal Stem Cells. Int. J. Mol. Sci. 15:4142-4157 (2014) doi:10.3390/ijms15034142.

Yuan et al.: Current advances in stem cell-based therapies for hari regeneration. E. J. of Pharmacology. 881(173197):1-12 (2020).

Zafranskaya, M. et al. PGE2 contributes to in vitro MSC-mediated inhibition of non-specific and antigen-specific T cell proliferation in MS patients. Scandinavian journal of immunology 78(5):455-462 (2013).

Zhang, et al. Exosomes derived from human embryonic mesenchymal stem cells promote osteochondral regeneration. Osteoarthritis Cartilage 24(12):2135-2140 (2016).

Zhang et al., MSC exosomes mediate cartilage repair by enhancing proliferation, attenuating apoptosis and modulating immune reactivity. Biomaterials 156:16-27 (2018).

Zhao et al., NLRP3 inflammasome activation plays a carcinogenic role through effector cytokine IL-18 in lymphoma. Oncotarget 8(65):108571-108583 (2017).

Zhao et al., Stem cells for thetreatment of knee osteoarthritis: a comprehensive review. Pain Physician 21:229-241 (2018).

(56) References Cited

OTHER PUBLICATIONS

Zhao, Xiaoyi. et al. RNA-seq characterization of histamine-releasing mast cells as potential therapeutic target of osteoarthritis. Clinical Immunology 244:109117 (2022).

Zhou et al., Cross-talk between interferon-gamma and interleukin-18 in melanogenesis. J Photochem Photobiol B. 163:133-143 (2016).

Zhou et al., Effects of adipose-derived stem cells plus insulin on erectile function in streptozotocin-induced diabetic rats. Int Urol Nephrol. 48(5):657-669 (2016).

Zhou et al., Interleukin-18 augments growth ability of primary human melanocytes by PTEN inactivation through the AKT/NF-KB pathway. Int J Biochem Cell Biol. 45:308-331 (2013).

Zhu, et al. Comparison of exosomes secreted by induced pluripotent stem cell-derived mesenchymal stem cells and synovial membrane-derived mesenchymal stem cells for the treatment of osteoarthritis. Stem Cell Res Ther 8(1):64, 1-11 (2017).

Zhu, Pengfei. et al. Recombinant platelet-derived growth factor-BB alleviates osteoarthritis in a rat model by decreasing chondrocyte apoptosis in vitro and in vivo. Journal of Cellular and Molecular Medicine 25(15):7472-7484 (2021).

Zinoviev et al.: Clinical evaluation of the effectiveness of mesenchymal stem cells in thermal burns. Bulletin of the National Medical and Surgical Center named after N.A. Pirogov. 13(4):Abstract (2018).

Zohora, Fatema Tuz. et al. Secretome-based acellular therapy of bone marrow-derived mesenchymal stem cells in degenerative and immunological disorders: a narrative review. Heliyon 9(7):e18120, 1-20 (2023).

Zuker, M., On Finding All Suboptimal Foldings of an RNA Molecule. Science 244(4900):48-52 (1989).

Airan, Liu, and Qiu Haibo. et al. Research Progress on the Application of Mesenchymal Stem Cells in ALI/ARDS. Chinese Journal of Respiratory and Critical Care Medicine 9(3):332-335 (2010).

Alipoor, Shamila D. et al. Exosomes and Exosomal miRNA in Respiratory Diseases. Mediators Inflamm 2016:5628404, 1-11 (2016).

Co-pending Appl. Serial No. PCT/US2024/054785 Application as filed Nov. 6, 2024.

Co-pending Appl. Serial No. PCT/US2024/054793 Application as filed Nov. 6, 2024.

Co-pending Appl. Serial No. PCT/US2024/054794 Application as filed Nov. 6, 2024.

Co-pending U.S. Appl. No. 18/988,110 Claims as of Dec. 19, 2024.

Co-pending U.S. Appl. No. 19/205,490 Claims as of May 12, 2025.

Co-pending U.S. Appl. No. 19/256,922 Claims as of Jul. 1, 2025.

English, Karen. Mechanisms of Mesenchymal Stromal Cell Immunomodulation. Immunology and Cell Biology 91(1):19-26 (2013).

ExoFlo Information packet [retrieved from internet on May 30, 2025 URL:https://www.rejuvenate528.com/wp-content/uploads/2020/06/ExoFlo-Packet1.pdf published (2020).

Hildreth, Cade. Direct Biologics Receives FDA Approval to Proceed with Second ExoFlo IND for Post-Acute COVID-19 Syndrome and Chronic Post-COVID-19 Syndrome. Direct BioInformant Blog Jun. 9, 2021. Retrieved Mar. 26, 2025. Retrieved from https://bioinformant.com/direct-biologics-second-exoflo-ind/.

Lanyu, Zhang, and Hei Feilong. et al. Emerging role of extracellular vesicles in lung injury and inflammation. Biomed Pharmacother 113:108748, 1-9 (2019).

Lee, Jae W. et al. Concise review: Mesenchymal stem cells for acute lung injury: role of paracrine soluble factors. Stem Cells 29(6):913-919 (2011).

Mitrani, M. et al. Administration of amniotic fluid derived extracellular vesicle is associated with decreased crp in COVID-19 patients. Cytotherapy 23(5):S27 (2021).

Mitrani, Maria Ines. et al. Treatment of a COVID-19 long hauler with an amniotic fluid-derived extracellular vesicle biologic. Respiratory medicine case reports 34:101502, 1-4 (2021).

Mohammadipoor, Arezoo. et al. Therapeutic potential of products derived from mesenchymal stem/stromal cells in pulmonary disease. Respiratory Research 19(1):218, 1-14 (2018).

PCT/US2024/054785 International Search Report and Written Opinion dated Apr. 16, 2025.

Qingui, Chen, and Zeng Mian. Research Progress on Inductive Differentiation of Mesenchymal Stem Cells into Alveolar Epithelial Cells for the Treatment of Acute Respiratory Distress Syndrome. Chinese Journal of Cell and Stem Cell (Electric Edition) 7(2):124-128 (2017).

Sun, Zhongwei. et al. Stem Cell Therapies for Chronic Obstructive Pulmonary Disease: Current Status of Pre-clinical Studies and Clinical Trials. Journal of Thoracic Disease 10(2):1084-1098 (2018).

Tang, Yuling et al. Human umbilical cord-derived mesenchymal stem cell transplantation improves the long COVID. Journal of Medical Virology 96(6):1-12 (2023).

U.S. Appl. No. 17/059,874 Office Action dated Jul. 28, 2025.

Wilson, Jennifer G. et al. Mesenchymal stem (stromal) cells for treatment of ARDS: a phase 1 clinical trial. Lancet Respir Med 3(1):24-32 (2015).

Zhu, Ying-gang. et al. Human mesenchymal stem cell microvesicles for treatment of *Escherichia coli* endotoxin-induced acute lung injury in mice. Stem cells 32(1):116-125 (2014).

Zhuo, Miao. et al. Research Progress on Exosomes of Human Mesenchymal Stem Cells. Chinese Medical Biotechnology 14(4):361-365 (2019).

Co-pending Appl. Serial No. PCT/US2024/054800 Application as filed Nov. 6, 2024.

Co-pending Appl. Serial No. PCT/US2025/018972 Application as filed Mar. 7, 2025.

Co-pending Appl. Serial No. PCT/US2025/020723 Application as filed Mar. 20, 2025.

Co-pending Appl. Serial No. PCT/US2025/026049 Application as filed Apr. 23, 2025.

Co-pending Appl. Serial No. PCT/US2025/026052 Application as filed Apr. 23, 2025.

Co-pending Appl. Serial No. PCT/US2025/052304 Application as filed Oct. 23, 2025.

Co-pending U.S. Appl. No. 19/300,197 Claims as of Aug. 14, 2025.

Co-pending U.S. Appl. No. 19/370,240 Claims as of Oct. 27, 2025.

Co-pending U.S. Appl. No. 19/205,490, inventors Moseley; Timothy Alexander et al., filed on May 12, 2025.

Co-pending U.S. Appl. No. 19/256,922, inventors Pettine; Kenneth Allen et al., filed on Jul. 1, 2025.

Co-pending U.S. Appl. No. 19/370,240, inventor Moseley; Timothy Alexander, filed on Oct. 27, 2025.

Corrigendum to: Chest. 164(6):1444-1453 (2023).

Request for Regenerative Medicine Advancred Therapy (RMAT) Designation. Study Investigational Product: Bone Marrow Mesenchymal Stem Cell Derived Extracellular Vesicles Protocol No. DB-EF-PHASEII-001. Investigational New Drug (IND) No. 21669. Direct Biologics, LLC pp. 1-91 (2021).

U.S. Appl. No. 17/920,997 Office Action dated Aug. 25, 2025.

Battaglini, Denise. et al. Anti-inflammatory therapies for acute respiratory distress syndrome. Expert opinion on investigational drugs 32(12):1143-1155 (2023).

Daenen, Katrijn. et al. Increasing inflammatory biomarkers are associated with mortality in critically ill COVID-19 patients despite anti-inflammatory treatment. Clinical and experimental medicine 25(1):361, 1-14 (2025).

* cited by examiner

FIG. 1A                                    FIG. 1B

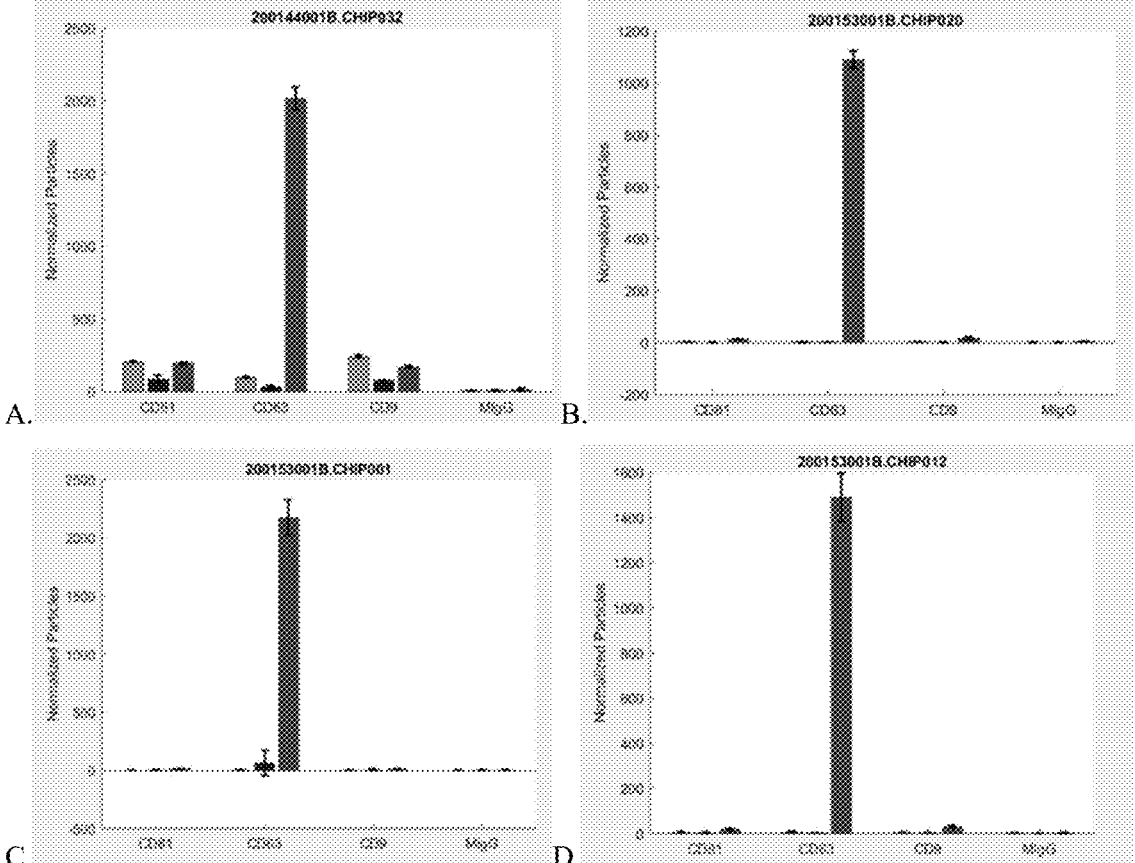
FIG. 2A, FIG. 2B, FIG. 2C, and FIG. 2D

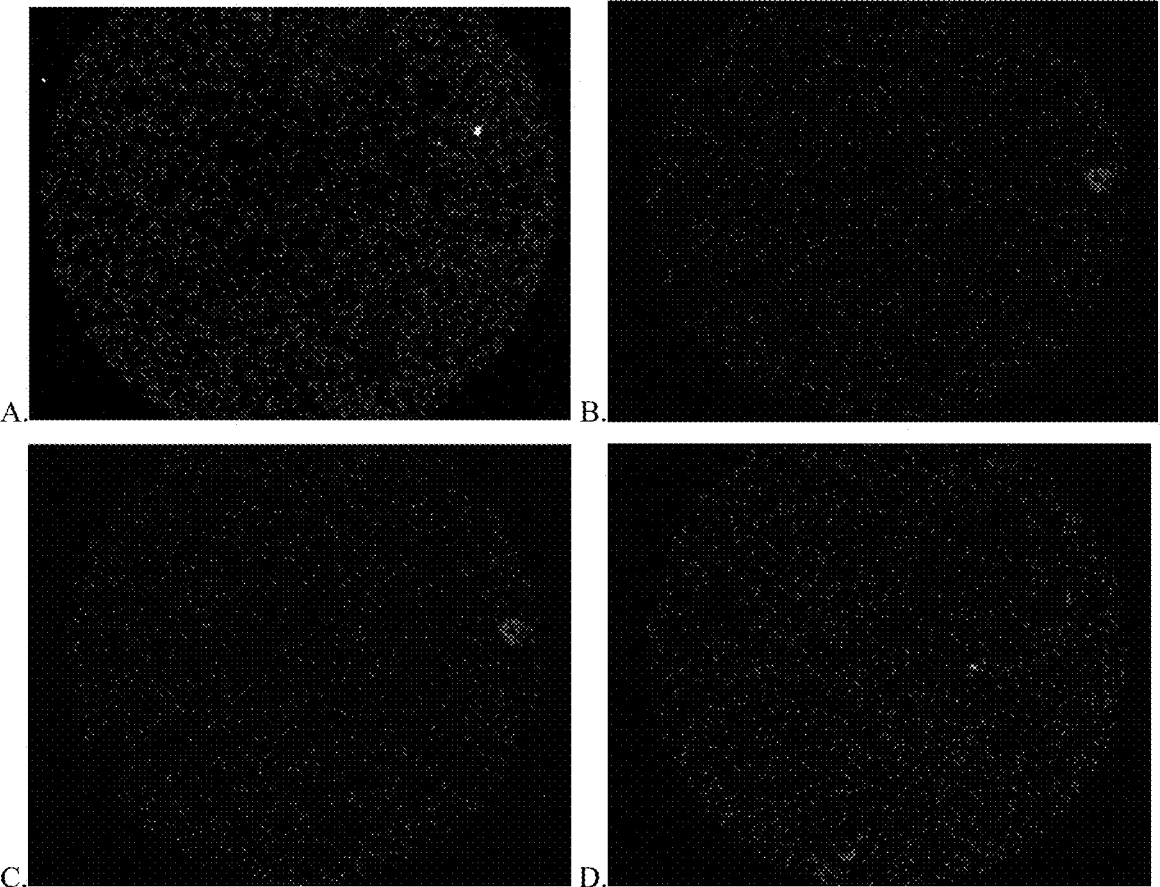
FIG. 3A, FIG. 3B, FIG. 3C, and FIG. 3D

Table 1. miRNAs predicted to bind the SARS-CoV-2 RNA genome.

| microRNA | PITA 3' UTR binding prediction[1] | | | | | | miRDB unconventional target sites prediction[2] | | |
|---|---|---|---|---|---|---|---|---|---|
| | Expression[3] (%) | Seed location[4] | Seed match length[5] | Mismatch[6] | G:U wobble[7] | microRNA-target hybridization energy[8] | Score[9] | Seed location[10] | Rank[11] |
| hsa-miR-92a-3p | 22.23476 | 29746 | 8 | 1 | 1 | -13.8 | - | - | 1 |
| hsa-miR-92b-3p | 9.976815 | 29746 | 8 | 1 | 1 | -18.8 | - | - | 3 |
| hsa-miR-18a-5p | 4.92776 | 29753 | 8 | 1 | 1 | -18.7 | 70 | 7410, 7529, 8221, 9016, 11400, 12216, 18516, 20783, 27948 | 5 |
| hsa-miR-28a-5p | 1.672265 | 29707 | 6 | 0 | 0 | -14.9 | 68 | 454, 9596, 20513, 27848, 29707 | 12 |
| hsa-miR-34b-5p | 0.925787 | 29768 | 8 | 1 | 1 | -13.25 | - | - | 20 |
| hsa-miR-23a-3p | 0.790515 | 29837 | 8 | 1 | 0 | -8.1 | 79 | 6458, 7908, 15302, 21244 | 23 |
| hsa-miR-125b-5p | 0.389675 | 29856 | 8 | 1 | 1 | -11.9 | - | - | 36 |
| hsa-miR-125a-5p | 0.324866 | 29856 | 8 | 1 | 1 | -10.4 | - | - | 37 |
| hsa-miR-103a-3p | 0.269252 | 29780 | 8 | 1 | 1 | -12.6 | 85 | 8827, 13089, 14561, 14780, 22345, 24235, 25319, 26371, 27101, 28734, 28920, 29461 | 39 |
| hsa-miR-223-3p | 0.233216 | 29863 | 8 | 1 | 1 | -5.6 | - | - | 45 |
| hsa-miR-93-5p | 0.153562 | 29746 | 8 | 1 | 1 | -15.5 | - | - | 51 |
| hsa-miR-26b-5p | 0.149508 | 29707 | 6 | 0 | 0 | -11.3 | 68 | 454, 9596, 20513, 27848, 29707 | 52 |
| hsa-miR-191-5p | 0.130145 | 29712 | 8 | 1 | 0 | -12.1 | - | - | 57 |
| hsa-miR-1307-3p | 0.129069 | 29740 | 8 | 1 | 0 | -30.9 | - | - | 58 |
| hsa-miR-55-5p | 0.098556 | 29693 | 8 | 1 | 0 | -9.3 | 51 | 864, 5209, 17197, 25074 | 63 |
| hsa-miR-185-5p | 0.050131 | 29726 | 8 | 1 | 1 | -11.31 | - | - | 69 |
| hsa-miR-23b-3p | 0.029939 | 29837 | 8 | 1 | 0 | -11.3 | 79 | 6458, 7908, 15302, 21244 | 74 |

FIG. 4

METHODS AND COMPOSITIONS FOR TREATING INFLAMMATORY CONDITIONS ASSOCIATED WITH INFECTIOUS DISEASE

This application is a continuation of U.S. application Ser. No. 17/920,997, filed on Oct. 24, 2022, which is a 371 U.S. National Stage of International Application No. PCT/US2021/028686, filed on Apr. 22, 2021, which claims the benefit of U.S. Provisional Application No. 63/198,706, filed on Nov. 6, 2020, and U.S. Provisional Application No. 63/013,865, filed on Apr. 22, 2020, each of which is incorporated herein by reference in its entirety.

I. BACKGROUND

There are currently no effective biologic treatments for coronaviruses, especially for COVID-19. Commercially available products do not act concurrently and synergistically to directly affect viral infection and/or replication as well as to regulate downstream inflammation and vascular cell related pathologies in response to the viral infection. Therefore, what is needed is a method and composition for an intravenous or pulmonary route of delivery of autogenous or allogenic MSC derived growth factors and exosomes, wherein the products are acellular and useful for the treatment of various viruses, while simultaneously avoiding the potential negative long-term effects associated with introducing cellular living MSCs into a recipient.

II. SUMMARY

Disclosed are methods and compositions related to a composition comprising MSC secretome (such as, for example, including, but not limited to MSC growth factor, MSC exosome, MSC extracts and/or extracellular vesicle comprising compositions) and/or one or more biomolecules for use treating diseases.

In one aspect, disclosed herein are compositions comprising a therapeutically effective amount of a MSC secretome (such as, for example, including, but not limited to MSC growth factor, MSC exosome, MSC extracts and/or extracellular vesicle comprising compositions) and one or more biomolecules (such as, for example, a peptide, polypeptide, protein, siRNA, shRNA, and/or microRNA (miRNA)) that selectively bind to one or more microbial immunogens, or inhibit the ability of a microbe to inhabit a host, or inhibit, decrease, reduce, ameliorate, and/or prevent one or more secondary conditions caused by a microbial infection (such as, for example, comprise a peptide, polypeptide, protein, siRNA, shRNA, microRNA (miRNA) which act concurrently and synergistically to directly affect viral infection and/or replication and/or act concurrently and synergistically to regulate downstream inflammation and vascular cell related pathologies in response to microbial infection). For example, disclosed herein are compositions comprising a therapeutically effective amount of a MSC secretome (such as, for example, including, but not limited to MSC growth factor, MSC exosome, MSC extracts and/or extracellular vesicle comprising compositions) and one or more biomolecules comprise a ferritin protein, PAI-1, thrombomodulin, and/or a miRNA is selected from the group of miRNA comprising hsa-let-7a-5p, hsa-let-7b-5p, hsa-let-7c-5p, hsa-let-7d-3p, hsa-let-7e-5p, hsa-let-7g-5p, hsa-let-7i, hsa-let-7i-5p, hsa-miR-100-5p, hsa-miR-103a-3p, hsa-miR-106a-5p, hsa-miR-106b-5p, hsa-mir-10b, hsa-miR-10b-5p, hsa-mir-1246, hsa-miR-1246, hsa-miR-125a-5p, hsa-miR-125b-5p, hsa-miR-130a-3p, hsa-mir-130b, hsa-miR-130b-3p, hsamiR-132-3p, hsa-miR-136-5p, hsa-miR-138-5p, hsa-miR-139-5p, hsa-mir-140, hsa-miR-140-3p, hsa-miR-145-5p, hsa-mir-146a, hsa-miR-146a-5p, hsa-miR-148a-3p, hsa-miR-152-3p, hsa-miR-15a-5p, hsa-miR-15b-5p, hsa-mir-16-1, hsa-mir-16-2, hsa-miR-16-5p, hsa-miR-17-5p, hsa-miR-181a-5p, hsa-miR-191-5p, hsa-miR-193a-5p, hsa-miR-193b-3p, hsa-miR-197-3p, hsa-miR-199a-3p, hsa-miR-199a-5p, hsa-miR-199b-5p, hsa-miR-19a-3p, hsa-miR-19b-3p, hsa-miR-20a-5p, hsa-mir-203a, hsa-miR-203a-3p, hsa-miR-214-3p, hsa-mir-21, hsa-miR-21-3p, hsa-miR-21-5p, hsa-mir-221, hsa-miR-221-3p, hsa-mir-222, hsa-miR-222-3p, hsa-miR-22-3p, hsa-miR-23a-3p, hsa-miR-23b-3p, hsa-mir-24-1, hsa-mir-24-2, hsa-miR-24-3p, hsa-mir-25, hsa-miR-25-3p, hsa-miR-26a-5p, hsa-miR-27a-3p, hsa-mir-27b, hsa-miR-27b-3p, hsa-miR-29a-3p, hsa-miR-29c-3p, hsa-miR-30a-5p, hsa-miR-30a-5p, hsa-miR-30b-5p, hsa-miR-30c-5p, hsa-mir-30d, hsa-miR-30d-5p, hsa-mir-30e, hsa-miR-30e-5p, hsa-miR-31-3p, hsa-miR-31-5p, hsa-miR-320a, hsa-miR-342-3p, hsa-miR-345-5p, hsa-miR-34a-5p, hsa-miR-361-5p, hsa-miR-376a-3p, hsa-miR-376c-3p, hsa-miR-423-3p, hsa-miR-423-5p, hsa-miR-424-5p, hsa-miR-484, hsa-mir-486-1, hsa-mir-486-2, hsa-miR-486-5p, hsa-miR-570-3p, hsa-miR-574-3p, hsa-miR-663a, hsa-miR-874-3p, hsa-mir-92a-1, hsa-mir-92a-2, hsa-miR-92a-3p, hsa-miR-92b-3p, hsa-mir-93, hsa-miR-93-5p, hsa-miR-940, hsa-miR-99a-5p, and hsa-miR-99b-5p.

Also disclosed herein are compositions of any preceding aspect, wherein the one or more biomolecules inhibit the bradykinin pathway (for example, by inhibiting translation of Bradykinin 2), angiotensin-converting enzyme 2 (ACE 2) receptor, inhibits the transmembrane protease, seine 2 (TM-PRSS2) enzyme, inhibits Kallikrein B1, and/or inhibits IL-1β, IL-6, TNF-α, GM-CSF, or M-CSF.

In one aspect, disclosed herein are compositions of any preceding aspect, wherein the MSC secretome further comprises prostaglandin E2 (PGE2), transforming growth factor β31 (TGF-β1), hepatocyte growth factor (HGF), stromal cell derived factor-1 (SDF-1), nitric oxide, indoleamine 2,3-dioxygenase, interleukin-4 (IL-4), IL-6, interleukin-10 (IL-10), IL-1 receptor antagonist and soluble TNF-α receptor, insulin-like growth factors, fibroblast growth factors (FGF) 1-23 (especially, FGF1 and FGF2), bone morphogenetic proteins (BMPs) 1-15, epidermal growth factor (EGF), transforming growth factor-α (TGF-α) macrophage-stimulating protein (MSP), platelet derived growth factor (PLGF), vascular endothelial growth factor (VEGF), macrophage colony stimulating factor (M-CSF), insulin, granulocyte colony stimulating factor (G-CSF), granulocyte macrophage colony stimulating factor (GM-CSF estrogen, and/or thyroid hormones.

Also disclosed herein are methods of treating, decreasing, inhibiting, reducing, ameliorating and/or preventing a microbial infection (such as, for example, a viral, bacterial, fungal, or parasitic infection) or symptoms thereof (including, but not limited to microbial induced cytokine storm, microbial initiated bradykinin storm, and/or acute respiratory distress syndrome) in a subject comprising administering to a subject the composition of any preceding aspect.

In one aspect, disclosed herein are methods of treating, decreasing, inhibiting, reducing, ameliorating and/or preventing a microbial infection or symptoms thereof of any preceding aspect, wherein the microbial infection comprises an infection from a virus selected from the group of viruses consisting of Herpes Simplex virus-1, Herpes Simplex virus-2, Varicella-Zoster virus, Epstein-Barr virus, Cytomegalovirus, Human Herpes virus-6, Variola virus, Vesicular stomatitis virus, Hepatitis A virus, Hepatitis B virus, Hepatitis C virus, Hepatitis D virus, Hepatitis E virus, Rhinovirus, Coronavirus (including, but not limited to avian coronavirus (IBV), porcine coronavirus HKU15 (PorCoV HKU15), Porcine epidemic diarrhea virus (PEDV), HCoV-229E, HCoV-OC43, HCoV-HKU1, HCoV-NL63, SARS-CoV, SARS-CoV-2, or MERS-CoV), Influenza virus A, Influenza virus B, Measles virus, Polyomavirus, Human Papillomavirus, Respiratory syncytial virus, Adenovirus, Coxsackie virus, Chikungunya virus, Dengue virus, Mumps virus, Poliovirus, Rabies virus, Rous sarcoma virus, Reovirus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Simian Immunodeficiency virus, Human T-cell Leukemia virus type-1, Hantavirus, Rubella virus, Simian Immunodeficiency virus, Human Immunodeficiency virus type-1, and Human Immunodeficiency virus type-2.

Also disclosed herein are methods of treating, decreasing, inhibiting, reducing, ameliorating and/or preventing a microbial infection or symptoms thereof of any preceding aspect, wherein the microbial infection comprises an infection from a bacteria selected from the group of bacteria consisting of *Mycobacterium tuberculosis, Mycobacterium bovis, Mycobacterium bovis* strain BCG, BCG substrains, *Mycobacterium avium, Mycobacterium intracellular, Mycobacterium africanum, Mycobacterium kansasii, Mycobacterium marinum, Mycobacterium ulcerans, Mycobacterium avium* subspecies paratuberculosis, *Mycobacterium chimaera, Nocardia asteroides,* other *Nocardia* species, *Legionella pneumophila,* other *Legionella* species, *Acetinobacter baumanii, Salmonella typhi, Salmonella enterica,* other *Salmonella* species, *Shigella boydii, Shigella dysenteriae, Shigella sonnei, Shigella flexneri,* other *Shigella* species, *Yersinia pestis, Pasteurella haemolytica, Pasteurella multocida,* other *Pasteurella* species, *Actinobacillus pleuropneumoniae, Listeria monocytogenes, Listeria ivanovii, Brucella abortus,* other *Brucella* species, *Cowdria ruminantium, Borrelia burgdorferi, Bordetella avium, Bordetella pertussis, Bordetella bronchiseptica, Bordetella trematum, Bordetella hinzii, Bordetella pteri, Bordetella parapertussis, Bordetella ansorpii* other *Bordetella* species, *Burkholderia mallei, Burkholderia psuedomallei, Burkholderia cepacian, Chlamydia pneumoniae, Chlamydia trachomatis, Chlamydia psittaci, Coxiella bumetii, Rickettsial* species, *Ehrlichia* species, *Staphylococcus aureus, Staphylococcus epidermidis, Streptococcus pneumoniae, Streptococcus pyogenes, Streptococcus agalactiae, Escherichia coli, Vibrio cholerae, Campylobacter* species, *Neiserria meningitidis, Neiserria gonorrhea, Pseudomonas aeruginosa,* other *Pseudomonas* species, *Haemophilus influenzae, Haemophilus ducreyi,* other *Hemophilus* species, *Clostridium tetani,* other *Clostridium* species, *Yersinia enterolitica,* and other *Yersinia* species, and *Mycoplasma* species. In one aspect the bacteria is not *Bacillus anthracis.*

In one aspect, also disclosed herein are methods of treating, decreasing, inhibiting, reducing, ameliorating and/or preventing a microbial infection or symptoms thereof of any preceding aspect, wherein the microbial infection comprises an infection from a fungus selected from the group of fungi consisting of *Candida albicans, Cryptococcus neoformans, Histoplasma capsulatum, Aspergillus fumigatus, Coccidiodes immitis, Paracoccidioides brasiliensis, Blastomyces dermitidis, Pneumocystis carinii, Penicillium marneffi,* and *Alternaria altemata.*

Also disclosed herein are methods of treating, decreasing, inhibiting, reducing, ameliorating and/or preventing a microbial infection or symptoms thereof of any preceding aspect, wherein the microbial infection comprises a parasitic infection with a parasite selected from the group of parasitic organisms consisting of *Toxoplasma gondii, Plasmodium falciparum, Plasmodium vivax, Plasmodium malariae,* other *Plasmodium* species, *Entamoeba histolytica, Naegleria fowleri, Rhinosporidium seeberi, Giardia lamblia, Enterobius vermicularis, Enterobius gregorii, Ascaris lumbricoides, Ancylostoma duodenale, Necator americanus, Cryptosporidium* spp., *Trypanosoma brucei, Trypanosoma cruzi, Leishmania major,* other *Leishmania* species, *Diphyllobothrium latum, Hymenolepis nana, Hymenolepis diminuta, Echinococcus granulosus, Echinococcus multilocularis, Echinococcus vogeli, Echinococcus oligarthrus, Diphyllobothrium latum, Clonorchis sinensis; Clonorchis viverrini, Fasciola hepatica, Fasciola gigantica, Dicrocoelium denderiticum, Fasciolopsis buski, Metagonimus yokogawai, Opisthorchis viverrini, Opisthorchis felineus, Clonorchis sinensis, Trichomonas vaginalis, Acanthamoeba species, Schistosoma intercalatum, Schistosoma haematobium, Schistosoma japonicum, Schistosoma mansoni,* other *Schistosoma* species, *Trichobilharzia regenti, Trichinella spiralis, Trichinella britovi, Trichinella nelsoni, Trichinella nativa,* and *Entamoeba histolytica.*

III. BRIEF DESCRIPTION OF THE DRAWINGS

The accompanying drawings, which are incorporated in and constitute a part of this specification, illustrate several embodiments and together with the description illustrate the disclosed compositions and methods.

FIGS. 1A, 1B, and 1C show a set of representative images captured by transmission electron microscopy (TEM) showing size distribution of EVs present within a sample of a composition according to an embodiment of the invention;

FIGS. 2A, 2B, 2C, and 2D are a set of charts representing numbers of captured exosome particles;

FIGS. 3A, 3B, 3C, and 3D are a set of microphotographic images of CD63 captured exosomes;

FIG. 4 is a table from Park et al. (2020) BioRxiv showing miRNAs predicted to bind the SARS-CoV-2 RNA genome FIG. 5 is a schematic representation of multiple mechanisms of action of the inventive composition; and FIG. 6 is a graph demonstrating a direct effect of the composition of FIG. 1 on live CoV-2 virus replication.

FIG. 7 is a compilation of graphs demonstrating the effect of the invention when administered to patients with severe COVID-19 related ARDS. Response of COVID-19 patients to intravenous administration of invention. "Acute phase reactants" (CRP, ferritin, and D-dimer) and immune cell populations on day of treatment before IV administration and on day 5 post-treatment. Mean reductions of CRP, ferritin, and D-dimer reductions were 77% (P<0.001), 43% (P<0.001), and 42% (P<0.05), respectively. Mean reduction of ANC was 32% (P<0.001); Total lymphocyte count increased by 36% (P<0.05) with CD3+, CD4+, and CD8+T lymphocytes increased by 46% (P<0.05), 45% (P<0.05), and 46% (P<0.001), respectively. ANC, absolute neutrophil count; CRP, C-reactive protein.

IV. DETAILED DESCRIPTION

Figure 1C:
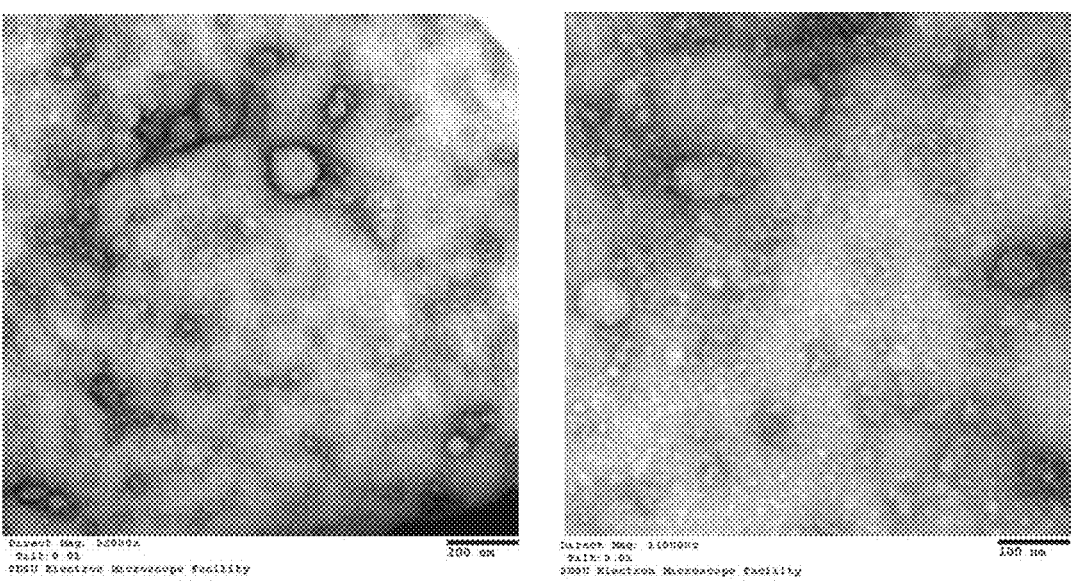

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

The term "subject" is defined herein to include animals such as mammals, including, but not limited to, primates (e.g., humans), cows, horses, pigs, sheep, goats, dogs, cats, rabbits, rats, mice and the like. In some embodiments, the subject is a human.

"Administration" to a subject includes any route of introducing or delivering to a subject an agent. Administration can be carried out by any suitable route, including oral, topical, intravenous, subcutaneous, transcutaneous, transdermal, intramuscular, intra-joint, parenteral, intra-arteriole, intraarticular, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. "Concurrent administration", "administration in combination", "simultaneous administration" or "administered simultaneously" as used herein, means that the compounds are administered at the same point in time or essentially immediately following one another. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g. greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration but are undetectable or detectable at negligible amounts in distal parts of the subject's body. Administration includes self-administration and the administration by another.

"Biocompatible" generally refers to a material and any metabolites or degradation products thereof that are generally non-toxic to the recipient and do not cause significant adverse effects to the subject.

"Comprising" is intended to mean that the compositions, methods, etc. include the recited elements, but do not exclude others. "Consisting essentially of" when used to define compositions and methods, shall mean including the recited elements, but excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "control" is an alternative subject or sample used in an experiment for comparison purposes. A control can be "positive" or "negative."

"Effective amount" of an agent refers to a sufficient amount of an agent to provide a desired effect. The amount of agent that is "effective" will vary from subject to subject, depending on many factors such as the age and general condition of the subject, the particular agent or agents, and the like. Thus, it is not always possible to specify a quantified "effective amount." However, an appropriate "effective amount" in any subject case may be determined by one of ordinary skill in the art using routine experimentation. Also, as used herein, and unless specifically stated otherwise, an "effective amount" of an agent can also refer to an amount covering both therapeutically effective amounts and prophylactically effective amounts. An "effective amount" of an agent necessary to achieve a therapeutic effect may vary according to factors such as the age, sex, and weight of the subject. Dosage regimens can be adjusted to provide the optimum therapeutic response. For example, several divided doses may be administered daily, or the dose may be proportionally reduced as indicated by the exigencies of the therapeutic situation.

A "decrease" can refer to any change that results in a smaller gene expression, protein production, amount of a symptom, disease, composition, condition, or activity. A substance is also understood to decrease the genetic output of a gene when the genetic output of the gene product with the substance is less relative to the output of the gene product without the substance. Also, for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

"Treat," "treating," "treatment," and grammatical variations thereof as used herein, include the administration of a composition with the intent or purpose of partially or completely preventing, delaying, curing, healing, alleviating, relieving, altering, remedying, ameliorating, improving, stabilizing, mitigating, and/or reducing the intensity or frequency of one or more a diseases or conditions, a symptom of a disease, disorder, injury, or condition, or an underlying cause of a disease or condition. Treatments according to the invention may be applied preventively, prophylactically, pallatively or remedially. Prophylactic treatments are administered to a subject prior to onset (e.g., before obvious signs of cancer), during early onset (e.g., upon initial signs and symptoms of cancer), or after an established development of cancer. Prophylactic administration can occur for day(s) to years prior to the manifestation of symptoms of an infection.

The terms "prevent," "preventing," "prevention," and grammatical variations thereof as used herein, refer to a method of partially or completely delaying or precluding the onset or recurrence of a disease and/or one or more of its attendant symptoms or barring a subject from acquiring or reacquiring a disease or reducing a subject's risk of acquiring or reacquiring a disease or one or more of its attendant symptoms.

"Pharmaceutically acceptable" component can refer to a component that is not biologically or otherwise undesirable, i.e., the component may be incorporated into a pharmaceutical formulation of the invention and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic and includes a carrier that is acceptable for veterinary and/or human pharmaceutical or therapeutic use. The terms "carrier" or "phar-maceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

"Pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

"Therapeutic agent" refers to any composition that has a beneficial biological effect. Beneficial biological effects include both therapeutic effects, e.g., treatment of a disorder or other undesirable physiological condition, and prophylactic effects, e.g., prevention of a disorder or other undesirable physiological condition (e.g., a non-immunogenic cancer). The terms also encompass pharmaceutically acceptable, pharmacologically active derivatives of beneficial agents specifically mentioned herein, including, but not limited to, salts, esters, amides, proagents, active metabolites, isomers, fragments, analogs, and the like. When the terms "therapeutic agent" is used, then, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc.

"Therapeutically effective amount" or "therapeutically effective dose" of a composition (e.g. a composition comprising an agent) refers to an amount that is effective to achieve a desired therapeutic result. In some embodiments, a desired therapeutic result is the control of type I diabetes. In some embodiments, a desired therapeutic result is the control of obesity. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect, such as pain (i.e., nociception) relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular MSC secretome (including, but not limited to a MSC exosome (with or without growth factors) referred to herein as an extracellular vesicle isolate product (EVIP)) is disclosed and discussed and a number of modifications that can be made to a number of molecules including the MSC secretome are discussed, specifically contemplated is each and every combination and permutation of MSC secretome and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Currently, COVID-19 is ravaging the world. It has been widely reported that children are less likely to get severely ill and die from COVID-19. A recent study of 44,672 people with confirmed COVID-19 infection found that children under 10 years old made up less than 1 percent of those cases and none of the 1,023 deaths. A straightforward explanation would be that children are resisting infection in the first place, but that does not seem to be the case. Children are just as likely as adults to get infected. So, what is protecting children? Experts suspect it may be because of the unique way children's immune systems respond to these viruses.

A common complication of COVID-19, SARS and MERS in adults is where the immune response against the coronavirus becomes overzealous and causes life-threatening damage to the lungs. The resulting leakage of fluid and immune cells into the lungs can result in life threatening acute respiratory distress syndrome (ARDS) problems. Even if those immune responses are trying to help by attacking the virus, they can end up blocking oxygen uptake in the lungs. Because children's immune systems are still developing, one suggestion is that they are shielded from this type of dangerous immune response, called a cytokine storm, when they get COVID-19 or similar diseases.

Airway epithelial cell injury is also important in COVID-19 pathogenesis. Injured lung epithelial cells are a source of inflammatory mediators such as IL-6, TNF-$\alpha$, IL-1$\beta$, GM-CSF, and CXCL-8, which may act in both autocrine and paracrine manners. IL-6 induces the remodeling of airway cells by regulation and promoting of myofibroblast differentiation which is the main cause of fibrosis development during airway remodeling. The paracrine activity of these mediators is mediated, at least in part, by inflammatory exosomes.

Acute inflammation is a key pathological feature of the COVID-19 process. For example, cytokines produced by natural killer cells, mast cells, macrophages, and monocytes at the site of inflammation play a key role in the development of the COVID-19 cytokine storm that results in ARDS. Proinflammatory biomarkers, such as cytokines, have been found in both chronic and acute pulmonary disease states, suggesting either a direct or faciliatory role in the occurrence of the pathology. Multiple cytokines are produced during an inflammatory reaction. Cytokines contribute to inflammatory processes by activation of specific signal transduction mechanisms as well as the activation of other cell types. Cytokines are found extracellularly (in blood) and in interstitial compartments, where they can activate cells in an autocrine/paracrine fashion. It has been postulated that increased levels of cytokines influence and contribute to COVID-19 respiratory symptoms by increasing the sensitization of nociceptors. When tissue is invaded or destroyed by pulmonary leukocytes during an inflammatory episode, several mediators such as interleukin-1 (IL-1), IL-8, IL-6, and tumor necrosis factor alpha (TNF-$\alpha$) migrate to the site. Also included in these mediators are nerve growth factor and prostaglandins. These all result in pulmonary inflammation.

Mesenchymal stem cells (MSCs) have attracted much attention for their ability to regulate inflammatory processes. In many types of pulmonary trauma, inflammatory conditions at the site of injury impede the natural repair processes by local progenitor and mature cells. MSCs assist via paracrine mechanisms and modulate the regenerative environment via anti-inflammatory and immunomodulatory mechanisms. In response to inflammatory molecules such as interleukin-1 (IL-1), IL-2, 11-6, IL-12, tumor necrosis factor-a (TNF-$\alpha$) and interferon-gamma (INF-$\gamma$), MSCs secrete an array of growth factors and anti-inflammatory proteins with complex feedback mechanisms among the many types of immune cells. The key immunomodulatory cytokines include prostaglandin 2, TGF-$\beta$1, HGF, SDF-1, indoleamine 2,3-dioxygenase, IL-4, IL-1$\beta$, IL-1 receptor antagonist and soluble tumor necrosis factor-a receptor. MSCs prevent proliferation and the dysfunction of many inflammatory immune cells, including T cells, natural killer cells, B cells, monocytes, macrophage, and dendritic cells.

The primary trophic property of MSCs is the secretion of growth factors and exosomes to induce cell proliferation and angiogenesis. Exosomes express mitogenic proteins such as transforming growth factor-alpha (TGF-$\alpha$), TGF-$\beta$, hepatocyte growth factor (HGF), epithelial growth factor (EGF), basic fibroblast growth factor (FGF-2) and insulin-like growth factor-1 (IGF-1). These increase fibroblast, epithelial and endothelial cell division. Vascular endothelial growth factor (VEGF), IGF-1, EGF and angiopoietin-1 are released to recruit endothelial lineage cells and initiate vascularization.

MSCs assist via paracrine mechanisms and modulate the regenerative environment via anti-inflammatory and immunomodulatory mechanisms. In response to inflammatory molecules such as interleukin-1 (IL-1), IL-6, IL-2, IL-12, tumor necrosis factor-$\alpha$ (TNF-$\alpha$) and interferon-gamma (INF-$\gamma$), MSCs secrete an array of growth factors and anti-inflammatory proteins with complex feedback mechanisms among the many types of immune cells. The key immunomodulatory cytokines include prostaglandin 2, TGF-β1, HGF, SDF-1, nitrous oxide, indoleamine 2,3-di-oxygenase, IL-4, IL-1β, IL-1 receptor antagonist and soluble tumor necrosis factor-α receptor. MSCs prevent proliferation and function of many inflammatory immune cells, including T-cells, natural killer cells, B-cells, monocytes, macrophages, and dendritic cells. Although MSCs across species are able to regulate T-cell activity, the mechanisms are not identical across mammalian species.

A characteristic of chronically inflamed environments is a persistent imbalance in the types of helper T-cells and macrophages. MSC exosomes indirectly promote the transition of TH1 to TH2 cells by reducing INF-γ and increasing IL-4 and IL-10. The restored TH1/TH2 balance has been shown to improve tissue regeneration in cartilage, muscle, and other soft tissue injuries, alleviate symptoms of auto-immune diseases, and have an anti-diabetic effect. Similarly, reduction in INF-γ and secretion of IL-4 promotes a shift in macrophages from M1 (proinflammatory, anti-angiogenic and tissue growth inhibition) to M2 (anti-inflammatory, pro-remodeling and tissue healing) type, an effect required for skeletal, muscular, and neural healing and regeneration.

Disclosed herein is a complex composition of secreted biomolecules (proteins, lipids, and ribonucleic acids) and/or extracellular vesicles comprising biomolecules, originating from mesenchymal lineage cells, that interact directly with microbial proteins (such as, for example, a coronavirus protein) and/or nucleic acid content (such as, for example microbial ribonucleic acid content) to disrupt the capacity of the microbe to establish an infection in the subject, infect cells, and/or replicate within cells, and that concurrently interact with infected cells and immune response cells to resolve hyperactive responses (such as for example, microbial induced cytokine storm, microbial initiated bradykinin storm, and/or acute respiratory distress syndrome). In one aspect, disclosed herein are compositions comprising a therapeutically effective amount of a MSC secretome (such as, for example, including, but not limited to MSC growth factor, MSC exosome, MSC extracts and/or extracellular vesicle comprising compositions) and one or more biomolecules (such as, for example, a peptide, polypeptide, protein, siRNA, shRNA, and/or microRNA (miRNA)) that selectively bind to one or more microbial immunogens, or inhibit the ability of a microbe to inhabit a host, or inhibit, decrease, reduce, ameliorate, and/or prevent one or more secondary conditions caused by a microbial infection (such as, for example, comprise a peptide, polypeptide, protein, siRNA, shRNA, microRNA (miRNA) which act concurrently and synergistically to directly affect viral infection and/or replication and/or act concurrently and synergistically to regulate downstream inflammation and vascular cell related pathologies in response to microbial infection).

In some embodiments, the composition comprises bone marrow-derived mesenchymal lineage cells that adhere to culture plastic and may differentiate in culture into multiple mature cell fates including but not limited to adipocyte, osteoblast and chondrocyte fates and/or secreted extracellular vesicles that contain a core protein composition that includes any combination of core composition proteins, selected from the group consisting of. Ferritin, NUP85, LAMP2, GPR115, Serpin F1, OPN, PAI-1, DAPP1, Cathepsin B, Semaphorin 6C, PDGF R alpha, Sortilin, Serpin B6, Dkk-3, Thrombomodulin, PF4, MIF, Periostin, Furin, TIMP-1, Decorin, PCK1, CD99, CD63, CD9, CD81, Transferrin, DcR3, Lumican, TIMP-2, SLITRK5, FAP, Artemin, DPPII, cIAP-1, Pentraxin 3, Visfatin, Neprilysin, Albumin, Galectin-1, UNC5H3, IL-20 R beta, SREC-II, JAM-C, TNF RI, htPAPP-A, eNOS, MSP R, TPP1, LAMP1, B2M, NCAM-1, HIF-1 alpha, ST6GAL1, CD99-L2, Plexin A4, EMMPRIN, p53, Semaphorin 7A, NKp80, Cystatin B, Osteoadherin, Midkine, Calreticulin, Osteoactivin, Legumain, TAZ, Cathepsin L, RBP4, Serpin A4, JAM-A, MCSF, LIMPII, OPG, IL-22, Galectin-3, MOG, Trypsin 3, SIRP alpha, and Syndecan-4, and at least one protein selected from the group consisting of: Ferritin, IGFBP-4 IL-1 R6 GSTM1, NUP85, LAMP2, MeprinA, IL-1 F10, bIG-H3, GPR115, TGFb1, Ephrin-A4, CD109, Serpin F1, IGFBP-6, HS3ST4, Aminopeptidase LRAP, OPN, PAI-1, DAPP1, GDF-9, Cathepsin B, IGFBP-2, Semaphorin 6C, IGF-2, PDGF R alpha, Sortilin, Serpin B6, Dkk-3, CNTF, TSP-1, GM-CSF Ra, Thrombomodulin, Endoglycan, IGFBP-3, RGM-C, PF4, MIF, TGM4, Periostin, Furin, TIMP-1, PAPP-A, Decorin, PCK1, Arylsulfatase A, CD99, CA2, PRDX4, Transferrin, DcR3, GP73, LAIR2, ULBP-4, Lumican, TIMP-2, TFPI, SOX2, SLITRK5, FAP, Spinesin, ENPP-2, CD97, CTACK, Integrin alpha 1, EXTL3, IL-18 BPa, PD-L2, PSMA, IL-20 Ra, Glyoxalase II, Trypsin 1, IGF-2R, ADAMTSL-1, Erythropoietin, Plexin D1, DNMT3A, BCL-2, CL-P1, Ephrin-B3, FABP6, CHI3L1, FCRL5, TFF3, Artemin, DPPII, cIAP-1, PDGF Rb, Pentraxin 3, Angiotensinogen, Follistatin, CF VII, Persephin, TRAIL R1, THAP11, CD200, CLEC-2, AMIGO, IGFBP-5, PON1, SOX7, GALNT10, Visfatin, Progranulin, PCSK2, GKN1, IL-18, Neprilysin, Stabilin-2, IL-17 RD, Albumin, Follistatin-like 1, MMP-10, FKBP51, LRRC4, Pref-1, Galectin-1, Troponin C, UNC5H3, FLRT2, CD314, Semaphorin 6B, Netrin-4, CD27 Ligand, IL-20 R beta, Semaphorin 6A, TSK, Cytokeratin-8, CHST3, Mcl-1, DPPIV, SREC-II, Norrin, JAM-C, Bcl-10, Wnt-4, LSECtin, Kell, TNF RI, PTP1B, htPAPP-A, IDO, PDGF-CC, Galanin, Activin A, TLR2, SCCA2, FABP1, eNOS, SHP-1, ICOS, ClqTNF9, MMP-1, TC-PTP, IL-24, gp130, C-myc, LILRB4, BMP-2, MIA, CD34, CD63, CD9, CD81, IFNab R2, Glypican 2, MSP R, DSCAM, Matriptase, KIR2DL3, CD30, Siglec-10, CLEC-1, TPP1, Ubiquitin+1, ANGPTL4, TWEAK R, Nidogen-1, CD2, Kallikrein 1, TSLP R, LAMP1, TROY, VCAM-1, Siglec-11, S100A1, PARI, Thyroid Peroxidase, Aminopeptidase P2, IL-1 RI, ADAM9, OSM R beta, Thrombospondin-2, SMPD1, B2M, MFRP, LRP-6, ST3GAL1, NCAM-1 (CD56), Granzyme B, Adiponectin, IL-22BP, TPST2, PD-ECGF, LH, LEDGF, Cyr61, ULBP-3, IFNb, THSD1, FGF-23, LAMA4, Adipsin, AIF, SorCS2, SULT2A1, CD39L2, Insulin R, HIF-1 alpha, OX40 Ligand, Pax3, UCH-L3, cMASP3, Langerin, Desmin, SOX9, ST6GAL1, MEP1B, CD99-L2, Plexin A4, Semaphorin 4D, ROBO2, PDX-1, APRIL, Neurturin, Kremen-2, EMMPRIN, Activin RIB, Neuroligin 2, Epiregulin, CA5A, MMP-12, GALNT2, CEACAM-5, VEGF R1, DSPG3, SorCS1, Matrilin-2, sFRP-3, p53, EphB3, NCKI, Semaphorin 7A, NKp80, Prolactin, Cystatin B, Sirtuin 1, FGF-16, FGF R5, NQO-1, Semaphorin 6D, FGF-3, GATA-4, VAP-A, CHST2, Pappalysin-2, Syndecan-3, Jagged 1, AKR1C4, Olfactomedin-2, Osteoadherin, NKp44, Thyroglobulin, IL-21R, Chemerin, EphA1, CD48, MICB, FGF-5, TRANCE, CES2, ULBP-1, Integrin alpha 5, VAMP-2, FLRG, Ret Midkine, CD73, TRACP, proGRP, Granzyme H, PRX2, p27, Siglec-6, Dectin-1, CD51, Notch-1, Calreticulin, DR3, DCTN1, CDC25B, Osteoactivin, ACE, CA125, HAO-1, PSMA1, FCRLB, BMP-9, CRIM1, LIF, SPINK1, EphB6, RGM-B, HS3ST1, ROR1, CMG-2, 4-1BB Ligand, LICAM-2, p63, Cathepsin V, Testican 2, Glypican 5, CD6, Siglec-2, Legumain, PRELP, CES1, TAZ, NSE, TECK, HTRA2, HIF-1 beta, TAFA1, Podocalyxin, RalA, CRELD2, GRAP2, SP-D, BID, GFR alpha-2, Notch-3, VEGF R3, DLL4, TGFb2, LIGHT, XIAP, ST8SIA1, Cathepsin L, 6Ckine, MIS RII, Kallikrein 5, TGM3, FCAR, Contactin-2, CD83, IL-1 R3, SALM4, GBA3, ROBO4, OSCAR, VEGF, IGSF3, Biglycan, Neudesin, ILT4, uPAR, Axl, WIF-1, IL-7 R alpha, GPR56, CEACAM-3, MCEMPI, FABP2, Plexin B3, MEPE, Activin RIIA, ANG-2, Cochlin, Presenilin 1, NPTXR, SLAM, COMT, SPHKI, RBP4, Nectin-1, GUSB, Nidogen-2, IL-17F, SR-AI, TAFA2, N-Cadherin, IL-17B, IL-17 RC, MIP-3b, Cystatin C, Cystatin D, AMSH, FcERI, CLECIOA, HGF R, ANG-1, Prolactin R, FGF-20, CD28, Nogo-A, HSD17B1, IL-19, Enteropeptidase, Cathepsin E, TSLP, TCN2, GDF-15, Epimorphin, GRK5, PD-1, Serpin A4, ADAM23, NOV, Galectin-2, Neurexin 3 beta, TLR3, Sirtuin 2, Numb, IL-28 R alpha, IL-33, Lin28, FCRL1, KLF4, NKp30, Lymphotactin, Cystatin SN, JAM-A, Calreticulin-2, ErbB4, BMP-8, IL-27 Ra, Fas, IL-4 Ra, Kallikrein 14, Matrilin-3, Olig2, Kallikrein 12, CA13, IL-9, Nectin-3, MPIF-1, Cystatin S, ADA, IL-2 Rb, GFR alpha-1, Smad4, ICAM-1, MEF2C, TREM-1, L-Selectin, Hepsin, CD42b, MCSF, RANK, CHST4, CA8, FCRL3, ASAH2, CF XIV, PYY, HGF, I-TAC, Semaphorin 4C, SorCS3, Tie-1, IL-31 RA, Arginase 1, POGLUT1, IL-1ra, Podoplanin, TIM-3, CREG, CD300f, uPA, EphA2, LRRTM4, LIMPII, Tenascin R, CPE, PECAM-1, DNAM-1, DKK-1, OPG, CPB1, TSH, MMP-2, Siglec-9, ICAM-3, Cystatin SA, Galectin-4, Pepsinogen II, Desmoglein-3, Nectin-4, SCF, Serpin A5, PTH, FGF-19, MSP, IL-28A, FGF-12, METAP2, ASAHL, EDIL3, NTAL, EGF R, TAFA5, Galectin-9, vWF-A2, TACE, Activin RIIB, Cathepsin S, LDL R, BMPR-IA, OX40, IL-13 R2, B7-H4, MMP-13, ANGPTL7, TRAIL R4, IGSF4B, Sirtuin 5, PEAR1, SH2D1A, Cerberus 1, GDF-11, Nrf2, TROP-2, NUDT5, ROR2, EphB4, Glypican 1, LAP (TGFb1), Gas6, Contactin-1, IL-27, UNC5H4, ICAM-2, MBL, HS3ST3B1, RCOR1, IL-10 Rb, XEDAR, IL-22, PILR-alpha, NRGi-b1, FABP4, RGM-A, RELT, TrkC, C5a, SREC-I, Nestin, TPO, ErbB3, Kirrel3, FLRT1, Galectin-3, CXCL16, JAM-B, DR6, Nogo Receptor, TLR4, VEGF R2, Tie-2, IL-15 R, Caspr2, LTbR, LAMP, ALCAM, GLP-1, NG2, IL-22 R alpha 1, AMIGO2, HCC-1, TFPI-2, ULBP-2, Desmoglein 2, Aggrecan, Syntaxin 4, VAMP-1, Nectin-2, FGF-21, Flt-3, GFAP, TIM-1, Inhibin A, Cadherin-4, PlGF-2, Neurogranin, HE4, IL-23 R, Galectin-7, GALNT3, GITR L, CD14, R-Spondin 2, CK19, Cardiotrophin-1, TREML1, HAPLN1, CD27, ANG-4, Siglec-7, CD155, VEGF-C, TNF RII, PGRP-S, SDF-1a, PDGF-AB, GPVI, CD40, SCF R, Thrombospondin-5, IL-1 RII, Neuropilin-2, Cadherin-13, E-Selectin, GITR, WISP-1, Renin, AgRP, MDL-1, ROBO3, RANTES, Endocan, Granulysin, hCGb, Mesothelin, TLR1, TRAIL, MOG, DDR1, NGF R, TRAIL R3, Trypsin 3, ARSB, LIF R alpha, BAFF R, CD157, Granzyme A, 2B4, ESAM, IL-1 R4, CXCL14, IL-31, SIRP alpha, Uromodulin, CTRC, CEACAM-1, TARC, MIP-3a, SDF-1b, NKp46, MCP-3, IL-32 alpha, TGFb3 FOLR2, CD58, IL-23, CD36, TNFb, Shh-N, Ficolin-1, Reg4, ILT2, Mer, TREM-2, Flt-3L, CD5, IL-6, CD229, Insulin, Syntaxin 6, GRO, Bcl-w, Lipocalin-2, PDGF-AA, IL-2 Ra, Angiogenin, LYVE-1, CD4, RAGE, CDNF, Brevican, NAP-2, PU.1, EDAR, ADAMTS13, Kynureninase, PTH1R, IFN-gamma R1, CrkL, B7-1, PARC, Draxin, VE-Cadherin, Procalcitonin, SOX15, Kallikrein 11, BCMA, Dectin-2, EpCAM, HCC-4, TGFa, IP-10, BLAME, CILP-1, PIGF, LOX-1, MCP-2, Resistin, HVEM, ENPP-7, Syndecan-4, IL-2 Rg, MICA, Dopa Decarboxylase, NPDC-1, MCP-4, EG-VEGF, Glycoprotein V, Semaphorin 4G, IL-12p40, PSA-total, IL-15, MAP1D, Clq, TNF4, Dtk, Endoglin, ENA-78, Reg3A, MIP-1b, FGF-17, IL-6R, IL-8, Galectin-8, CA4, Cystatin E M, FUT8, B7-H3, GCP-2, CD40L, MDC, 4-1BB, HO-1, SOST, S100A13, Kallikrein 7, and IL-13.

In some embodiments, the composition comprises one or more biomolecules that can selectively bind to a microbial antigen (such as a viral, bacterial, fungal, or parasitic antigen), block its function and/or enzymatically process the protein so it is detectable by the host immune system to then activate virus immune response to disable the virus' ability to infect cells. For example, the biomolecule can bind to a a viral antigen from a virus selected from the group consisting of Herpes Simplex virus-1 (such as, for example, glycoprotein D and/or glycoprotein G), Herpes Simplex virus-2 (such as, for example, glycoprotein D and/or glycoprotein G), Varicella-Zoster virus (such as, for example, glycoprotein E), Epstein-Barr virus (such as, for example the EBV glycoprotein), Cytomegalovirus (such as, for example the CMV glycoprotein), Human Herpes virus-6, Variola virus, Vesicular stomatitis virus, Hepatitis A virus, Hepatitis B virus (including, but not limited to the hepatitis B virus surface antigen), Hepatitis C virus (such as, for example, the Hepatitis C E1, E2, or E3 proteins), Hepatitis D virus, Hepatitis E virus, Rhinovirus, Coronavirus (including, but not limited to spike or envelope proteins from avian coronavirus (IBV), porcine coronavirus HKU15 (PorCoV HKU15), Porcine epidemic diarrhea virus (PEDV), HCoV-229E, HCoV-OC43, HCoV-HKU1, HCoV-NL63, SARS-CoV, SARS-CoV-2 (including, but not limited to the B1.351 variant, B.1.1.7 variant, and P.1 variant), or MERS-CoV), Influenza virus A (such as, for example the hemagglutinin (HA) protein including the HA1 and HA2 protein and including trimeric HA), Influenza virus B (such as, for example the hemagglutinin (HA) protein including the HA1 and HA2 protein and including trimeric HA), Measles virus (such as, for example the hemagglutinin protein), Polyomavirus, Human Papilomavirus, Respiratory syncytial virus (such as, for example the RSV G protein), Adenovirus, Coxsackie virus, Dengue virus (such as, for example capsid protein, envelope protein, and/or premembrane/membrane protein), Mumps virus, Poliovirus, Rabies virus (including, but not limited to the Rabies glycoprotein), Rous sarcoma virus, Reovirus, Yellow fever virus, Zika virus (such as, for example capsid protein, envelope protein, and/or premembrane/membrane protein), Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A (including, but not limited to viral protein 4 and viral protein 7), Rotavirus B (including, but not limited to viral protein 4 and viral protein 7), Rotavirus C (including, but not limited to viral protein 4 and viral protein 7), Sindbis virus, Simian Immunodeficiency virus, Human T-cell Leukemia virus type-1, Hantavirus, Rubella virus, Simian Immunodeficiency virus, Human Immunodeficiency virus type-1 (such as, for example, glycoprotein (gp), envelope protein (Env), or gag protein), and Human Immunodeficiency virus type-2. For example, the presence of furin protein in the invention may enable enzymatic processing of shed viral particle spike protein to the upright immune-detectable conformation, improving immune response to degrade extracellular viral particles. Additionally, for example, the composition can comprise a ferritin protein content effective to increase IL-10 secretion by immune regulatory cells to inhibit hyperactive immune cell actions, collectively referred to as a cytokine storm or the protein PAI-1 that can block production of plasmin to inhibit the "bradykinin storm." The biomolecule of the composition can also comprise thrombomodulin, which can suppress micro-blood clotting frequency, reducing pathogenic clotting, and reduce thrombotic emboli; and other protein components that inhibit NETosis (neutrophil induced nucleic acid-protein networks intended to capture pathogenic invading species, for example, viruses, and bacteria within the vasculature)

Extracellular vesicles (EV) are small membrane bound spheres containing proteins and RNA (of which exosomes are a subset). Exosomes are small (e.g., 20-150 nm) diameter lipid bilayer vesicles secreted by cells to enable paracrine communication. Other EV populations are derived directly from the plasma membrane or are formed during apoptosis (apoptotic bodies). Recently, miRNA sequences homologous with the sequence of SARS-CoV-2 RNA were compared and a list of miRNAs were identified that appear able to bind to the viral sequence in the 3' untranslated region, which has a low mutation rate. Therefore, the miRNA should be effective in their action against multiple variants of the virus. Accordingly, in some embodiments, the biomolecule of the composition comprises a micro RNA content that may bind to RNA sequences of a microbe and block translation from or activate degradation of the microbial RNA sequence. The composition thereby may reduce microbial replication rate (including, but not limited to viral replication rate) and reduce host cell death. For example, disclosed herein are compositions comprising a therapeutically effective amount of an MSC secretome (such as, for example, including, but not limited to MSC growth factor, MSC exosome, MSC extracts and/or extracellular vesicle comprising compositions) and one or more biomolecules comprise a miRNA is selected from the group of miRNA comprising hsa-let-7a-5p, hsa-let-7b-5p, hsa-let-7c-5p, hsa-let-7d-3p, hsa-let-7e-5p, hsa-let-7g-5p, hsa-let-7i, hsa-let-7i-5p, hsa-miR-100-5p, hsa-miR-103a-3p, hsa-miR-106a-5p, hsa-miR-106b-5p, hsa-mir-10b, hsa-miR-10b-5p, hsa-mir-1246, hsa-miR-1246, hsa-miR-125a-5p, hsa-miR-125b-5p, hsa-miR-130a-3p, hsa-mir-130b, hsa-miR-130b-3p, hsa-miR-132-3p, hsa-miR-136-5p, hsa-miR-138-5p, hsa-miR-139-5p, hsa-mir-140, hsa-miR-140-3p, hsa-miR-145-5p, hsa-mir-146a, hsa-miR-146a-5p, hsa-miR-148a-3p, hsa-miR-152-3p, hsa-miR-15a-5p, hsa-miR-15b-5p, hsa-mir-16-1, hsa-mir-16-2, hsa-miR-16-5p, hsa-miR-17-5p, hsa-miR-181a-5p, hsa-miR-191-5p, hsa-miR-193a-5p, hsa-miR-193b-3p, hsa-miR-197-3p, hsa-miR-199a-3p, hsa-miR-199a-5p, hsa-miR-199b-5p, hsa-miR-19a-3p, hsa-miR-19b-3p, hsa-miR-20a-5p, hsa-mir-203a, hsa-miR-203a-3p, hsa-miR-214-3p, hsa-mir-21, hsa-miR-21-3p, hsa-miR-21-5p, hsa-mir-221, hsa-miR-221-3p, hsa-mir-222, hsa-miR-222-3p, hsa-miR-22-3p, hsa-miR-23a-3p, hsa-miR-23b-3p, hsa-mir-24-1, hsa-mir-24-2, hsa-miR-24-3p, hsa-mir-25, hsa-miR-25-3p, hsa-miR-26a-5p, hsa-miR-27a-3p, hsa-mir-27b, hsa-miR-27b-3p, hsa-miR-29a-3p, hsa-miR-29c-3p, hsa-miR-30a-5p, hsa-miR-30a-5p, hsa-miR-30b-5p, hsa-miR-30c-5p, hsa-mir-30d, hsa-miR-30d-5p, hsa-mir-30e, hsa-miR-30e-5p, hsa-miR-31-3p, hsa-miR-31-5p, hsa-miR-320a, hsa-miR-342-3p, hsa-miR-345-5p, hsa-miR-34a-5p, hsa-miR-361-5p, hsa-miR-376a-3p, hsa-miR-376c-3p, hsa-miR-423-3p, hsa-miR-423-5p, hsa-miR-424-5p, hsa-miR-484, hsa-mir-486-1, hsa-mir-486-2, hsa-miR-486-5p, hsa-miR-570-3p, hsa-miR-574-3p, hsa-miR-663a, hsa-miR-874-3p, hsa-mir-92a-1, hsa-mir-92a-2, hsa-miR-92a-3p, hsa-miR-92b-3p, hsa-mir-93, hsa-miR-93-5p, hsa-miR-940, hsa-miR-99a-5p, and hsa-miR-99b-5p.

In some embodiments, the composition comprises miRNA (such as hsa-miR-19a-3p, hsa-miR-19b-3p) that can be effective to inhibit translation of Bradykinin receptor 2, which is critical for activation of bradykinin signaling responsible for severe vascular response to coronavirus infection.

In some embodiments, the composition comprises microRNA that can inhibit translation of Kallikrein B1 (such as hsa-miR-24-3p) and other Kallikrein proteins involved in proteolytic digestion of the bradykinin precursor protein to generate bradykinin peptide.

In some embodiments, the biomolecule of the composition comprises microRNA content that can inhibit translation of cellular proteins involved in enabling virus fusion to the cell membrane using the angiotensin-converting enzyme 2 (ACE 2) receptor protein or by blocking activity of proteins activated through the process of the virus binding to the ACE 2 receptor protein. For example, the transmembrane protease, serine 2 (TMPRSS2) enzyme can be inhibited. TMPRSS2 is required to enable SARS-CoV-2 spike protein to interact with the ACE 2 Receptor and initiate membrane fusion. Exemplary microRNA content may include human miRNA sequences hsa-let-7a-5p, hsa-let-7b-5p, hsa-let-7c-5p, hsa-let-7g-5p, hsa-let-7i-5p, hsa-miR-214-3p, and hsa-miR-27a-3p, which all have binding sites in mRNA for TMPRSS2.

In some embodiments, the biomolecule of the composition comprises microRNA that can inhibit proteins of the bradykinin pathway. For example, the microRNA sequences hsa-let-7a-5p, hsa-let-7b-5p, hsa-let-7c-5p, hsa-let-7g-5p, hsa-let-7i-5p, hsa-let-7i, hsa-miR-106a-5p, hsa-miR-106b-5p, hsa-miR-15a-5p, hsa-miR-15b-5p, hsa-miR-16-5p, hsa-miR-17-5p, hsa-miR-20a-5p, hsa-miR-23a-3p, hsa-miR-23b-3p, hsa-mir-24-1, hsa-mir-24-2, hsa-miR-25-3p, hsa-miR-92a-3p, hsa-miR-92b-3p, and hsa-miR-93-5p may bind and prevent translation of hyaluronan synthase 2, thereby preventing formation of Hyaluronic acid complexes in the lungs. Hyaluronic acid complexes block oxygen exchange in the alveoli.

In some embodiments, the biomolecule of the composition comprises a microRNA content, a protein content, or a combination thereof that can inhibit a cytokine storm. The composition may inhibit the cytokine storm by (i) inhibiting translation of cytokine proteins by binding mRNA sequences for those proteins, (ii) sterically hindering ligand/receptor interactions, (iii) enzymatically altering ligands or receptors to inhibit their pro-inflammatory actions, or (iv) activating inhibitory proteins, lipids or RNA sequences that inhibit the proinflammatory cytokines such as, but not limited to, IL-1beta, IL-6, TNF-alpha, GM-CSF, M-CSF. For example, human miRNA sequences hsa-let-7a-5p, hsa-let-7b-5p, hsa-let-7c-5p, hsa-let-7g-5p, hsa-let-7i-5p, and hsa-miR-547-3p are able to bind IL-6 mRNA, while hsa-miR-130a-3p and hsa-miR-181a-5p can inhibit translation of TNF-alpha.

It is understood and herein contemplated that the MSC secretome comprises exosomes and growth factors. The growth factors and exosomes can be allogenic or autogenic. The growth factors and exosomes can be derived from any cell in the human body, such as from ectodermal cells, endodermal cells, or mesodermal cells. For example, the MSC secretomes may comprise mesenchymal stem cell (MSC) derived growth factors, MSC derived exosomes, or both MSC derived growth factors and exosomes. In some embodiments, the method further comprises adding at least one additive with the exosomes and growth factors. Specifically, MSCs under appropriate wound healing conditions may produce suitable therapeutic agents, such as exosomes and growth factors, that can provide therapy for inflammatory lung diseases. In one aspect, disclosed herein are compositions, wherein the MSC secretome composition further comprises prostaglandin E2 (PGE2), transforming growth factor β1 (TGF-β1), hepatocyte growth factor (HGF), stromal cell derived factor-1 (SDF-1), nitric oxide, indoleamine 2,3-dioxygenase, interleukin-4 (IL-4), IL-6, interleukin-10 (IL-10), IL-1 receptor antagonist and soluble TNF-α receptor, insulin-like growth factors, fibroblast growth factors (FGF) 1-23 (especially, FGF1 and FGF2), bone morphogenetic proteins (BMPs) 1-15, epidermal growth factor (EGF), transforming growth factor-α (TGF-α) macrophage-stimulating protein (MSP), platelet derived growth factor (PLGF), vascular endothelial growth factor (VEGF), macrophage colony stimulating factor (M-CSF), insulin, granulocyte colony stimulating factor (G-CSF), granulocyte macrophage colony stimulating factor (GM-CSF estrogen, and/or thyroid hormones.

As noted above, the composition comprises proteins and microRNAs, some of which may be embedded in or surrounded by a lipid membrane to create vesicles in the size range of about >20 nm to about 200 nm in size. The number of vesicles within the invention may range between about 1 million to about 100 billion vesicles per mL when suspended or about 10 million to about 1 trillion when formulated as a lyophilized powder.

1. Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism such as, for example, a metered-dose inhaler, a dry powder inhaler, a nebulizer, a vaporization device, or the like. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129:57-80, (1992); and Roffler, et al., *Biochem. Pharmacol*, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis have been reviewed (Brown and Greene, DNA and Cell Biology 10:6, 399-409 (1991)).

a) Pharmaceutically Acceptable Carriers

The compositions, including antibodies, can be used therapeutically in combination with a pharmaceutically acceptable carrier.

Suitable carriers and their formulations are described in Remington: *The Science and Practice of Pharmacy* (19th ed.) ed. A. R. Gennaro, Mack Publishing Company, Easton, PA 1995. Typically, an appropriate amount of a pharmaceutically-acceptable salt is used in the formulation to render the formulation isotonic. Examples of the pharmaceutically-acceptable carrier include, but are not limited to, saline, Ringer's solution, and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 μg/kg to up to 100 mg/kg of body weight or more per day, depending on the factors mentioned above.

C. Mesenchymal Stem Cells

As noted throughout, the treatment compositions disclosed herein can utilize MSC secretomes and/or growth factors derived from mesenchymal stem cells (MSCs). While allogenic cellular MSC IV infusion treatments have been widely pursued, there are numerous safety and regulatory concerns surrounding allogenic cellular preparations. The inherent problems with IV infusions of living MSCs include the trapping of the cells in the lungs, causing the cells to die within 24 hours. The cellular debris from this cell death is transported to the liver and spleen, where it is disposed. Current autogenous treatments from bone marrow concentrate only deliver a few thousand MSCs. While allogenic expanded MSC IV infusions can deliver hundreds of millions of living MSCs, they get trapped in the lungs and die. The long-term effect of introducing the foreign DNA into the recipient is unclear and questions have arisen on whether introducing the large amount of foreign DNA could be carcinogenic.

Existing autogenous and allogeneic MSCs contained within bone marrow, bone marrow concentrate, synovia-derived mesenchymal stem cells (MSCs), or adipose-derived stromal vascular fraction (SVF) or various post-natal products from umbilical cord, placenta or amnion, expanded MSC cultures are currently being used to treat wounds, orthopedic pathology, and spine pathology. To avoid recognition by the immune system, undifferentiated MSCs express low to medium levels of human leukocyte antigen (HLA) Class I and low levels of HLA Class II. This property gives donor MSCs a so-called 'stealth' ability to go undetected by a host immune system in allogeneic therapies. However, Class I antigen is present at detectable levels and Class II antigen expression can be induced by INF-γ. Several cases of allogeneic MSC rejection and chronic immune responses have been reported in animal studies and human clinical trials. This entire problem could be avoided by using only the mesenchymal stem cell secretomes, including, but not limited to growth factors, proteins, peptides, glycosaminoglycans, proteoglycans, chemokines, cytokines, extracts, extracellular vesicles, and/or exosomes collected from the conditioned growth media. An acellular versus a cellular MSC product In fact, prior to the present disclosure an active MSC growth factor product that can be used for these applications has not been developed. Thus, in one aspect, disclosed herein are MSC secretome compositions (including, but not limited to MSC growth factor, MSC exosome, MSC extracts and/or extracellular vesicle comprising compositions) for use in the treatment, inhibition, decrease, reduction, amelioration, and/or prevention of a microbial infection, symptoms of said infection, or secondary conditions (such as, for example, microbial initiated cytokine storm, microbial infection initiated bradykinin storm, and/or microbial infection induced acute respiratory distress syndrome), said treatment compositions comprising (i) a growth factor powdered additive comprising a mesenchymal stem cell (MSC) derived preparation (including, but not limited to a MSC secretome composition) and (ii) a pharmaceutically acceptable carrier.

As noted above, MSC are multipotent cells that have the ability to differentiate into a multitude of cell types including myocytes, chondrocytes, adipocytes, and osteoblasts. Typically, these cells can be found in the placenta, umbilical cord blood, adipose tissue, bone marrow, or amniotic fluid, including perivascular tissue. As used herein, "MSC" refers to non-terminally differentiated cells including but not limited to multipotential stem cell, multipotential stromal cell, stromal vascular cells, pericytes, perivascular cells, stromal cells, pluripotent cells, multipotent cells, adipose-derived fibroblast-like cells, adipose-derived stromal vascular fraction, adipose-derived MSC, bone marrow-derived fibroblast-like cells, bone marrow-derived stromal vascular fraction, bone marrow-derived MSC, tissue-derived fibroblast-like cells, adult stem cells, adult stromal cells, keratinocytes, and/or melanocytes.

It has been long recognized that MSC, in addition to their differentiation potential, have the immunomodulatory abilities resulting in the expression of many different cytokines and growth factors. As used herein, a "MSC preparation" or "MSC secretome composition" refers to a composition comprising MSC growth factors, MSC exosomes, extracellular vesicles, extracellular vesicle isolate product (EVIP), or acellular extracts of MSCs and/or MSC lysates obtained from human MSCs, fibroblast-like cells, and non-human animal MSCs including, but not limited to MSCs from horses, cows, pigs, sheep, non-human primates, dogs, cats, rabbits, rats, and mice. In embodiments, the MSCs may be derived from the patient to which the composition will be applied (autologous) or derived from another individual (allogeneic). The MSCs may be culture expanded to collect the conditioned media or to increase the quantity of cells for the lysate or used freshly prior to incorporation into the composition of the present disclosure.

The MSC secretome compositions (including, but not limited to MSC growth factor, MSC exosome, MSC extracts and/or extracellular vesicle comprising compositions) may comprise about 0.00001 to about 20 wt. %, such as from about 0.01 to about 10 wt. %, of a mesenchymal stem cell (MSC) extract, MSC exosome, or MSC growth factor preparation. The MSC preparation may comprise either MSC conditioned media or MSC lysate from cell culture expanded MSCs. In some embodiments, the composition may further comprise from about 0.01 to about 10 wt. % of a cell-free medium conditioned by growth of MSCs or MSC lineage cells, wherein the cells are cultured under normal hyperoxic culturing conditions or under artificial wound healing conditions.

As disclosed herein the MSCs used to produce the disclosed MSC additives (including growth factor secretome composition either frozen or powdered additives) can be selectively stimulated to produce MSC growth factors, secretomes, cytokines, chemokines, mesenchymal stem cell proteins, peptides, glycosaminoglycans, extracellular matrix (ECM), proteoglycans, secretomes, and exosomes. The growth factors and exosomes may be derived from any cell in the human body, such as from ectodermal cells, endodermal cells, or mesodermal cells. As used herein, MSC growth factors include but are not limited to prostaglandin E2 (PGE2), transforming growth factor $\beta1$ (TGF-$\beta1$), hepatocyte growth factor (HGF), stromal cell derived factor-1 (SDF-1), nitric oxide, indoleamine 2,3-dioxygenase, interleukin-4 (IL-4), IL-6, interleukin-10 (IL-10), IL-1 receptor antagonist and soluble TNF-$\alpha$ receptor, insulin-like growth factors, fibroblast growth factors (FGF) 1-23 (especially, FGF1 and FGF2), bone morphogenetic proteins (BMPs) 1-15, epidermal growth factor (EGF), transforming growth factor-$\alpha$ (TGF-$\alpha$) macrophage-stimulating protein (MSP), platelet derived growth factor (PLGF), vascular endothelial growth factor (VEGF), macrophage colony stimulating factor (M-CSF), insulin, granulocyte colony stimulating factor (G-CSF), granulocyte macrophage colony stimulating factor (GM-CSF), as well as hormones including estrogen, and thyroid hormones.

As mentioned above, culturing the MSCs may occur under normal hyperoxic culturing conditions or under wound healing hypoxic conditions. Hyperoxic conditions may comprise of approximately 21% oxygen with or without serum supplements, while hypoxic conditions may comprise about 1% to about 5% oxygen with inflammatory cytokines, angiogenic factors, reduced serum, reduced glucose or these elements in various combinations. The combined reduced nutrient and metabolite environment may trigger the cultured cells to produce wound healing and anti-inflammatory ECM proteins and growth factors to direct tissue healing. Direct tissue healing likely is in the form of new ECM proteins, such as collagen and glycosaminoglycans (GAGs), as well as growth factors and cytokines. In one aspect, the MSC preparation (such as, for example, a MSC secretome composition) comprises MSC growth factors, MSC exosomes, and/or cellular extracts of MSCs or MSC lysates obtained from MSCs cultured under standard hyperoxic culturing conditions (for example, 21% oxygen) or MSCs cultured under artificial wound healing conditions (such as, for example, 0.1% to about 5% oxygen in the presence of inflammatory cytokines, angiogenic factors, and reduced glucose).

As disclosed herein artificial wound healing conditions simulate growth conditions in real wounds where there is a reduction in nutrient supply and reduction of waste removal that is usually caused by a disruption in local blood circulation. This creates a harsh environment for cells until new blood vessels are created and blood circulation is restored. Accordingly, artificial wound healing conditions used to culture MSCs can include one or more of the following growth conditions reduction in glucose availability, reduction in oxygen tension, reduction in pH, and increased temperature.

In one aspect, the glucose availability can be reduced relative to normal control. Modified culture media to reduce glucose, but not damage the cells can be between 0 and 50% reduction in glucose, more preferably between about 5% and 40% reduction in glucose. For example, MSC artificial wound healing culture conditions can comprise glucose reduction of about 1, 2, 3, 4, 5, 6, 7, 8 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50% such as a glucose reduction from about 5% to about 15%, from about 10% to about 20%, from about 15% to about 25%, from about 20% to about 30%, or from about 25% to about 35%.

In one aspect, oxygen tension can be reduced to oxygen levels to hypoxic conditions. Normal atmospheric oxygen is approximately 21% and any reduction is considered hypoxic. Thus, in one aspect, MSCs can be cultured at between 0.0% and 2.9% oxygen, from about 0.1% to about 0.5% oxygen, from about 0.1% to about 2.0%, from about 0.1% to about 5.0% oxygen, from about 0.5% to 5.0%, from about 1.0% to about 10% oxygen, about 5.0% to about 10.0% oxygen; and from about 10.0% to about 15.0% under artificial wound healing conditions. Preferably during MSC would healing culture conditions oxygen tension is between about 0.5% and 20.5% oxygen, such as, for example, 0, 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.7, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, or 20.5% oxygen.

The pH can also be reduced under artificial wound healing conditions. Physiologic pH is maintained very tightly and is usually very close to a neutral pH=7.2±0.2 (7.0-7.4). However, in a wound the acidic environment can have a pH=6.2±0.2 (i.e., a pH from 6.0 to about 6.4). Thus, under artificial wound healing culture conditions, pH can be from about 6.0 to about 7.4, for example, from 6.0 to about 6.4, from about 6.2 to about 6.4, from about 6.2 to about 6.6, from about 6.4 to about 6.6, from about 6.4 to about 6.8, or from about 6.6 to about 7.0, such as 6.0, 6.1, 6.2, 6.3, 6.4, 6.5, 6.6, 6.7, 6.8, 6.9, 7.0, 7.1, 7.2, 7.3 or 7.4.

Under artificial wound healing culture conditions, the temperature of the culture environment may be raised to simulate temperature increases at the site of a wound. Physiologic homeostasis temperature is maintained at 37° C. (98.6° F.). A slight increase or decrease can cause significant changes to cellular metabolism. By increasing the temperature above 37° C. to any temperature up to about 40° C. (104° F.) can create an "feverous" environment. Thus, in on aspect, the artificial wound healing culture conditions for the MSCs can comprise from about 35° C. to about 39° C., from about 35° C. to about 36° C., from about 36° C. to about 37° C., from about 37° C. to about 38° C., from about 38° C. to about 39° C., from about 39° C. to about 40° C. In one aspect, the temperature of the artificial wound healing culture can be 35.0, 35.1, 35.2, 35.3, 36.4, 35.5, 35.6, 35.7, 35.8, 35.9, 36.0, 36.1, 36.2, 36.3, 36.4, 36.5, 36.6, 36.7, 36.8, 36.9, 37.0, 37.1, 37.2, 37.3, 37.4, 37.5, 37.6, 37.7, 37.8, 37.9, 38.0, 38.1, 38.2, 38.3, 38.4, 38.5, 38.6, 38.7, 38.8, 38.9, 39.0, 39.1, 39.2, 39.3, 39.4, 39.5, 39.6, 39.7, 39.8, 39.9, or 40.0° C.

In one aspect, the MSC secretome compositions (including, but not limited to MSC growth factor, MSC exosome, MSC extracts and/or extracellular vesicle comprising compositions) can further comprise a protective coating (such as, for example, a cryoprotectant oligosaccharide and a protein solution) to reduce degradation of the growth factors. It is understood and herein contemplated that the protective coating can be engineered as a polymer. "Polymer" refers to a relatively high molecular weight organic compound, natural or synthetic, whose structure can be represented by a repeated small unit, the monomer. Non-limiting examples of polymers include polyethylene, rubber, cellulose. Synthetic polymers are typically formed by addition or condensation polymerization of monomers. The term "copolymer" refers to a polymer formed from two or more different repeating units (monomer residues). By way of example and without limitation, a copolymer can be an alternating copolymer, a random copolymer, a block copolymer, or a graft copolymer. It is also contemplated that, in certain aspects, various block segments of a block copolymer can themselves comprise copolymers. The term "polymer" encompasses all forms of polymers including, but not limited to, natural polymers, synthetic polymers, homopolymers, heteropolymers or copolymers, addition polymers, etc. In one aspect, the gel matrix can comprise copolymers, block copolymers, diblock copolymers, and/or triblock copolymers.

In one aspect, the protective coating can comprise a biocompatible polymer. In one aspect, biocompatible polymer can be crosslinked. Such polymers can also serve to slowly release the adipose browning agent and/or fat modulating agent into tissue. As used herein biocompatible polymers include, but are not limited to polysaccharides; hydrophilic polypeptides; poly(amino acids) such as poly-L-glutamic acid (PGS), gamma-polyglutamic acid, poly-L-aspartic acid, poly-L-serine, or poly-L-lysine; polyalkylene glycols and polyalkylene oxides such as polyethylene glycol (PEG), polypropylene glycol (PPG), and poly(ethylene oxide) (PEO); poly(oxyethylated polyol); poly(olefinic alcohol); polyvinylpyrrolidone); poly(hydroxyalkylmethacrylamide); poly(hydroxyalkylmethacrylate); poly(saccharides); poly(hydroxy acids); poly(vinyl alcohol), polyhydroxyacids such as poly(lactic acid), poly (gly colic acid), and poly (lactic acid-co-glycolic acids); polyhydroxyalkanoates such as poly3-hydroxybutyrate or poly4-hydroxybutyrate; polycaprolactones; poly(orthoesters); polyanhydrides; poly (phosphazenes); poly(lactide-co-caprolactones); polycarbonates such as tyrosine polycarbonates; polyamides (including synthetic and natural polyamides), polypeptides, and poly(amino acids); polyesteramides; polyesters; poly (dioxanones); poly(alkylene alkylates); hydrophobic polyethers; polyurethanes; polyetheresters; polyacetals; polycyanoacrylates; polyacrylates; polymethylmethacrylates; polysiloxanes; poly(oxyethylene)/poly(oxypropylene) copolymers; polyketals; polyphosphates; polyhydroxyvalerates; polyalkylene oxalates; polyalkylene succinates; poly (maleic acids), as well as copolymers thereof. Biocompatible polymers can also include polyamides, polycarbonates, polyalkylenes, polyalkylene glycols, polyalkylene oxides, polyalkylene terepthalates, polyvinyl alcohols (PVA), methacrylate PVA(m-PVA), polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly (methyl methacrylate), poly(ethylmethacrylate), poly(butylmethacrylate), poly(isobutylmethacrylate), poly(hexlmethacrylate), poly(isodecylmethacrylate), poly(lauryl methacrylate), poly (phenyl methacrylate), poly (methyl acrylate), poly(isopropyl acrylate), poly(isobutyl acrylate), poly(octadecyl acrylate), polyethylene, polypropylene, poly(ethylene glycol), poly(ethylene oxide), poly (ethylene terephthalate), poly(vinyl alcohols), poly(vinyl acetate, poly vinyl chloride polystyrene and polyvinylpyrrolidone, derivatives thereof, linear and branched copolymers and block copolymers thereof, and blends thereof. Exemplary biodegradable polymers include polyesters, poly (ortho esters), poly(ethylene amines), poly(caprolactones), poly(hydroxybutyrates), poly(hydroxyvalerates), polyanhydrides, poly(acrylic acids), polyglycolides, poly(urethanes), polycarbonates, polyphosphate esters, polyphospliazenes, derivatives thereof, linear and branched copolymers and block copolymers thereof, and blends thereof.

In some embodiments the protective coating comprises carbohydrate construction of monosaccharides as well as carbohydrate polymers such as disaccharides or polysaccharides including but not limited to non-reducing poly or disaccharides as well as any combination thereof. Examples of carbohydrates that can be used in the protective coating comprise Glucose, Aldoses (D-Allose, D-Altrose, D-Mannose, etc.), Glucopyranose, Pentahydroxyhexanal, α-D-Glucopyranosyl-D-glucose, α-D-Glucopyranosyl-dihydrate, Polymer of β-D-Glycopyranosyl units, β-D-Fructofuranosyl α-D-glucopyranoside (anhydrous/dihydrate), β-D-Galactopyranosyl-D-glucose, α-D-Glucopyranosyl-α-D-glucopyranoside (anhydrous/dihydrate), Galactose, Pentoses (Ribose, xylose, lyxose), Dextrose, Dodecacarbon monodecahydrate, Fructose, Sucrose, Lactose, Maltose, Trehalose, Agarose, D-galactosyl-β-(1-4)-anhydro-L-galactosyl, Cellulose, Polymer of β-D-Glycopyranosyl units, and Starch, as well as, Polyhydric alcohols, Polyalcohols, Alditols, Erythritol, Glycitols, Glycerol, Xylitol, and Sorbitol.

In some embodiments the protective coating contains biocompatible and/or biodegradable polyesters or polyanhydrides such as poly(lactic acid), poly(glycolic acid), and poly(lactic-co-glycolic acid). The particles can contain one more of the following polyesters: homopolymers including glycolic acid units, referred to herein as "PGA", and lactic acid units, such as poly-L-lactic acid, poly-D-lactic acid, poly-D,L-lactic acid, poly-L-lactide, poly-D-lactide, and poly-D,L-lactide5 collectively referred to herein as "PLA", and caprolactone units, such as poly(e-caprolactone), collectively referred to herein as "PCL"; and copolymers including lactic acid and glycolic acid units, such as various forms of poly(lactic acid-co-glycolic acid) and poly(lactide-co-glycolide) characterized by the ratio of lactic acid:glycolic acid, collectively referred to herein as "PLGA"; and polyacrylates, and derivatives thereof. Exemplary polymers also include copolymers of polyethylene glycol (PEG) and the aforementioned polyesters, such as various forms of PLGA-PEG or PLA-PEG copolymers, collectively referred to herein as "PEGylated polymers". In certain embodiments, the PEG region can be covalently associated with polymer to yield "PEGylated polymers" by a cleavable linker. In one aspect, the polymer comprises at least 60, 65, 70, 75, 80, 85, 89, 90, 91, 92, 93, 94, 95, 96, 97, 98, or 99 percent acetal pendant groups.

The triblock copolymers disclosed herein comprise a core polymer such as, example, polyethylene glycol (PEG), polyvinyl acetate, polyvinyl alcohol, polyvinyl pyrrolidone (PVP), polyethyleneoxide (PEO), poly(vinyl pyrrolidone-co-vinyl acetate), polymethacrylates, polyoxyethylene alkyl ethers, polyoxyethylene castor oils, polycaprolactam, polylactic acid, polyglycolic acid, poly(lactic-glycolic) acid, poly(lactic co-glycolic) acid (PLGA), cellulose derivatives, such as hydroxymethylcellulose, hydroxypropylcellulose and the like.

Examples of diblock copolymers that can be used in the protective coatings disclosed herein comprise a polymer such as, example, polyethylene glycol (PEG), polyvinyl acetate, polyvinyl alcohol (PVA), polyvinyl pyrrolidone (PVP), polyethyleneoxide (PEO), poly(vinyl pyrrolidoneco-vinyl acetate), polymethacrylates, polyoxyethylene alkyl ethers, polyoxyethylene castor oils, polycaprolactam, polylactic acid, polyglycolic acid, poly(lactic-glycolic) acid, poly(lactic co-glycolic) acid (PLGA).

In one aspect, the protective coating contains (i.e., the encapsulated, the encapsulated compositions can further comprise lecithin or hydrolyzed lecithin as a carrier or as encapsulation material. As used herein, lecithin and/or hydrolyzed lecithin coatings include coatings comprising phosphatidyl choline, phosphatidyl inositol, phosphatidyl ethanolamine, phosphatidylserine, and phosphatidic acid. Sources of the lecithin can be pnat or animal sources.

In one aspect, any of the polymers, monosaccharides, disaccharides, or polysaccharides used to form the protective coating formed by placing the MSC additive in an encapsulating solution can be at an appropriate concentration for form the protective coating. For example, polymers, monosaccharides, disaccharides, or polysaccharides can be at any concentration between 0.01 mM and 10.0 M concentration, for example, from about 0.01M to about 0.1M, from about 0.1 mM to about 1.0 M, from about 1.0 M to about 10.0 M. Exemplary concentrations include 0.01, 0.02, 0.03, 0.04, 0.05, 0.06, 0.07, 0.08, 0.09, 0.1, 0.2, 0.3, 0.4, 0.4, 0.6, 0.7, 0.8, 0.9, 1, 2, 3, 4, 5, 6, 7, 8, 9, 10, 20, 30, 40, 50, 60, 70, 80, 90, 100, 110, 120, 130, 140, 150, 160, 170, 180, 190, 200, 225, 250, 275, 300, 325, 350, 375, 400, 450, 500, 600, 700, 800, 900 mM, 1, 1.1, 1.2, 1.3, 1.4, 1.5, 1.6, 1.7, 1.8, 1.9, 2, 3, 4, 5, 6, 7, 8, 9, 10M.

In one aspect, the MSC secretome compositions (including, but not limited to MSC growth factor, MSC exosome, MSC extracts and/or extracellular vesicle comprising compositions) disclosed herein may comprise any known ingredients typically found pharmaceutical fields such as agents for combating free radicals; bactericides; sequestering agents; preservatives; basifying or acidifying agents; fragrances; surfactants; fillers; natural products or extracts of natural product, such as aloe or green tea extract; vitamins; or coloring materials. Other ingredients that may be combined with the powder may include an antioxidant, which can be selected from a variety of antioxidants. Suitable antioxidants include vitamins, such as Vitamin C (L-Ascorbate, Ascorbate-2 Phosphate magnesium salt, Ascorbyl Palmitate, Tetrahexyldecyl Ascorbate), Vitamin E (Tocotrienol), Vitamin A (retinol, retinal, retinoic acid, provitamin A carotenoids, such as beta-carotene), N-acetyl glucosamine, or other derivatives of glucosamine. Other ingredients may include at least one essential fatty acid, such as Ω-3, Ω-6, and Ω-9 polyunsaturated fatty acids, such as linoleic acid (LA), gamma-linoleic acid (GLA), alpha-linoleic acid (ALA), dihomo-y-linolenic acid (DGLA), arachidonic acid (ARA), and others. The fatty acids may be derived from various sources including evening primrose oil, black currant oil, borage oil, or GLA modified safflower seeds. Other ingredients may include a platelet rich fibrin matrix, at least one ingredient to support ECM production and production of hyaluronic acid, such as N-acetyl glucosamine or other derivatives of glucosamine, ultra-low molecular weight (ULMW) hyaluronic acid, chondroitin sulfate, or keratin sulfate.

Producing the MSC secretome compositions can comprise culturing MSCs collected from a donor to create a cultured media under culturing conditions selected from the group consisting of normal hyperoxic culturing conditions and wound healing hypoxic conditions including reduced oxygen and nutrition; stimulating the cultured cells to selectively secrete desired anti-inflammatory proteins, peptides, glycosaminoglycans, proteoglycans exosomes, and secretomes by adjusting the cell growth conditions; collecting, combining the conglomerate mixture with an encapsulation solution, and freezing the conglomerate mixture, wherein the conglomerate mixture comprises exosomes, peptides, proteins, cytokines, growth factors, extracellular matrix (ECM), proteoglycans, glycosaminoglycans; and chemokines selected from the group consisting of human MSCs, animal MSCs, multipotential stromal cells, fibroblasts, and fibroblast cells; combining the conglomerate mixture with an encapsulation solution, such as oligosaccharides, like a trehalose solution or protein solution and freezing the mixture; and lyophilizing or freeze-drying the frozen mixture, creating a dry powder. Alternatively, the MSCs may be lysed to collect all of the MSCs from the culture process, creating an extracted lysate; concentrating the extracted lysate and combining the extracted lysate with an encapsulation solution, such as oligosaccharides like a trehalose solution or protein solution and freezing the mixture; and lyophilizing or freeze-drying the frozen mixture, creating a dry powder. The powder contains a highly concentrated collection of analgesic MSC secretomes and exosomes and extracellular matrix components that are specific to anti-inflammation.

The method may also include filter-sterilizing, concentrating, freezing, or freeze drying the MSC conditioned culture medium. Additionally, the MSC culture medium may be combined with a cryoprotectant prior to freezing.

There are various methods for lysing the MSCs. Lysing may be achieved by the addition of a hypotonic solution or repeated freeze-thaw processes to disrupt the cell membranes. Moreover, the cells may be lysed while attached to the culture surface or in suspension. The cells may also be enzymatically released and/or lysed by mechanical homogenization.

Stimulating the MSC to selectively secrete the desired anti-inflammatory proteins, peptides, glycosaminoglycans, proteoglycans, exosomes and secretomes may be achieved by adjusting the cell growth conditions, such as cell confluency, culture media supplements, nutritional supplements, oxygen levels, length of culture in those conditions, cell passage number or combinations of those, and the like.

D. Methods of Treating Microbial Infections and/or Symptoms Thereof

In one aspect, it is understood and herein contemplated that the disclosed comprising a therapeutically effective amount of a MSC secretome (such as, for example, including, but not limited to MSC growth factor, MSC exosome, MSC extracts and/or extracellular vesicle comprising compositions) and one or more biomolecules (such as, for example, a peptide, polypeptide, protein, siRNA, shRNA, and/or microRNA (miRNA)) that selectively bind to one or more microbial immunogens, or inhibit the ability of a microbe to inhabit a host, or inhibit, decrease, reduce, ameliorate, and/or prevent one or more secondary conditions caused by a microbial infection (such as, for example, comprise a peptide, polypeptide, protein, siRNA, shRNA, microRNA (miRNA) can act concurrently and synergistically to directly affect viral infection and/or replication and/or act concurrently and synergistically to regulate downstream inflammation and vascular cell related pathologies in response to microbial infection). Accordingly, disclosed herein are methods of treating, decreasing, inhibiting, reducing, ameliorating and/or preventing a microbial infection (such as, for example, a viral, bacterial, fungal, or parasitic infection) or symptoms thereof (including, but not limited to microbial induced cytokine storm, microbial initiated bradykinin storm, and/or acute respiratory distress syndrome) in a subject comprising administering to a subject any of the compositions disclosed herein. For example, disclosed herein are methods of treating, decreasing, inhibiting, reducing, ameliorating and/or preventing a microbial infection (such as, for example, a viral, bacterial, fungal, or parasitic infection) or symptoms thereof (including, but not limited to microbial induced cytokine storm, microbial initiated bradykinin storm, and/or acute respiratory distress syndrome) in a subject comprising administering to a subject a composition comprising a therapeutically effective amount of a MSC secretome (such as, for example, including, but not limited to MSC growth factor, MSC exosome, MSC extracts and/or extracellular vesicle comprising compositions) and one or more biomolecules (such as, for example, a peptide, polypeptide, protein, siRNA, shRNA, and/or microRNA (miRNA)) that selectively bind to one or more microbial immunogens, or inhibit the ability of a microbe to inhabit a host, or inhibit, decrease, reduce, ameliorate, and/or prevent one or more secondary conditions caused by a microbial infection (such as, for example, comprise a peptide, polypeptide, protein, siRNA, shRNA, microRNA (miRNA).

As noted above, the composition for use in the disclosed methods can comprises bone marrow-derived mesenchymal lineage cells that adhere to culture plastic and may differentiate in culture into multiple mature cell fates including but not limited to adipocyte, osteoblast and chondrocyte fates and/or secreted extracellular vesicles that contain a core protein composition that includes any combination of core composition proteins, selected from the group consisting of Ferritin, NUP85, LAMP2, GPR115, Serpin F1, OPN, PAI-1, DAPP1, Cathepsin B, Semaphorin 6C, PDGF R alpha, Sortilin, Serpin B6, Dkk-3, Thrombomodulin, PF4, MIF, Periostin, Furin, TIMP-1, Decorin, PCKT, CD99, CD63, CD9, CD81, Transferrin, DcR3, Lumican, TIMP-2, SLITRK5, FAP, Artemin, DPPII, cIAP-1, Pentraxin 3, Visfatin, Neprilysin, Albumin, Galectin-1, UNC5H3, IL-20 R beta, SREC-II, JAM-C, TNF RI, htPAPP-A, eNOS, MSP R, TPP1, LAMP1, B2M, NCAM-1, HIF-1 alpha, ST6GAL1, CD99-L2, Plexin A4, EMMPRIN, p53, Semaphorin 7A, NKp80, Cystatin B, Osteoadherin, Midkine, Calreticulin, Osteoactivin, Legumain, TAZ, Cathepsin L, RBP4, Serpin A4, JAM-A, MCSF, LIMPII, OPG, IL-22, Galectin-3, MOG, Trypsin 3, SIRP alpha, and Syndecan-4, and at least one protein selected from the group consisting of: Ferritin, IGFBP-4 IL-1 R6 GSTM1, NUP85, LAMP2, MeprinA, IL-1 F10, bIG-H3, GPR115, TGFbT, Ephrin-A4, CD109, Serpin F1, IGFBP-6, HS3ST4, Aminopeptidase LRAP, OPN, PAI-1, DAPP1, GDF-9, Cathepsin B, IGFBP-2, Semaphorin 6C, IGF-2, PDGF R alpha, Sortilin, Serpin B6, Dkk-3, CNTF, TSP-1, GM-CSF Ra, Thrombomodulin, Endoglycan, IGFBP-3, RGM-C, PF4, MIF, TGM4, Periostin, Furin, TIMP-1, PAPP-A, Decorin, PCK1, Arylsulfatase A, CD99, CA2, PRDX4, Transferrin, DcR3, GP73, LAIR2, ULBP-4, Lumican, TIMP-2, TFPI, SOX2, SLITRK5, FAP, Spinesin, ENPP-2, CD97, CTACK, Integrin alpha 1, EXTL3, IL-18 BPa, PD-L2, PSMA, IL-20 Ra, Glyoxalase II, Trypsin 1, IGF-2R, ADAMTSL-1, Erythropoietin, Plexin D1, DNMT3A, BCL-2, CL-P1, Ephrin-B3, FABP6, CHI3L1, FCRL5, TFF3, Artemin, DPPII, cIAP-1, PDGF Rb, Pentraxin 3, Angiotensinogen, Follistatin, CF VII, Persephin, TRAIL R1, THAP11, CD200, CLEC-2, AMIGO, IGFBP-5, PON1, SOX7, GALNT10, Visfatin, Progranulin, PCSK2, GKN1, IL-18, Neprilysin, Stabilin-2, IL-17 RD, Albumin, Follistatin-like 1, MMP-10, FKBP51, LRRC4, Pref-1, Galectin-1, Troponin C, UNC5H3, FLRT2, CD314, Semaphorin 6B, Netrin-4, CD27 Ligand, IL-20 R beta, Semaphorin 6A, TSK, Cytokeratin-8, CHST3, Mcl-1, DPPIV, SREC-II, Norrin, JAM-C, Bel-10, Wnt-4, LSECtin, Kell, TNF RI, PTP1B, htPAPP-A, IDO, PDGF-CC, Galanin, Activin A, TLR2, SCCA2, FABP1, eNOS, SHP-1, ICOS, ClqTNF9, MMP-1, TC-PTP, IL-24, gp130, C-myc, LILRB4, BMP-2, MIA, CD34, CD63, CD9, CD81, IFNab R2, Glypican 2, MSP R, DSCAM, Matriptase, KIR2DL3, CD30, Siglec-10, CLEC-1, TPP1, Ubiquitin+1, ANGPTL4, TWEAK R, Nidogen-1, CD2, Kallikrein 1, TSLP R, LAMP1, TROY, VCAM-1, Siglec-11, S100A1, PARI, Thyroid Peroxidase, Aminopeptidase P2, IL-1 RI, ADAM9, OSM R beta, Thrombospondin-2, SMPD1, B2M, MFRP, LRP-6, ST3GAL1, NCAM-1 (CD56), Granzyme B, Adiponectin, IL-22BP, TPST2, PD-ECGF, LH, LEDGF, Cyr61, ULBP-3, IFNb, THSD1, FGF-23, LAMA4, Adipsin, AIF, SorCS2, SULT2A1, CD39L2, Insulin R, HIF-1 alpha, OX40 Ligand, Pax3, UCH-L3, cMASP3, Langerin, Desmin, SOX9, ST6GAL1, MEP1B, CD99-L2, Plexin A4, Semaphorin 4D, ROBO2, PDX-1, APRIL, Neurturin, Kremen-2, EMMPRIN, Activin RIB, Neuroligin 2, Epiregulin, CA5A, MMP-12, GALNT2, CEACAM-5, VEGF R1, DSPG3, SorCS1, Matrilin-2, sFRP-3, p53, EphB3, NCKI, Semaphorin 7A, NKp80, Prolactin, Cystatin B, Sirtuin 1, FGF-16, FGF R5, NQO-1, Semaphorin 6D, FGF-3, GATA-4, VAP-A, CHST2, Pappalysin-2, Syndecan-3, Jagged 1, AKR1C4, Olfactomedin-2, Osteoadherin, NKp44, Thyroglobulin, IL-21R, Chemerin, EphA1, CD48, MICB, FGF-5, TRANCE, CES2, ULBP-1, Integrin alpha 5, VAMP-2, FLRG, Ret Midkine, CD73, TRACP, proGRP, Granzyme H, PRX2, p27, Siglec-6, Dectin-1, CD51, Notch-1, Calreticulin, DR3, DCTN1, CDC25B, Osteoactivin, ACE, CA125, HAO-1, PSMA1, FCRLB, BMP-9, CRIM1, LIF, SPINK1, EphB6, RGM-B, HS3ST1, ROR1, CMG-2, 4-1BB Ligand, L1CAM-2, p63, Cathepsin V, Testican 2, Glypican 5, CD6, Siglec-2, Legumain, PRELP, CES1, TAZ, NSE, TECK, HTRA2, HIF-1 beta, TAFA1, Podocalyxin, RalA, CRELD2, GRAP2, SP-D, BID, GFR alpha-2, Notch-3, VEGF R3, DLL4, TGFb2, LIGHT, XIAP, ST8SIA1, Cathepsin L, 6Ckine, MIS RII, Kallikrein 5, TGM3, FCAR, Contactin-2, CD83, IL-1 R3, SALM4, GBA3, ROBO4, OSCAR, VEGF, IGSF3, Biglycan, Neudesin, ILT4, uPAR, Axl, WIF-1, IL-7 R alpha, GPR56, CEACAM-3, MCEMPI, FABP2, Plexin B3, MEPE, Activin RIIA, ANG-2, Cochlin, Presenilin 1, NPTXR, SLAM, COMT, SPHKI, RBP4, Nectin-1, GUSB, Nidogen-2, IL-17F, SR-AI, TAFA2, N-Cadherin, IL-17B, IL-17 RC, MIP-3b, Cystatin C, Cystatin D, AMSH, FcERI, CLECIOA, HGF R, ANG-1, Prolactin R, FGF-20, CD28, Nogo-A, HSD17B1, IL-19, Enteropeptidase, Cathepsin E, TSLP, TCN2, GDF-15, Epimorphin, GRK5, PD-1, Serpin A4, ADAM23, NOV, Galectin-2, Neurexin 3 beta, TLR3, Sirtuin 2, Numb, IL-28 R alpha, IL-33, Lin28, FCRL1, KLF4, NKp30, Lymphotactin, Cystatin SN, JAM-A, Calreticulin-2, ErbB4, BMP-8, IL-27 Ra, Fas, IL-4 Ra, Kallikrein 14, Matrilin-3, Olig2, Kallikrein 12, CA13, IL-9, Nectin-3, MPIF-1, Cystatin S, ADA, IL-2 Rb, GFR alpha-1, Smad4, ICAM-1, MEF2C, TREM-1, L-Selectin, Hepsin, CD42b, MCSF, RANK, CHST4, CA8, FCRL3, ASAH2, CF XIV, PYY, HGF, I-TAC, Semaphorin 4C, SorCS3, Tie-1, IL-31 RA, Arginase 1, POGLUT1, IL-1ra, Podoplanin, TIM-3, CREG, CD300f, uPA, EphA2, LRRTM4, LIMPII, Tenascin R, CPE, PECAM-1, DNAM-1, DKK-1, OPG, CPB1, TSH, MMP-2, Siglec-9, ICAM-3, Cystatin SA, Galectin-4, Pepsinogen II, Desmoglein-3, Nectin-4, SCF, Serpin A5, PTH, FGF-19, MSP, IL-28A, FGF-12, METAP2, ASAHL, EDIL3, NTAL, EGF R, TAFA5, Galectin-9, vWF-A2, TACE, Activin RIIB, Cathepsin S, LDL R, BMPR-IA, OX40, IL-13 R2, B7-H4, MMP-13, ANGPTL7, TRAIL R4, IGSF4B, Sirtuin 5, PEAR1, SH2D1A, Cerberus 1, GDF-11, Nrf2, TROP-2, NUDT5, ROR2, EphB4, Glypican 1, LAP (TGFb1), Gas6, Contactin-1, IL-27, UNC5H4, ICAM-2, MBL, HS3ST3B1, RCOR1, IL-10 Rb, XEDAR, IL-22, PILR-alpha, NRGi-b1, FABP4, RGM-A, RELT, TrkC, C5a, SREC-I, Nestin, TPO, ErbB3, Kirrel3, FLRT1, Galectin-3, CXCL16, JAM-B, DR6, Nogo Receptor, TLR4, VEGF R2, Tie-2, IL-15 R, Caspr2, LTbR, LAMP, ALCAM, GLP-1, NG2, IL-22 R alpha 1, AMIGO2, HCC-1, TFPI-2, ULBP-2, Desmoglein 2, Aggrecan, Syntaxin 4, VAMP-1, Nectin-2, FGF-21, Flt-3, GFAP, TIM-1, Inhibin A, Cadherin-4, PlGF-2, Neurogranin, HE4, IL-23 R, Galectin-7, GALNT3, GITR L, CD14, R-Spondin 2, CK19, Cardiotrophin-1, TREML1, HAPLN1, CD27, ANG-4, Siglec-7, CD155, VEGF-C, TNF RII, PGRP-S, SDF-1a, PDGF-AB, GPVI, CD40, SCF R, Thrombospondin-5, IL-1 RII, Neuropilin-2, Cadherin-13, E-Selectin, GITR, WISP-1, Renin, AgRP, MDL-1, ROBO3, RANTES, Endocan, Granulysin, hCGb, Mesothelin, TLR1, TRAIL, MOG, DDR1, NGF R, TRAIL R3, Trypsin 3, ARSB, LIF R alpha, BAFF R, CD157, Granzyme A, 2B4, ESAM, IL-1 R4, CXCL14, IL-31, SIRP alpha, Uromodulin, CTRC, CEACAM-1, TARC, MIP-3a, SDF-1b, NKp46, MCP-3, IL-32 alpha, TGFb3 FOLR2, CD58, IL-23, CD36, TNFb, Shh-N, Ficolin-1, Reg4, ILT2, Mer, TREM-2, Flt-3L, CD5, IL-6, CD229, Insulin, Syntaxin 6, GRO, Bcl-w, Lipocalin-2, PDGF-AA, IL-2 Ra, Angiogenin, LYVE-1, CD4, RAGE, CDNF, Brevican, NAP-2, PU.1, EDAR, ADAMTS13, Kynureninase, PTH1R, IFN-gamma R1, CrkL, B7-1, PARC, Draxin, VE-Cadherin, Procalcitonin, SOX15, Kallikrein 11, BCMA, Dectin-2, EpCAM, HCC-4, TGFa, IP-10, BLAME, CILP-1, PIGF, LOX-1, MCP-2, Resistin, HVEM, ENPP-7, Syndecan-4, IL-2 Rg, MICA, Dopa Decarboxylase, NPDC-1, MCP-4, EG-VEGF, Glycoprotein V, Semaphorin 4G, IL-12p40, PSA-total, IL-15, MAP1D, C1q, TNF4, Dtk, Endoglin, ENA-78, Reg3A, MIP-1b, FGF-17, IL-6R, IL-8, Galectin-8, CA4, Cystatin E M, FUT8, B7-H3, GCP-2, CD40L, MDC, 4-1BB, HO-1, SOST, S100A13, Kallikrein 7, and IL-13.

In some embodiments, the composition for use in the disclosed methods comprises one or more biomolecules that can selectively bind to a microbial antigen (such as a viral, bacterial, fungal, or parasitic antigen), block its function and/or enzymatically process the protein so it is detectable by the host immune system to then activate virus immune response to disable the virus' ability to infect cells. For example, the biomolecule can bind to a viral antigen from a virus selected from the group consisting of Herpes Simplex virus-1 (such as, for example, glycoprotein D and/or glycoprotein G), Herpes Simplex virus-2 (such as, for example, glycoprotein D and/or glycoprotein G), Varicella-Zoster virus (such as, for example, glycoprotein E), Epstein-Barr virus (such as, for example the EBV glycoprotein), Cytomegalovirus (such as, for example the CMV glycoprotein), Human Herpes virus-6, Variola virus, Vesicular stomatitis virus, Hepatitis A virus, Hepatitis B virus (including, but not limited to the hepatitis B virus surface antigen), Hepatitis C virus (such as, for example, the Hepatitis C E1, E2, or E3 proteins), Hepatitis D virus, Hepatitis E virus, Rhinovirus, Coronavirus (including, but not limited to spike or envelope proteins from avian coronavirus (IBV), porcine coronavirus HKU15 (PorCoV HKU15), Porcine epidemic diarrhea virus (PEDV), HCoV-229E, HCoV-OC43, HCoV-HKU1, HCoV-NL63, SARS-CoV, SARS-CoV-2 (including, but not limited to the B1.351 variant, B.1.1.7 variant, and P.1 variant), or MERS-CoV), Influenza virus A (such as, for example the hemagglutinin (HA) protein including the HA1 and HA2 protein and including trimeric HA), Influenza virus B (such as, for example the hemagglutinin (HA) protein including the HA1 and HA2 protein and including trimeric HA), Measles virus (such as, for example the hemagglutinin protein), Polyomavirus, Human Papilomavirus, Respiratory syncytial virus (such as, for example the RSV G protein), Adenovirus, Coxsackie virus, Dengue virus (such as, for example capsid protein, envelope protein, and/or premembrane/membrane protein), Mumps virus, Poliovirus, Rabies virus (including, but not limited to the Rabies glycoprotein), Rous sarcoma virus, Reovirus, Yellow fever virus, Zika virus (such as, for example capsid protein, envelope protein, and/or premembrane/membrane protein), Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A (including, but not limited to viral protein 4 and viral protein 7), Rotavirus B (including, but not limited to viral protein 4 and viral protein 7), Rotavirus C (including, but not limited to viral protein 4 and viral protein 7), Sindbis virus, Simian Immunodeficiency virus, Human T-cell Leukemia virus type-1, Hantavirus, Rubella virus, Simian Immunodeficiency virus, Human Immunodeficiency virus type-1 (such as, for example, glycoprotein (gp), envelope protein (Env), or gag protein), and Human Immunodeficiency virus type-2. For example, the presence of furin protein in the invention may enable enzymatic processing of shed viral particle spike protein to the upright immune-detectable conformation, improving immune response to degrade extracellular viral particles. Additionally, for example, the composition can comprise a ferritin protein content effective to increase IL-10 secretion by immune regulatory cells to inhibit hyperactive immune cell actions, collectively referred to as a cytokine storm or the protein PAI-1 that can block production of plasmin to inhibit the "bradykinin storm." The biomolecule of the composition can also comprise thrombomodulin, which can suppress micro-blood clotting frequency, reducing pathogenic clotting, and reduce thrombotic emboli; and other protein components that inhibit NETosis (neutrophil induced nucleic acid-protein networks intended to capture pathogenic invading species, for example, viruses, and bacteria within the vasculature)

In some embodiments, the biomolecule of the composition for use in the disclosed methods comprises a micro RNA content that may bind to RNA sequences of a microbe and block translation from or activate degradation of the microbial RNA sequence. The composition thereby may reduce microbial replication rate (including, but not limited to viral replication rate) and reduce host cell death. For example, disclosed herein are compositions comprising a therapeutically effective amount of an MSC secretome (such as, for example, including, but not limited to MSC growth factor, MSC exosome, MSC extracts and/or extracellular vesicle comprising compositions) and one or more biomolecules comprise a miRNA is selected from the group of miRNA comprising hsa-let-7a-5p, hsa-let-7b-5p, hsa-let-7c-5p, hsa-let-7d-3p, hsa-let-7e-5p, hsa-let-7g-5p, hsa-let-7i, hsa-let-7i-5p, hsa-miR-100-5p, hsa-miR-103a-3p, hsa-miR-106a-5p, hsa-miR-106b-5p, hsa-mir-10b, hsa-miR-10b-5p, hsa-mir-1246, hsa-miR-1246, hsa-miR-125a-5p, hsa-miR-125b-5p, hsa-miR-130a-3p, hsa-mir-130b, hsa-miR-130b-3p, hsa-miR-132-3p, hsa-miR-136-5p, hsa-miR-138-5p, hsa-miR-139-5p, hsa-mir-140, hsa-miR-140-3p, hsa-miR-145-5p, hsa-mir-146a, hsa-miR-146a-5p, hsa-miR-148a-3p, hsa-miR-152-3p, hsa-miR-15a-5p, hsa-miR-15b-5p, hsa-mir-16-1, hsa-mir-16-2, hsa-miR-16-5p, hsa-miR-17-5p, hsa-miR-181a-5p, hsa-miR-191-5p, hsa-miR-193a-5p, hsa-miR-193b-3p, hsa-miR-197-3p, hsa-miR-199a-3p, hsa-miR-199a-5p, hsa-miR-199b-5p, hsa-miR-19a-3p, hsa-miR-19b-3p, hsa-miR-20a-5p, hsa-mir-203a, hsa-miR-203a-3p, hsa-miR-214-3p, hsa-mir-21, hsa-miR-21-3p, hsa-miR-21-5p, hsa-mir-221, hsa-miR-221-3p, hsa-mir-222, hsa-miR-222-3p, hsa-miR-22-3p, hsa-miR-23a-3p, hsa-miR-23b-3p, hsa-mir-24-1, hsa-mir-24-2, hsa-miR-24-3p, hsa-mir-25, hsa-miR-25-3p, hsa-miR-26a-5p, hsa-miR-27a-3p, hsa-mir-27b, hsa-miR-27b-3p, hsa-miR-29a-3p, hsa-miR-29c-3p, hsa-miR-30a-5p, hsa-miR-30a-5p, hsa-miR-30b-5p, hsa-miR-30c-5p, hsa-mir-30d, hsa-miR-30d-5p, hsa-mir-30e, hsa-miR-30e-5p, hsa-miR-31-3p, hsa-miR-31-5p, hsa-miR-320a, hsa-miR-342-3p, hsa-miR-345-5p, hsa-miR-34a-5p, hsa-miR-361-5p, hsa-miR-376a-3p, hsa-miR-376c-3p, hsa-miR-423-3p, hsa-miR-423-5p, hsa-miR-424-5p, hsa-miR-484, hsa-mir-486-1, hsa-mir-486-2, hsa-miR-486-5p, hsa-miR-570-3p, hsa-miR-574-3p, hsa-miR-663a, hsa-miR-874-3p, hsa-mir-92a-1, hsa-mir-92a-2, hsa-miR-92a-3p, hsa-miR-92b-3p, hsa-mir-93, hsa-miR-93-5p, hsa-miR-940, hsa-miR-99a-5p, and hsa-miR-99b-5p. For example, a composition comprising miRNA (such as hsa-miR-19a-3p, hsa-miR-19b-3p) that can be effective to inhibit translation of Bradykinin receptor 2, which is critical for activation of bradykinin signaling responsible for severe vascular response to coronavirus infection. Similarly, wherein the composition comprises microRNA that can inhibit translation of Kallikrein B1 (such as hsa-miR-24-3p) and other Kallikrein proteins involved in proteolytic digestion of the bradykinin precursor protein to generate bradykinin peptide. Also, for example, wherein the biomolecule of the composition comprises microRNA content that can inhibit translation of cellular proteins involved in enabling virus fusion to the cell membrane using the angiotensin-converting enzyme 2 (ACE 2) receptor protein or by blocking activity of proteins activated through the process of the virus binding to the ACE 2 receptor protein. For example, the transmembrane protease, serine 2 (TMPRSS2) enzyme can be inhibited. TMPRSS2 is required to enable SARS-CoV-2 spike protein to interact with the ACE 2 Receptor and initiate membrane fusion. Exemplary microRNA content may include human miRNA sequences hsa-let-7a-5p, hsa-let-7b-5p, hsa-let-7c-5p, hsa-let-7g-5p, hsa-let-7i-5p, hsa-miR-214-3p, and hsa-miR-27a-3p, which all have binding sites in mRNA for TMPRSS2. Additionally, wherein the biomolecule of the composition comprises microRNA that can inhibit proteins of the bradykinin pathway. For example, the microRNA sequences hsa-let-7a-5p, hsa-let-7b-5p, hsa-let-7c-5p, hsa-let-7g-5p, hsa-let-7i-5p, hsa-let-7i, hsa-miR-106a-5p, hsa-miR-106b-5p, hsa-miR-15a-5p, hsa-miR-15b-5p, hsa-miR-16-5p, hsa-miR-17-5p, hsa-miR-20a-5p, hsa-miR-23a-3p, hsa-miR-23b-3p, hsa-mir-24-1, hsa-mir-24-2, hsa-miR-25-3p, hsa-miR-92a-3p, hsa-miR-92b-3p, and hsa-miR-93-5p may bind and prevent translation of hyaluronan synthase 2, thereby preventing formation of Hyaluronic acid complexes in the lungs. Hyaluronic acid complexes block oxygen exchange in the alveoli. In some embodiments of the methods disclosed herein, the biomolecule of the composition comprises a microRNA content, a protein content, or a combination thereof that can inhibit a cytokine storm. The composition may inhibit the cytokine storm by (i) inhibiting translation of cytokine proteins by binding mRNA sequences for those proteins, (ii) sterically hindering ligand/receptor interactions, (iii) enzymatically altering ligands or receptors to inhibit their pro-inflammatory actions, or (iv) activating inhibitory proteins, lipids or RNA sequences that inhibit the proinflammatory cytokines such as, but not limited to, IL-1beta, IL-6, TNF-alpha, GM-CSF, M-CSF. For example, human miRNA sequences hsa-let-7a-5p, hsa-let-7b-5p, hsa-let-7c-5p, hsa-let-7g-5p, hsa-let-7i-5p, and hsa-miR-547-3p are able to bind IL-6 mRNA, while hsa-miR-130a-3p and hsa-miR-181a-5p can inhibit translation of TNF-alpha.

It is understood and herein contemplated that the MSC secretome used in the compositions of the disclosed methods can comprises exosomes and growth factors. The growth factors and exosomes can be allogenic or autogenic. The growth factors and exosomes can be derived from any cell in the human body, such as from ectodermal cells, endodermal cells, or mesodermal cells. For example, the MSC secretomes may comprise mesenchymal stem cell (MSC) derived growth factors, MSC derived exosomes, or both MSC derived growth factors and exosomes. In some embodiments, the method further comprises adding at least one additive with the exosomes and growth factors. Specifically, MSCs under appropriate wound healing conditions may produce suitable therapeutic agents, such as exosomes and growth factors, that can provide therapy for inflammatory lung diseases. In one aspect, disclosed herein are compositions of any preceding aspect, wherein the MSC secretome composition further comprises prostaglandin E2 (PGE2), transforming growth factor β1 (TGF-β1), hepatocyte growth factor (HGF), stromal cell derived factor-1 (SDF-1), nitric oxide, indoleamine 2,3-dioxygenase, interleukin-4 (IL-4), IL-6, interleukin-10 (IL-10), IL-1 receptor antagonist and soluble TNF-α receptor, insulin-like growth factors, fibroblast growth factors (FGF) 1-23 (especially, FGF1 and FGF2), bone morphogenetic proteins (BMPs) 1-15, epidermal growth factor (EGF), transforming growth factor-α (TGF-α) macrophage-stimulating protein (MSP), platelet derived growth factor (PLGF), vascular endothelial growth factor (VEGF), macrophage colony stimulating factor (M-CSF), insulin, granulocyte colony stimulating factor (G-CSF), granulocyte macrophage colony stimulating factor (GM-CSF estrogen, and/or thyroid hormones.

As noted above, the microbial infection can comprise a viral, bacterial, fungal, or parasitic infection. In one aspect, disclosed herein are methods of treating, decreasing, inhibiting, reducing, ameliorating and/or preventing a microbial infection or symptoms thereof of any preceding aspect, wherein the microbial infection comprises an infection from a virus selected from the group of viruses consisting of Herpes Simplex virus-1, Herpes Simplex virus-2, Varicella-Zoster virus, Epstein-Barr virus, Cytomegalovirus, Human Herpes virus-6, Variola virus, Vesicular stomatitis virus, Hepatitis A virus, Hepatitis B virus, Hepatitis C virus, Hepatitis D virus, Hepatitis E virus, Rhinovirus, Coronavirus (including, but not limited to avian coronavirus (IBV), porcine coronavirus HKU15 (PorCoV HKU15), Porcine epidemic diarrhea virus (PEDV), HCoV-229E, HCoV-OC43, HCoV-HKU1, HCoV-NL63, SARS-CoV, SARS-CoV-2, or MERS-CoV), Influenza virus A, Influenza virus B, Measles virus, Polyomavirus, Human Papillomavirus, Respiratory syncytial virus, Adenovirus, Coxsackie virus, Chikungunya virus, Dengue virus, Mumps virus, Poliovirus, Rabies virus, Rous sarcoma virus, Reovirus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Simian Immunodeficiency virus, Human T-cell Leukemia virus type-1, Hantavirus, Rubella virus, Simian Immunodeficiency virus, Human Immunodeficiency virus type-1, and Human Immunodeficiency virus type-2.

Also disclosed herein are methods of treating, decreasing, inhibiting, reducing, ameliorating and/or preventing a microbial infection or symptoms thereof of any preceding aspect, wherein the microbial infection comprises an infection from a bacteria selected from the group of bacteria consisting of Mycobacterium tuberculosis, Mycobacterium bovis, Mycobacterium bovis strain BCG, BCG substrains, Mycobacterium avium, Mycobacterium intracellular, Mycobacterium africanum, Mycobacterium kansasii, Mycobacterium marinum, Mycobacterium ulcerans, Mycobacterium avium subspecies paratuberculosis, Mycobacterium chimaera, Nocardia asteroides, other Nocardia species, Legionella pneumophila, other Legionella species, Acetinobacter baumanii, Salmonella typhi, Salmonella enterica, other Salmonella species, Shigella boydii, Shigella dysenteriae, Shigella sonnei, Shigella flexneri, other Shigella species, Yersinia pestis, Pasteurella haemolytica, Pasteurella multocida, other Pasteurella species, Actinobacillus pleuropneumoniae, Listeria monocytogenes, Listeria ivanovii, Brucella abortus, other Brucella species, Cowdria ruminantium, Borrelia burgdorferi, Bordetella avium, Bordetella pertussis, Bordetella bronchiseptica, Bordetella trematum, Bordetella hinzii, Bordetella pteri, Bordetella parapertussis, Bordetella ansorpii other Bordetella species, Burkholderia mallei, Burkholderia psuedomallei, Burkholderia cepacian, Chlamydia pneumoniae, Chlamydia trachomatis, Chlamydia psittaci, Coxiella bumetii, Rickettsial species, Ehrlichia species, Staphylococcus aureus, Staphylococcus epidermidis, Streptococcus pneumoniae, Streptococcus pyogenes, Streptococcus agalactiae, Escherichia coli, Vibrio cholerae, Campylobacter species, Neiserria meningitidis, Neiserria gonorrhea, Pseudomonas aeruginosa, other Pseudomonas species, Haemophilus influenzae, Haemophilus ducreyi, other Hemophilus species, Clostridium tetani, other Clostridium species, Yersinia enterolitica, and other Yersinia species, and Mycoplasma species. In one aspect the bacteria is not Bacillus anthracis.

In one aspect, also disclosed herein are methods of treating, decreasing, inhibiting, reducing, ameliorating and/or preventing a microbial infection or symptoms thereof of any preceding aspect, wherein the microbial infection comprises an infection from a fungus selected from the group of fungi consisting of Candida albicans, Cryptococcus neoformans, Histoplasma capsulatum, Aspergillus fumigatus, Coccidiodes immitis, Paracoccidioides brasiliensis, Blastomyces dermitidis, Pneumocystis carinii, Penicillium marneffi, and Alternaria altemata.

Also disclosed herein are methods of treating, decreasing, inhibiting, reducing, ameliorating and/or preventing a microbial infection or symptoms thereof of any preceding aspect, wherein the microbial infection comprises a parasitic infection with a parasite selected from the group of parasitic organisms consisting of Toxoplasma gondii, Plasmodium falciparum, Plasmodium vivax, Plasmodium malariae, other Plasmodium species, Entamoeba histolytica, Naegleria fowleri, Rhinosporidium seeberi, Giardia lamblia, Enterobius vermicularis, Enterobius gregorii, Ascaris lumbricoides, Ancylostoma duodenale, Necator americanus, Cryptosporidium spp., Trypanosoma brucei, Trypanosoma cruzi, Leishmania major, other Leishmania species, Diphyllobothrium latum, Hymenolepis nana, Hymenolepis diminuta, Echinococcus granulosus, Echinococcus multilocularis, Echinococcus vogeli, Echinococcus oligarthrus, Diphyllobothrium latum, Clonorchis sinensis; Clonorchis viverrini,

*Fasciola hepatica, Fasciola gigantica, Dicrocoelium den-driticum, Fasciolopsis buski, Metagonimus yokogawai, Opisthorchis viverrini, Opisthorchis felineus, Clonorchis sinensis, Trichomonas vaginalis, Acanthamoeba species, Schistosoma intercalatum, Schistosoma haematobium, Schistosoma japonicum, Schistosoma mansoni,* other *Schistosoma* species, *Trichobilharzia regenti, Trichinella spiralis, Trichinella britovi, Trichinella nelsoni, Trichinella nativa,* and *Entamoeba histolytica.*

E. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Experimental treatments have shown that the treatment method of the present disclosure has greatly improved the health in critical cases of COVID-19, resulting in all test patients avoiding use of ventilators or being removed from a ventilator within 72 hours.

FIGS. 1A-1C show representative images captured by transmission electron microscopy (TEM) showing size distribution of the EVs present within an invention sample from a cyclic Guanosine Monophosphate (cGMP) manufactured lot #PV-441-2002C. FIGS. 1A, 1B, and 1C have scale bars of 200 nm, 100 nm, and 100 nm, respectively. Images 1, 2, and 3 are detail views of structures shown in FIG. 1C. Single Particle Interferometric Reflectance Imaging Sensor (SP-IRIS) is an imaging system used to capture image data of nanoparticles and transforms information into particle size, concentration, and identity. One such commercial system is the NANOVIEW ExoView™ system.

FIGS. 2A-2D shows CD81, CD63, and CD9 indicating captured exosomes. FIG. 2A is a chart that illustrates results of Lyophilized Test Lot 4411901C. FIG. 2B is a chart that illustrates results of pre-excipient Test Lot 441901D. FIG. 2C is a chart that illustrates results of pre-excipient Test Lot 441902A. FIG. 2D is a chart that illustrates results of pre-excipient Test Lot 441902B. All samples were stained with fluorescently labeled monoclonal antibodies. CD63 antibody (Ab) is indicated by red, CD81 Ab is indicated by green, and CD9 Ab is indicated by blue. FIG. 2 includes results for the following proteins. CD9 refers to a protein expressed in exosomes and plasma membrane EVs, a member of the tetraspanin protein family, associated with integrins. CD9 regulates sperm-egg interactions, platelet aggregation and activation, and cell adhesion. In myocytes, CD9 associates with CD81 and inhibits myotube formation during muscle regeneration. In monocytes/macrophages, CD9 associates with CD81 and integrins and prevents giant cell and osteoclast formation. CD63 refers to a protein expressed in exosomes, a member of the tetraspanin protein family. CD63 functions as the surface receptor for TIMP-1, activates cellular signaling cascades, promotes cell survival, and activates AKT and FAK/PTK2 pathways. CD81 refers to a protein expressed in exosomes, a member of the tetraspanin protein family. In myocytes, CD81 associates with CD9 and inhibits myotube formation during muscle regeneration. In monocytes/macrophages, CD81 associates with CD9 and integrins and prevents giant cell and osteoclast formation. CD81 is expressed in B-cells and is involved in CD19 receptor trafficking.

FIGS. 3A-3D are a set of microphotographs of CD63 Captured Exosomes. FIG. 3A illustrates lyophilized Test Lot 4411901C. FIG. 3B illustrates pre-excipient Test Lot 441901D. FIG. 3C illustrates pre-excipient Test Lot 441902A. FIG. 3D illustrates pre-excipient Test Lot 441902B. The image resolution limit for all images is 20 nm. All samples are stained with CD63 antibody (in red), CD81 Ab (in green), and CD9 Ab (in blue). Nanoparticle Tracking Analysis (NTA) is a method that allows visualizing and analyzing particles in suspension.

FIG. 4 reproduces a list of MSC secretome (also referred to under the trade name EXOFLO™) microRNA content identified as Table 1 in Park et al. Table 1 was highlighted to identify sequences found in EXOFLO™ that may directly bind to the SARS-CoV-2 virus RNA sequence. The Table 1 footnotes include the following notes. 1. Predictions of 3' UTR binding were conducted with the PITA tool. 2. To predict miRNA binding to the 3' UTR and region, analysis of the whole genome was also performed using miRDB. 3. Expression (%) indicates the level of each miRNA relative to the total miRNA levels, calculated miRNA CPM/total CPM*100. 4. Seed location where each miRNA is expected to bind the SARS-CoV-2 genome. 5. Seed match length. 6. Seed mismatch length. 7. Wobble number caused by G and U base pairing. 8. Thermodynamic energy required for binding. Lower energy indicates stronger binding prediction. The higher the score, the greater the likelihood of strong binding. 9. The prediction score from the miRDB method. According to miRDB, a predicted target with score >80 is most likely to be tightly bound. 10. Start site of the miRNA seed location matching to the RNA genome of SARS-CoV-2. 11. Rank of expression level within extracellular vesicles (EVs).

Figure 5:
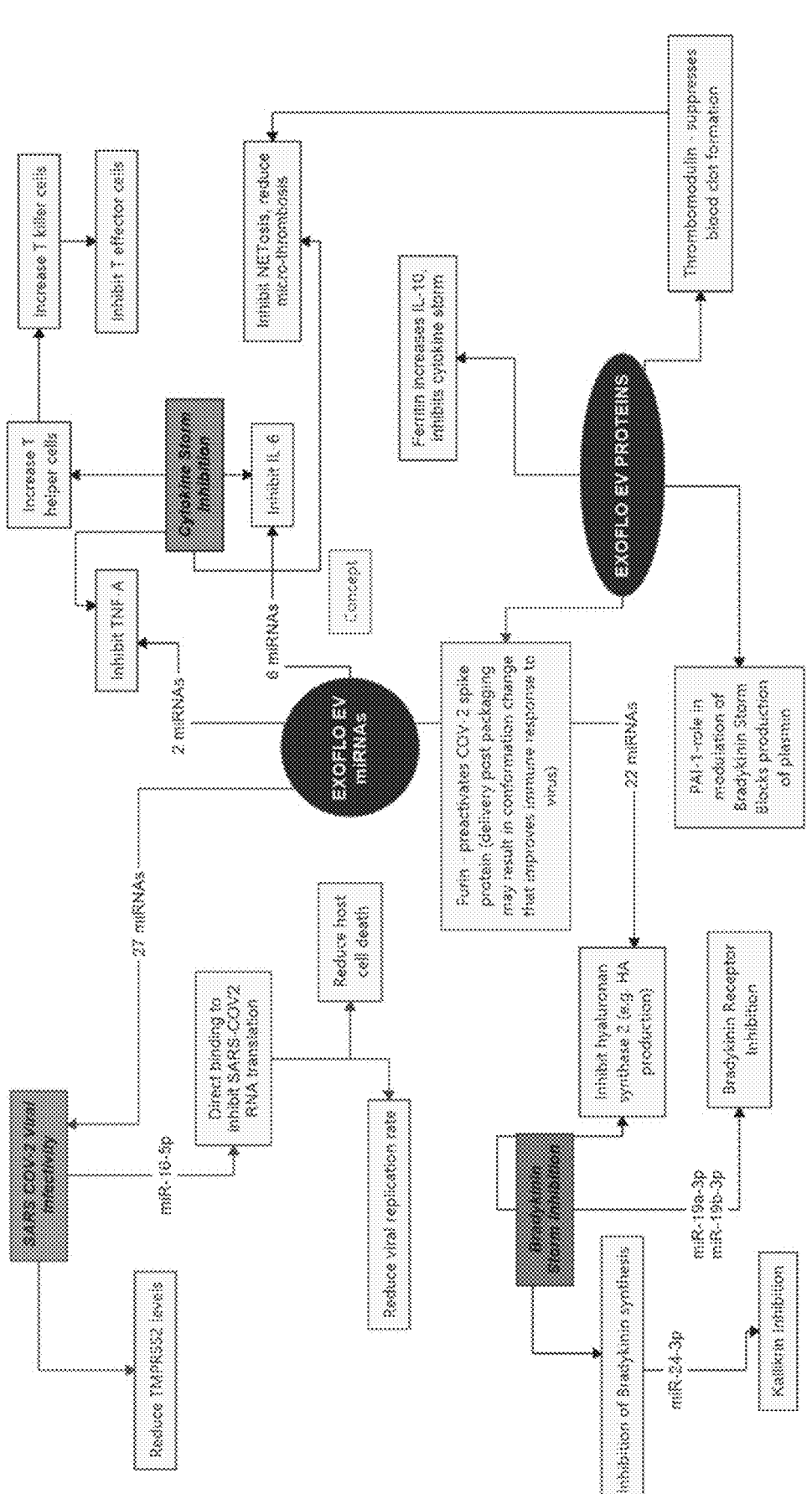

FIG. 5 is a schematic representation of multiple mechanisms of action discussed herein by which the invention may ameliorate coronavirus infection and subsequent symptoms.

Figure 6:
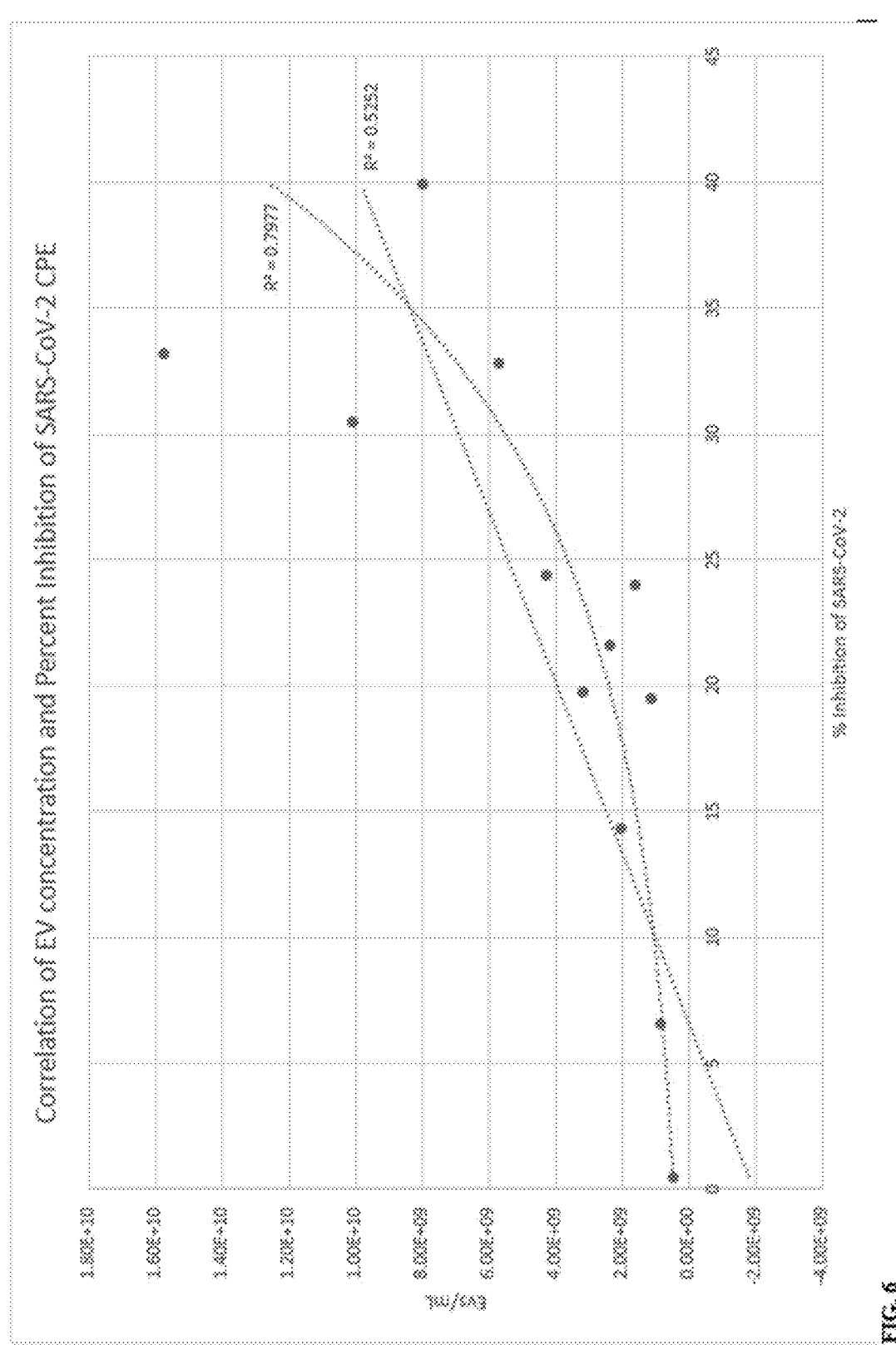

FIG. 6 is a graphic representation of viral toxicity inhibition (infectivity and replication) as a function of extracellular vesicle concentration, indicating a dose response relationship of the inventive composition on an in vitro live SARS CoV-2 virus in a "cyto-protective" assay. FIG. 6 includes broken lines indicating a linear regression and an exponential regression of the data.

Figure 7:
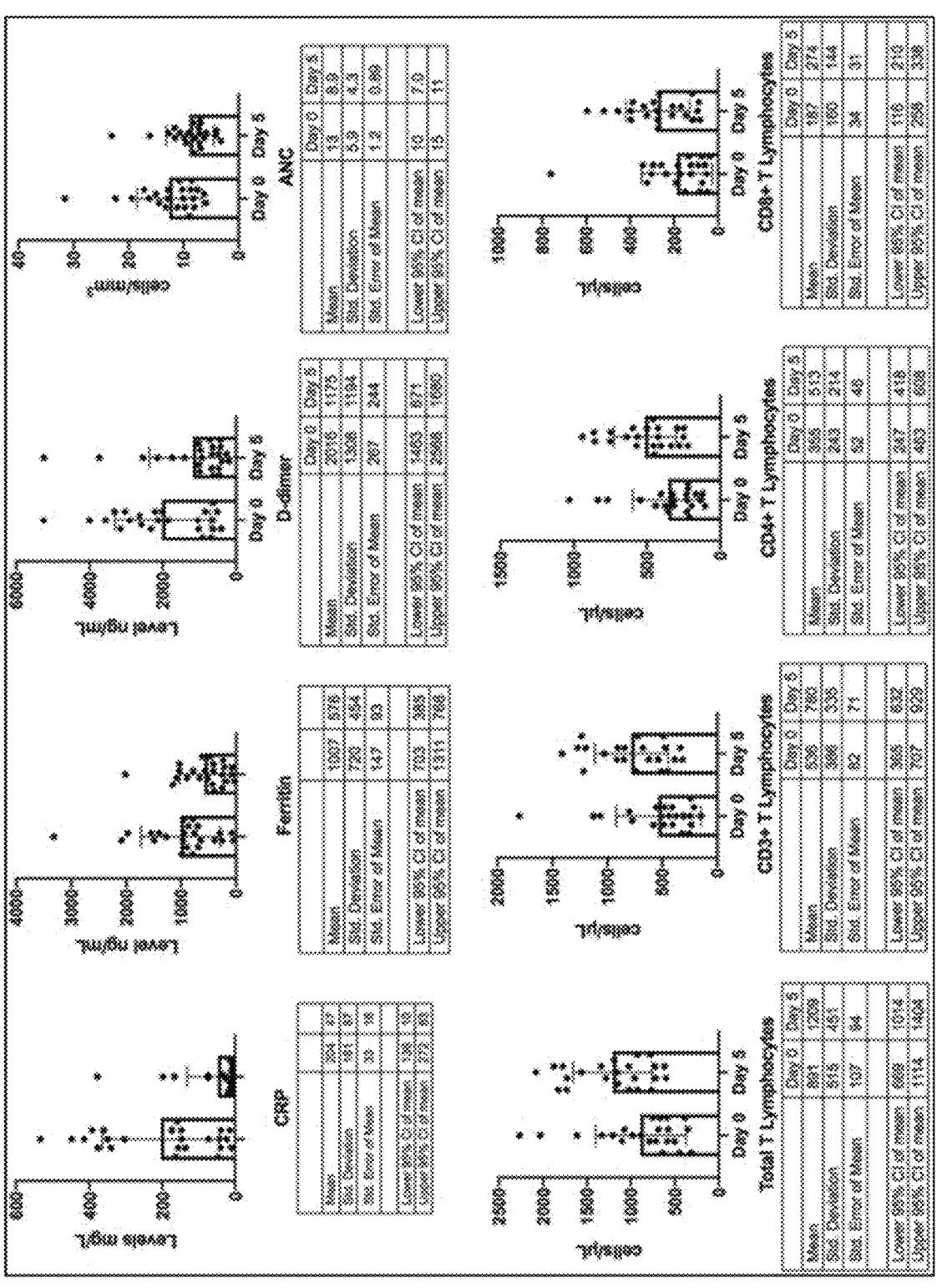

FIG. 7 is a compilation of graphs demonstrating the effect of the invention when administered to patients with severe COVID-19 related ARDS. Biomarkers in clinical study are indicators of mechanism of action to reduce hyperinflammatory state (cytokine storm).

Figure 8:
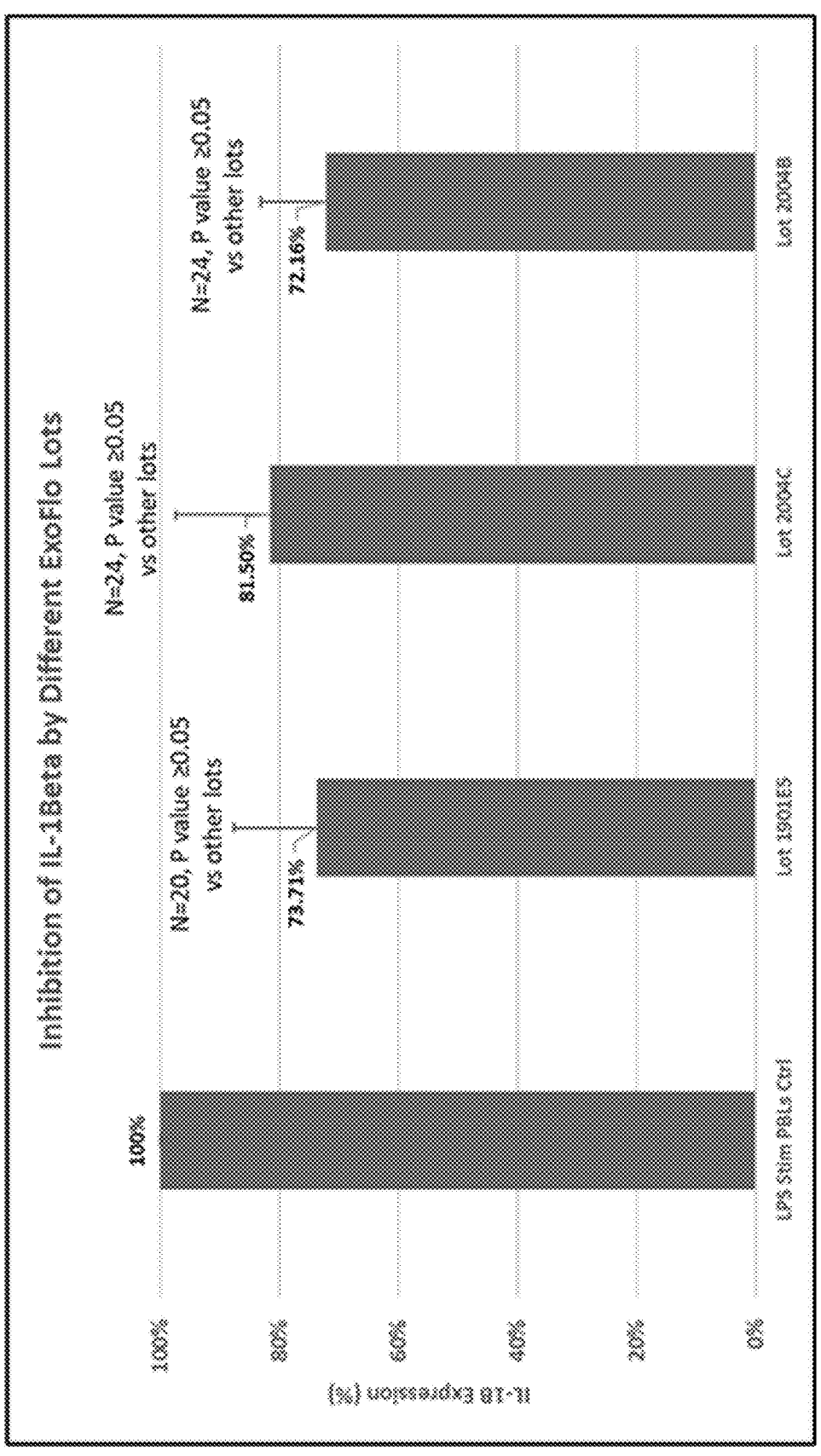
FIG. 8 is a graph illustrating one mechanism of action is to inhibit the master inflammation inducing cytokine, IL-10.

FIG. 8 is a graph illustrating one mechanism of action is to inhibit the master inflammation inducing cytokine, IL-1β. COVID-19 severity is linked to peripheral blood levels of IL-1β. Shown here is the capacity of the disclosed MSC secretome compositions (also referred to under the trade name EXOFLO™) to consistently regulate inflammation through inhibition of the proinflammatory cytokine IL-1β in LPS (lipopolysaccharides, or endotoxin) stimulated human peripheral blood mononuclear cells, an in vitro model used to simulation onset of hyperimmune response, also known as "cytokine storm."

Figure 9:
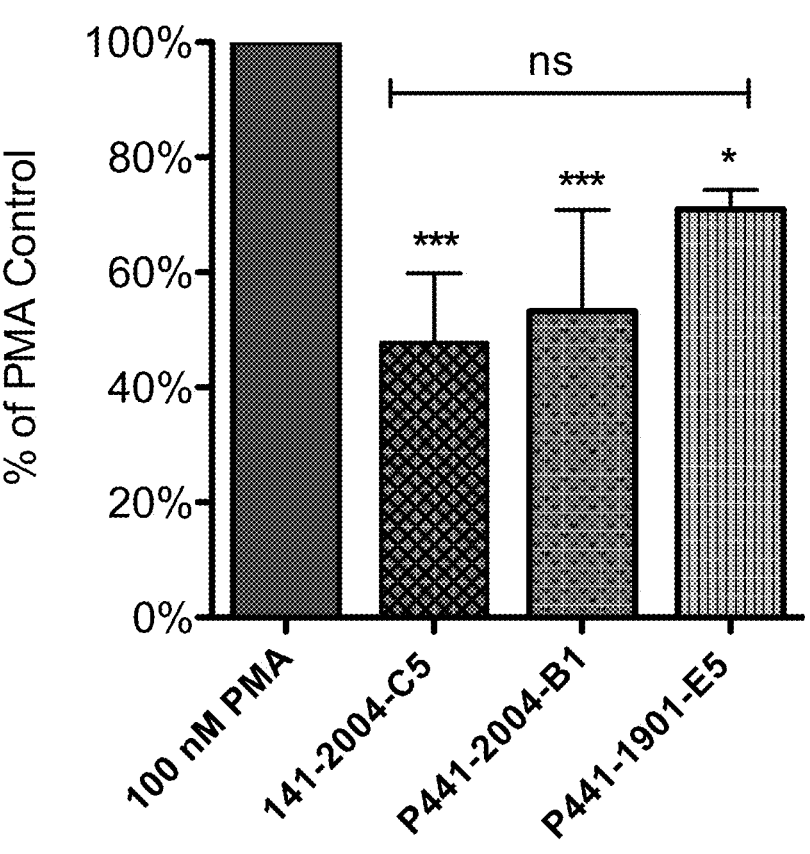
FIG. 9 is a graph illustrating one mechanism of action is to regulate a hyper-active immune response by neutrophils by decreasing neutrophil extracellular trap formation (Netosis).

FIG. 9 illustrates that one mechanism of action is to regulate a hyper-active immune response by neutrophils by decreasing neutrophil extracellular trap formation (Netosis). Shown is the ability of the MSC secretomes (also referred to under the trade name EXOFLO™) to inhibit viral or bacterial induced NETosis through inhibition of neutrophil NET formation and reduce incidence of NET related micro-thrombi formation, for example, that associated with SARS-CoV-2 formation, or high levels of endotoxin associated with bacterial infection. Thus, reduction of NET formation is associated with a decrease in COVID-19 related disseminated intravascular coagulation (micro-clot formation).

What is claimed is:

1. A method for treating acute respiratory distress syndrome (ARDS), the method comprising administering to a subject in need thereof a bone marrow mesenchymal stem cell (MSC) secretome composition comprising stem cell factor 1 (SCF1), ferritin protein, TIMP1 (tissue inhibitor of metalloproteinases 1), and IGFBP-4 (Insulin-like growth factor binding protein-4), wherein the treating comprises ameliorating fluid leakage in the lungs, improving oxygen uptake in the lungs, ameliorating lung damage, and/or ameliorating airway epithelial cell injury.

2. The method of claim 1, wherein the composition (i) increases interleukin-10 (IL-10) secretion by immune regulatory cells to inhibit hyperactive immune cell action; (ii) blocks plasmin production; (iii) suppress micro-blood clotting frequency; (iv) reduces thrombotic emboli; (v) inhibits a pathogen-induced cell death or NETosis; or (vi) any combination of two or more thereof.

3. The method of claim 1, wherein the composition increases (i) the level of total lymphocyte count by at least 20%; (ii) the level of one or more of CD3+ T lymphocytes, CD4+ T lymphocytes, CD8+ T lymphocytes, or combinations thereof by at least 25%; or (iii) both (i) and (ii).

4. The method of claim 1, wherein the composition allows the subject in need thereof to (i) avoid use of a ventilator or (ii) be removed from a ventilator within 72 hours of the administering.

5. The method of claim 1, wherein the composition further comprises bone morphogenetic protein 1 (BMP-1), insulin-like growth factor (IGF-2), TIMP-2 (tissue inhibitor of metalloproteinases 2), transforming growth factor β1 (TGF-β1), CD63 antigen, MIF (Macrophage migration inhibitory factor), furin protein, plasminogen activator inhibitor 1 (PAI-1), thrombomodulin, or macrophage colony stimulating factor (M-CSF), or any combination of two or more thereof.

6. The method of claim 5, wherein the composition further comprises the bone morphogenetic protein 1 (BMP-1), insulin-like growth factor 2 (IGF-2), TIMP-2 (tissue inhibitor of metalloproteinases 2), transforming growth factor β1 (TGF-β1), CD63 antigen, MIF (Macrophage migration inhibitory factor), furin protein, plasminogen activator inhibitor 1 (PAI-1), thrombomodulin, and macrophage colony stimulating factor (M-CSF).

7. The method of claim 5, wherein the composition further comprises the furin protein, plasminogen activator inhibitor 1 (PAI-1), and thrombomodulin.

8. The method of claim 1, wherein the composition further comprises hsa-let-7a-5p, hsa-let-7b-5p, hsa-let-7c-5p, hsa-let-7d-3p, hsa-let-7e-5p, hsa-let-7g-5p, hsa-let-7i, hsa-let-7i-5p, hsa-miR-100-5p, hsa-miR-103a-3p, hsa-miR-106a-5p, hsa-miR-106b-5p, hsa-mir-10b, hsa-miR-10b-5p, hsa-mir-1246, hsa-miR-1246, hsa-miR-125a-5p, hsa-miR-125b-5p, hsa-miR-130a-3p, hsa-mir-130b, hsa-miR-130b-3p, hsa-miR-132-3p, hsa-miR-136-5p, hsa-miR-138-5p, hsa-miR- 139-5p, hsa-mir-140, hsa-miR-140-3p, hsa-miR-145-5p, hsa-mir-146a, hsa-miR-146a-5p, hsa-miR-148a-3p, hsa-miR-152-3p, hsa-miR-15a-5p, hsa-miR-15b-5p, hsa-mir-16-1, hsa-mir-16-2, hsa-miR-16-5p, hsa-miR-17-5p, hsa-miR-181a-5p, hsa-miR-191-5p, hsa-miR-193a-5p, hsa-miR-193b-3p, hsa-miR-197-3p, hsa-miR-199a-3p, hsa-miR-199a-5p, hsa-miR-199b-5p, hsa-miR-19a-3p, hsa-miR-19b-3p, hsa-miR-20a-5p, hsa-mir-203a, hsa-miR-203a-3p, hsa-miR-214-3p, hsa-mir-21, hsa-miR-21-3p, hsa-miR-21-5p, hsa-mir-221, hsa-miR-221-3p, hsa-mir-222, hsa-miR-222-3p, hsa-miR-22-3p, hsa-miR-23a-3p, hsa-miR-23b-3p, hsa-mir-24-1, hsa-mir-24-2, hsa-miR-24-3p, hsa-mir-25, hsa-miR-25-3p, hsa-miR-26a-5p, hsa-miR-27a-3p, hsa-mir-27b, hsa-miR-27b-3p, hsa-miR-29a-3p, hsa-miR-29c-3p, hsa-miR-30a-5p, hsa-miR-30a-5p, hsa-miR-30b-5p, hsa-miR-30c-5p, hsa-mir-30d, hsa-miR-30d-5p, hsa-mir-30e, hsa-miR-30e-5p, hsa-miR-31-3p, hsa-miR-31-5p, hsa-miR-320a, hsa-miR-342-3p, hsa-miR-345-5p, hsa-miR-34a-5p, hsa-miR-361-5p, hsa-miR-376a-3p, hsa-miR-376c-3p, hsa-miR-423-3p, hsa-miR-423-5p, hsa-miR-424-5p, hsa-miR-484, hsa-mir-486-1, hsa-mir-486-2, hsa-miR-486-5p, hsa-miR-570-3p, hsa-miR-574-3p, hsa-miR-663a, hsa-miR-874-3p, hsa-mir-92a-1, hsa-mir-92a-2, hsa-miR-92a-3p, hsa-miR-92b-3p, hsa-mir-93, hsa-miR-93-5p, hsa-miR-940, hsa-miR-99a-5p, or hsa-miR-99b-5p, or any combination of two or more thereof.

9. The method of claim 8, wherein the composition comprises the hsa-miR-21-5p, hsa-miR-24-3p, hsa-miR-222-3p, hsa-miR-27b-3p, hsa-miR-125b-5p, hsa-miR-132-3p, hsa-miR-145-5p, hsa-miR-191-5p, hsa-miR-199a-3p, hsa-miR-221-3p, hsa-miR-22-3p, hsa-miR-23a-3p, hsa-miR-23b-3p, hsa-miR-27a-3p, hsa-miR-29a-3p, hsa-miR-29c-3p, hsa-miR-31-5p, hsa-miR-320a, hsa-miR-34a-5p, hsa-miR-423-3p, hsa-miR-424-5p, or hsa-miR-940, or a combination of two or more thereof.

10. The method of claim 9, wherein the composition comprises the hsa-miR-21-5p, hsa-miR-24-3p, hsa-miR-222-3p, and hsa-miR-27b-3p.

11. The method of claim 1, wherein the composition further comprises an oligosaccharide.

12. The method of claim 1, wherein the composition comprises extracellular vesicles with a size of about 20 nm to about 200 nm.

13. The method of claim 12, wherein the composition comprises from about 0.00001 wt % to about 20 wt % of extracellular vesicles.

14. The method of claim 13, wherein the extracellular vesicles are present in the composition (i) in an amount between about 1 million and about 100 billion vesicles per mL, when formulated as a liquid composition or (ii) in an amount between about 10 million and about 1 trillion, when formulated as a lyophilized powder composition.

15. The method of claim 1, wherein the administering is via parenteral administration.

16. The method of claim 1, wherein the composition is prepared in a method comprising culturing bone marrow mesenchymal stem cells (MSCs) at an oxygen level of 0.1% to 5%.

17. The method of claim 16, wherein the culturing occurs at a pH of 6.0 to 6.9.

* * * * *